(12) United States Patent
Onda et al.

(10) Patent No.: US 10,357,573 B2
(45) Date of Patent: Jul. 23, 2019

(54) BLOCK COPOLYMER CONJUGATE OF PHYSIOLOGICALLY ACTIVE SUBSTANCE

(71) Applicant: Nippon Kayaku Kabushiki Kaisha, Tokyo (JP)

(72) Inventors: Takeshi Onda, Tokyo (JP); Akira Masuda, Tokyo (JP); Ken Yamakawa, Tokyo (JP); Chisato Tomiyama, Tokyo (JP); Yasushi Yoneta, Tokyo (JP); Yuichi Akatsu, Tokyo (JP); Keiichirou Yamamoto, Tokyo (JP); Ayaka Mochizuki, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/548,259

(22) PCT Filed: Feb. 19, 2016

(86) PCT No.: PCT/JP2016/054962
§ 371 (c)(1),
(2) Date: Aug. 2, 2017

(87) PCT Pub. No.: WO2016/136641
PCT Pub. Date: Sep. 1, 2016

(65) Prior Publication Data
US 2018/0050112 A1 Feb. 22, 2018

(30) Foreign Application Priority Data
Feb. 23, 2015 (JP) .................................. 2015-032818

(51) Int. Cl.
*C08G 81/00* (2006.01)
*A61K 31/513* (2006.01)
(Continued)

(52) U.S. Cl.
CPC .............. *A61K 47/60* (2017.08); *A61K 31/05* (2013.01); *A61K 31/337* (2013.01);
(Continued)

(58) Field of Classification Search
CPC ............................. C07D 491/22; A61K 47/60
See application file for complete search history.

(56) References Cited

U.S. PATENT DOCUMENTS 8,703,878 B2    4/2014  Kitagawa et al.
9,018,323 B2 *  4/2015  Yamamoto ............. A61K 31/77
                                                        525/540

(Continued)

FOREIGN PATENT DOCUMENTS

EP    1580216 A1    9/2005
EP    2070971 A1    6/2009
(Continued)

OTHER PUBLICATIONS

International Search Report and Written Opinion dated Mar. 29, 2016 in corresponding PCT application No. PCT/JP2016/054962.
(Continued)

*Primary Examiner* — Hoa (Holly) Le
(74) *Attorney, Agent, or Firm* — Nields, Lemack & Frame, LLC

(57) ABSTRACT

A physiologically active substance-conjugated block copolymer having enhanced efficacy and/or safety is provided by enhancing the property of penetrating into a target diseased tissue and/or enhancing excretability, compared to known physiologically active substance-conjugated block copolymer, and suppressing sensitization of the physiologically active substance to normal tissues other than a target diseased tissue. Disclosed is a block copolymer including a polyethylene glycol segment connected with a polyamino acid derivative segment conjugated with a physiologically (Continued)

active substance, in which the molecular weight of the block copolymer is from 2 kilodaltons to 15 kilodaltons, and the light scattering intensity of a 1 mg/mL aqueous solution of the physiologically active substance-conjugated block copolymer as measured with a laser light scattering photometer is at least twice or more the light scattering intensity of toluene.

21 Claims, 3 Drawing Sheets

(51) Int. Cl.
  A61K 47/60 (2017.01)
  A61K 31/4745 (2006.01)
  C08G 65/333 (2006.01)
  A61K 47/50 (2017.01)
  A61K 31/05 (2006.01)
  A61K 31/337 (2006.01)
  A61P 35/00 (2006.01)

(52) U.S. Cl.
  CPC .......... *A61K 31/4745* (2013.01); *A61K 47/50* (2017.08); *A61P 35/00* (2018.01); *C08G 65/333* (2013.01); *C08G 65/33324* (2013.01); *C08G 81/00* (2013.01); *C08G 2650/04* (2013.01); *C08G 2650/50* (2013.01)

(56) References Cited

U.S. PATENT DOCUMENTS

| 2006/0067910 A1* | 3/2006 | Kitagawa ........... A61K 31/4745 424/78.36 |
| 2009/0012252 A1 | 1/2009 | Masuda et al. |
| 2009/0239782 A1 | 9/2009 | Nakamura et al. |
| 2010/0234537 A1 | 9/2010 | Kitagawa et al. |
| 2013/0331517 A1* | 12/2013 | Yamamoto ............ A61K 31/77 525/54.2 |
| 2014/0328919 A1* | 11/2014 | Zhang .................. A61K 47/482 424/489 |

FOREIGN PATENT DOCUMENTS

| JP | 5-117385 A | 5/1993 |
| JP | 7-69900 A | 3/1995 |
| JP | 2011-225510 A | 11/2011 |
| WO | 2004/039869 A1 | 5/2004 |
| WO | WO-2005079861 A2 * | 9/2005 ............ A61K 47/60 |
| WO | 2006/120914 A1 | 11/2006 |
| WO | 2007/111211 A1 | 10/2007 |
| WO | 2008/041610 A1 | 4/2008 |
| WO | 2009/041570 A1 | 4/2009 |
| WO | 2012/067138 A1 | 5/2012 |
| WO | 2013/155152 A1 | 10/2013 |
| WO | 2016/021407 A1 | 2/2016 |

OTHER PUBLICATIONS

Form PCT/IPEA/409, International Preliminary Report on Patentability dated Jan. 19, 2017 in corresponding PCT application No. PCT/JP2016/054962.
Form PCT/IPEA/408, Written Opinion of the International Preliminary Examination Authority, dated Oct. 25, 2016 in corresponding PCT application No. PCT/JP2016/054962.
Hamaguchi et al., "Phase I Study of NK012, a Novel SN-38-Incorporating Micellar Nanoparticle, in Adult Patients with Solid Tumors," Clinical Cancer Research, vol. 16, pp. 5058-5066, 2010.
Matsumura, "Poly (Amino Acid) Micelle Nanocarriers in Preclinical and Clinical Studies," Advanced Drug Delivery Reviews, vol. 60, pp. 899-914, 2008.
Yokoyama et al., "In Vivo Antitumor Activity of Polymeric Micelle Anticancer Drug Against Murine C 26 Tumor," Journal of Controlled Release, vol. 28, pp. 336-337, 1994.
European communication dated Sep. 17, 2018 in corresponding European patent application No. 16755387.4.

* cited by examiner

[Figure 1]
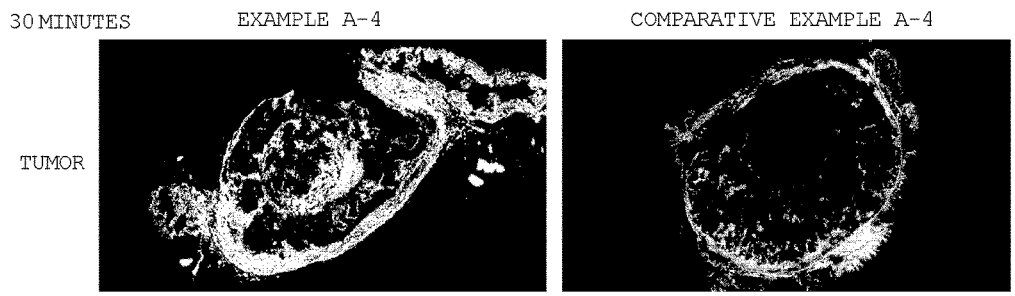
[Figure 2]
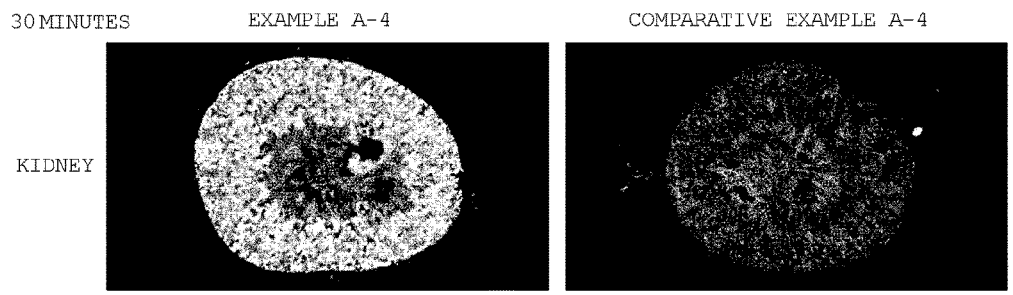
[Figure 3]
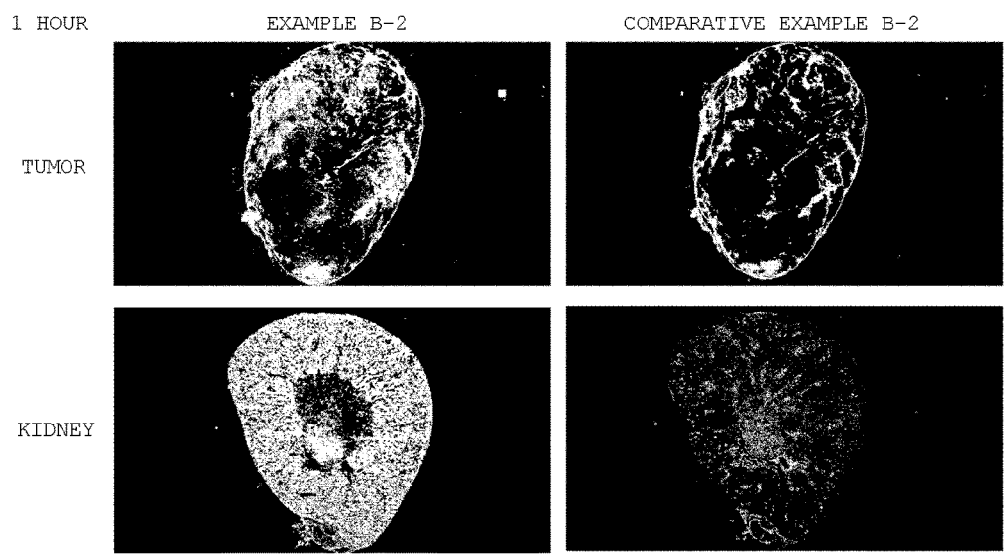

[Figure 4]
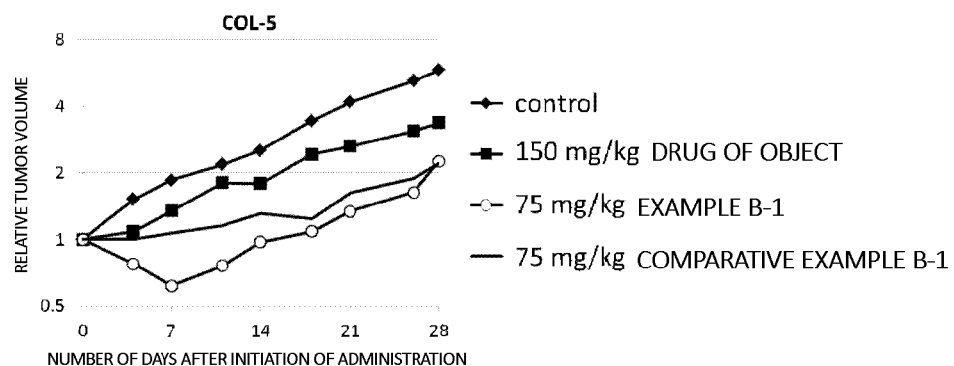
[Figure 5]
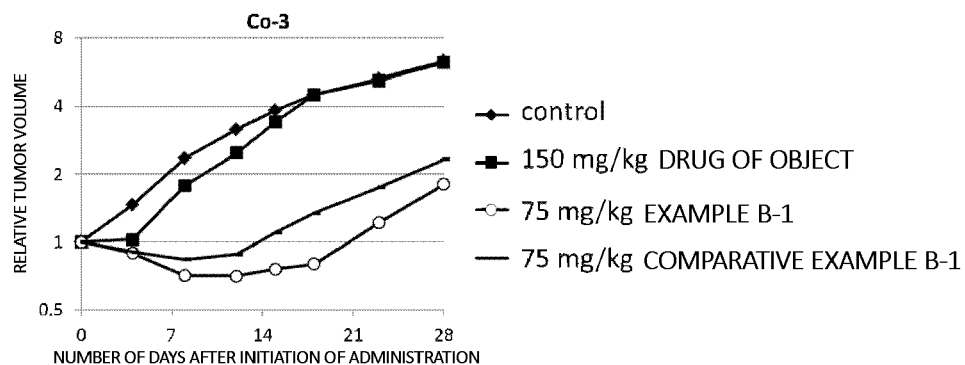
[Figure 6]
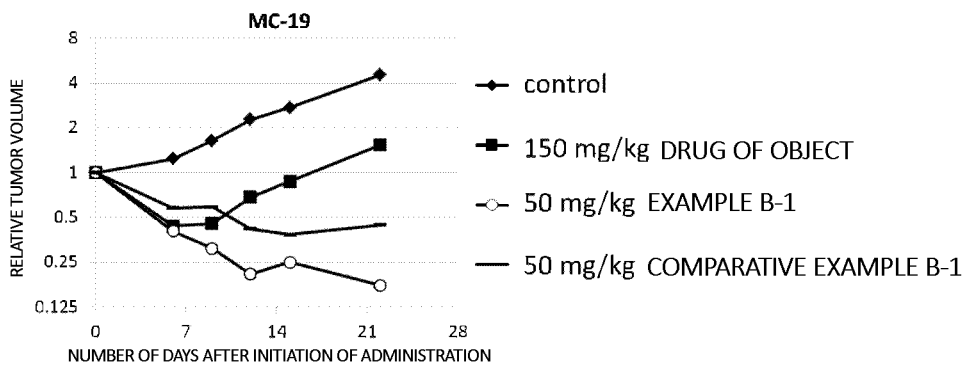

[Figure 7]
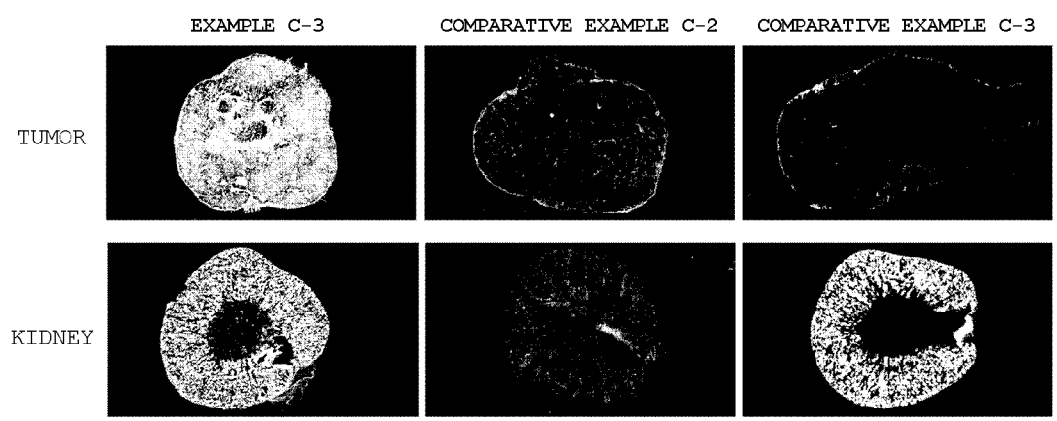

BLOCK COPOLYMER CONJUGATE OF PHYSIOLOGICALLY ACTIVE SUBSTANCE

TECHNICAL FIELD

The present invention relates to a macromolecularized derivative of a physiologically active substance and a use thereof.

BACKGROUND ART

As for pharmaceutical products, drug delivery systems (DDS) that control the pharmacokinetics of physiologically active substances that serve as active ingredients and thereby deliver the physiologically active substances to specific sites of action in vivo at desired drug concentration-action times, have been developed. Non Patent Literature 1 describes a DDS preparation that employs a block copolymer in which a polyethylene glycol segment and a polyamino acid segment are connected together, as a drug delivery carrier. It is described that this block copolymer exhibits associative properties and forms a polymeric micelle configuration with a particle size of 20 to 100 nm, which has a polyethylene glycol outer shell and a hydrophobic inner core, and thus the block copolymer stably encloses various kinds of medicines in the inner core by means of chemical bonding or physical capture. This polymeric micelle type DDS preparation is characterized in that when the DDS preparation is administered in vivo, excretion thereof is suppressed so that retention in vivo is enhanced, and it is known that the DDS preparation migrates passively to tissues such as tumors and is accumulated therein. Therefore, by having a physiologically active substance retained in vivo for a long time period, availability of the active ingredient may be increased, and medicines that utilize these systems make it possible to successfully provide a stronger physiological activity effect compared to the loaded drugs.

In regard to the polymeric micelle type DDS preparation described above, preparations in which a medicine is incorporated into the inner cores of polymeric micelles through chemical bonding are known. For example, Patent Literature 1 describes a preparation example of a camptothecin derivative. Furthermore, Patent Literature 2 describes a preparation example of a resorcin derivative having HSP90 inhibiting activity, Patent Literature 3 describes a preparation example of a taxane derivative, and Patent Literature 4 describes a preparation example of a steroid derivative. Thus, these patent literatures disclose block copolymers conjugated with various physiologically active substances, which may be applied to various medicines.

Conventional physiologically active substance-conjugated block copolymers may increase blood retention of the conjugated medicines. Therefore, the medicines are caused to act for a long period of time on normal tissues as well as diseased tissues. For example, the block copolymer conjugated with a camptothecin derivative, an antitumor agent, which is described in Patent Literature 1, causes the camptothecin derivative to be dissociated in vivo in a release-controlled manner. As a result, the released camptothecin derivative is caused to act for a long period of time on normal tissues such as bone marrow as well as tumor tissues. For this reason, conventional camptothecin derivative-conjugated block copolymers exhibit a strong antitumor effect and also unavoidably manifest myelosuppression such as neutropenia, and this brings about dose limiting toxicity (DLT) (Non Patent Literature 2). Therefore, there is a demand for the development of a camptothecin derivative that exhibits further reduced myelosuppression while maintaining an antitumor effect. As such, conventional physiologically active substance-conjugated block copolymers are capable of exhibiting a strong pharmacological activity effect; however, there have been occasions in which those block copolymers exhibit adverse effects on normal tissues.

Accordingly, in regard to the above-mentioned polymeric micelle type DDS preparations, there is a demand for the development of a physiologically active substance-conjugated block copolymer that suppresses manifestation of a pharmacological activity function on normal tissues and exhibits reduced adverse effects while maintaining a physiological activity function-enhancing effect, which is a feature of the DDS preparation.

CITATION LIST

Patent Literature

Patent Literature 1: WO 2004/039869 A
Patent Literature 2: WO 2008/041610 A
Patent Literature 3: WO 2007/111211 A
Patent Literature 4: WO 2009/041570 A

Non Patent Literature

Non Patent Literature 1: Advanced Drug Delivery Reviews, Vol. 60, 899-914 (2008)
Non Patent Literature 2: Clinical Cancer Research, Vol. 16, 5058-5066 (2010)

SUMMARY OF INVENTION

Technical Problem

It is an object of the present invention to provide a physiologically active substance-conjugated block copolymer having enhanced efficacy and/or safety compared to known physiologically active substance-conjugated block copolymers. Specifically, it is an object to manifest a pharmacological activity effect efficiently by enhancing the penetration performance into a target diseased tissue and thereby enhancing the action of a pharmacologically active substance, compared to known physiologically active substance-conjugated block copolymers. Alternatively, it is an object to avoid occurrence of disorders of normal tissues by controlling blood retention by enhancing the excretability of the block copolymer through the kidneys and the like and thereby suppressing sensitization of the physiologically active substance to normal tissues other than a target diseased tissue.

Solution to Problem

The inventors of the present invention conducted a thorough investigation in order to solve the problems described above, and as a result, the inventors found that a block copolymer in which a polyethylene glycol segment is connected with a polyamino acid derivative segment having a physiologically active substance linked thereto, the molecular weight of the block copolymer is from 2 kilodaltons to 15 kilodaltons, and the light scattering intensity of a 1 mg/mL aqueous solution of the physiologically active substance-conjugated block copolymer as measured with a laser light scattering photometer is at least twice or more the light scattering intensity of toluene under the same measurement conditions as described above, may enhance efficacy and/or safety. Thus, the inventors completed the present invention. According to another aspect, the inventors found that a block copolymer in which a polyethylene glycol segment is connected with a polyamino acid derivative segment having a physiologically active substance linked thereto, and the block copolymer which is capable of forming nanoparticles based on associative properties and has a molecular weight of from 2 kilodaltons to 15 kilodaltons, may enhance efficacy and/or safety. Thus, the inventors completed the present invention.

That is, the present invention relates to the following items [1] to [17].

[1] A block copolymer including a polyethylene glycol segment connected with a polyamino acid derivative segment including an aspartic acid derivative and/or a glutamic acid derivative, and the polyamino acid derivative segment having a physiologically active substance with a hydroxyl group and/or an amino group linked to a side chain carboxyl group of the derivative, wherein the molecular weight of the block copolymer is from 2 kilodaltons to 15 kilodaltons, and the light scattering intensity of a 1 mg/mL aqueous solution of the block copolymer as measured with a laser light scattering photometer under the measurement conditions of a measurement temperature of 25° C., a scattering angle of 90°, and a wavelength of 632.8 nm, is at least twice or more the light scattering intensity of toluene measured under the same measurement conditions.

[2] A block copolymer including a polyethylene glycol segment connected with a polyamino acid derivative segment including an aspartic acid derivative and/or a glutamic acid derivative, and the polyamino acid derivative segment having a physiologically active substance with a hydroxyl group and/or an amino group linked to a side chain carboxyl group of the derivative, wherein the block copolymer having a nanoparticle-forming ability, and the molecular weight of the block copolymer is from 2 kilodaltons to 15 kilodaltons.

[3] The block copolymer according to [1] or [2], wherein the mass content of the polyethylene glycol segment in the block copolymer is from 10% by mass to 80% by mass.

[4] The block copolymer according to [3], wherein the mass content of the polyethylene glycol segment in the block copolymer is from 30% by mass to 65% by mass.

[5] The block copolymer according to any one of [1] to [4], wherein the molecular weight of the polyethylene glycol segment is 1 kilodalton to 10 kilodaltons.

[6] The block copolymer according to any one of [1] to [5], wherein the mass content of the physiologically active substance having the hydroxyl group and/or the amino group in the block copolymer is from 10% by mass to 60% by mass.

[7] The block copolymer according to any one of [1] to [6], wherein the block copolymer is represented by General Formula (1):

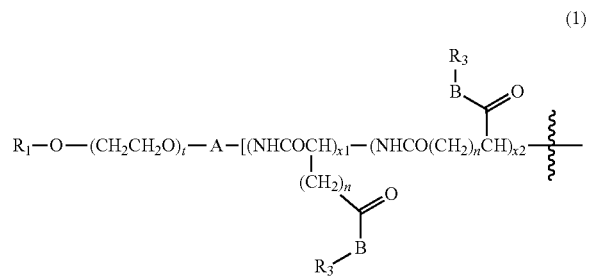

(1)

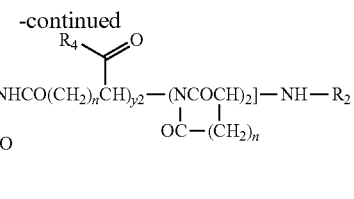

wherein $R_1$ represents a hydrogen atom or a C1-C6 alkyl group which may have a substituent; t represents an integer of 20 to 270; A represents a C1-C6 alkylene group which may have a substituent; $R_2$ represents a substituent selected from the group consisting of a hydrogen atom, a C1-C6 acyl group, and a C1-C6 alkoxycarbonyl group; $R_3$ represents a residue of a physiologically active substance with a hydroxyl group and/or an amino group; $R_4$ represents one or more substituents selected from the group consisting of a linear, branched or cyclic C1-C30 alkoxy group which may have a substituent, a linear, branched or cyclic C1-C30 alkylamino group which may have a substituent, a linear, branched or cyclic C1-C30 dialkylamino group which may have a substituent, a C1-C8 alkylaminocarbonyl-C1-C8 alkylamino group which may have a substituent, a residue of a fluorescent substance, and a hydroxyl group; B represents a linking group; n represents 1 or 2; $x_1$, $x_2$, $y_1$, $y_2$, and z each independently represent an integer of 0 to 25; $(x_1+x_2)$ represents an integer of 1 to 25; $(x_1+x_2+y_1+y_2+z)$ represents an integer of 3 to 25; and the each constituent unit to which $R_3$ or $R_4$ is linked, and the constituent unit in which a side chain carbonyl group is intramolecularly cyclized are each independently randomly arranged.

[8] The block copolymer according to any one of [1] to [7], wherein the physiologically active substance with a hydroxyl group and/or an amino group is one or more physiologically active substances selected from the group consisting of a camptothecin derivative, a taxane derivative, a resorcinol derivative, an anthracycline derivative, a rapamycin derivative, a cytidine-based antimetabolite, a folic acid antimetabolite, a purine-based antimetabolite, a fluorinated pyrimidine-based antimetabolite, a platinum derivative, a mitomycin derivative, a bleomycin derivative, a vinca alkaloid derivative, a podophyllotoxin derivative, a halichondrin derivative, a staurosporine derivative, a thalidomide derivative, a vitamin A derivative, a combretastatin derivative, an antiandrogen agent, an antiestrogen agent, a hormone agent, a tacrolimus derivative, a steroid derivative, a polyene-based antibiotic substance, an azole-based derivative, a candin-based derivative, and a pyrimidine derivative.

[9] The block copolymer according to [8], wherein the physiologically active substance with a hydroxyl group and/or an amino group is one or more antitumor agents selected from the group consisting of a camptothecin derivative, a taxane derivative, a resorcinol derivative, an anthracycline derivative, a rapamycin derivative, a cytidine-based antimetabolite, a folic acid antimetabolite, a purine-based antimetabolite, a fluorinated pyrimidine-based antimetabolite, a platinum derivative, a mitomycin derivative, a bleomycin derivative, a vinca alkaloid derivative, a podophyllotoxin derivative, a halichondrin derivative, a staurosporine derivative, a thalidomide derivative, a vitamin A derivative, a combretastatin derivative, an antiandrogen agent, an antiestrogen agent, and a hormone agent.

[10] The block copolymer according to [7], wherein $R_3$ represents a residue of a camptothecin derivative represented by General Formula (2):

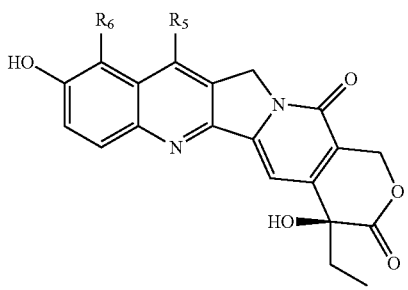

(2)

wherein $R_5$ represents one selected from the group consisting of a hydrogen atom, a C1-C6 alkyl group which may have a substituent, and a silyl group which may have a substituent; and RE represents a hydrogen atom or a C1-C6 alkyl group which may have a substituent.

[11] The block copolymer according to [7], wherein $R_3$ represents a residue of a resorcinol derivative represented by General Formula (3):

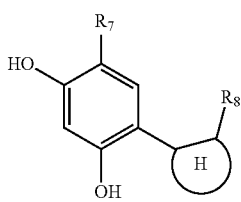

(3)

wherein $R_7$ represents one selected from the group consisting of a mercapto group, a hydroxyl group, a halogen atom, a nitro group, a cyano group, a C1-C20 alkyl group, a C2-C20 alkenyl group, a C2-C20 alkynyl group, a carbocyclic or heterocyclic aryl group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxy group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, a carboxyl group, a C1-C8 alkoxycarbonyl group, a carbamoyl group, and a C1-C8 alkylsilyl group;

$R_8$ represents one selected from the group consisting of a carbocyclic or heterocyclic aryl group which may have a substituent, a C1-C20 alkyl group, a C2-C20 alkenyl group, a C2-C20 alkynyl group, a C1-C20 alkylamino group, and a C1-C20 acylamino group; and ring H represents a heterocyclic aryl group selected from the group consisting of General Formulae (3-1), (3-2), and (3-3):

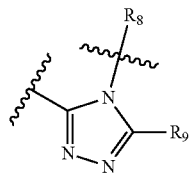

(3-1)

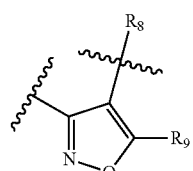

(3-2)

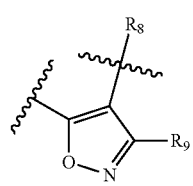

(3-3)

wherein $R_9$ represents one selected from the group consisting of a mercapto group, a hydroxyl group, a hydrogen atom, a halogen atom, a carbamoyl group, a C1-C20 alkoxycarbonyl group, a cyano group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxyl group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, and a C1-C8 alkylsilyl group.

[12] The block copolymer according to [7], wherein $R_3$ represents a residue of paclitaxel, docetaxel, or cabazitaxel.

[13] A block copolymer obtained by reacting a block copolymer in which a polyethylene glycol segment is connected with a polyamino acid segment including aspartic acid and/or glutamic acid, with a physiologically active substance having a hydroxyl group and/or an amino group, and optionally with a hydrophobic substituent having a hydroxyl group and/or an amino group, by using a condensing agent, wherein the molecular weight of the block copolymer is from 2 kilodaltons to 15 kilodaltons, and the light scattering intensity of a 1 mg/mL aqueous solution of the block copolymer as measured with a laser light scattering photometer under the measurement conditions of a measurement temperature of 25° C., a scattering angle of 90°, and a wavelength of 632.8 nm, is at least twice or more the light scattering intensity of toluene measured under the same measurement conditions.

[14] Nanoparticles formed from the block copolymer according to any one of [1] to [13].

[15] The nanoparticles according to [14], wherein a volume average particle diameter of the nanoparticles is less than 20 nanometers.

[16] A pharmaceutical product including the block copolymer according to [1] to [13] or the nanoparticles according to [14] or [15], as an active ingredient.

[17] An antitumor agent including the block copolymer according to [1] to [13] or the nanoparticles according to [14] or [15], as an active ingredient.

Advantageous Effects of Invention

A block copolymer according to the present invention is a block copolymer of a polyethylene glycol segment connected with a polyamino acid segment having a physiologically active substance linked thereto, the molecular weight of the block copolymer is from 2 kilodaltons to 15 kilodaltons, and the light scattering intensity of an aqueous solution of the block copolymer as measured with a laser light scattering photometer is at least twice or more the light scattering intensity of toluene.

According to another aspect, the block copolymer according to the present invention is a block copolymer of a polyethylene glycol segment connected with a polyamino acid derivative segment having a physiologically active substance linked thereto, and the block copolymer having a nanoparticle-forming ability and having a molecular weight of from 2 kilodaltons to 15 kilodaltons.

Nanoparticles that are formed by the block copolymer according to the present invention have a smaller volume average particle diameter than known polymeric micelle type DDS preparations, and have enhanced penetration into a target tissue and/or excretability through the kidneys and the like after being administered in vivo. Therefore, since the physiologically active substance-conjugated block copolymer according to the present invention has high penetration performance into a target tissue compared to known block copolymers, the present physiologically active substance-conjugated block copolymer is capable of sensitizing a physiologically active substance over a wide range of a target tissue, and may therefore efficiently manifest a pharmacological activity effect. Alternatively, since the block copolymer has enhanced excretability through the kidneys and the like, blood retention is controlled so that sensitization of the physiologically active substance to normal tissues other than the target tissue is suppressed, and thereby occurrence of disorders of normal tissues may be avoided.

Particularly, in a case in which an antitumor agent is used as the physiologically active substance, enhancement of an antitumor effect and/or avoidance of disorders in normal tissues such as myelosuppression may be achieved by enhancing the penetration performance into tumor tissues, and/or by enhancing the excretability through the kidneys by using this block copolymer.

BRIEF DESCRIPTION OF DRAWINGS

FIG. 1 presents images showing the tissue distributions of Example A-4 and Comparative Example A-4 in human pancreatic cancer BxPC3 tumor slices.

FIG. 2 presents images showing the tissue distributions of Example A-4 and Comparative Example A-4 in kidney slices.

FIG. 3 presents images showing the tissue distributions of Example B-2 and Comparative Example B-2 in human pancreatic cancer BxPC3 tumor slices and kidney slices.

FIG. 4 illustrates results showing the antitumor effect of Example B-1, Comparative Example B-1, and Ganetespib on human colon cancer Col-5-JCK.

FIG. 5 illustrates results showing the antitumor effect of Example B-1, Comparative Example B-1, and Ganetespib on human colon cancer Co-3-KIST.

FIG. 6 illustrates results showing the antitumor effect of Example B-1, Comparative Example B-1, and Ganetespib on human breast cancer MC-19-JCK.

FIG. 7 presents images showing the tissue distributions of Example C-3, Comparative Example C-2, and Comparative Example C-3 in human pancreatic cancer BxPC3 tumor slices and kidney slices.

DESCRIPTION OF EMBODIMENTS

The present physiologically active substance-conjugated block copolymer is a block copolymer of a polyethylene glycol segment connected with a polyamino acid derivative segment containing an aspartic acid derivative and/or a glutamic acid derivative, the polyamino acid derivative having a physiologically active substance with a hydroxyl group and/or an amino group linked to a side chain carboxyl group of the derivative, in which the molecular weight of the block copolymer is from 2 kilodaltons to 15 kilodaltons, and the light scattering intensity of a 1 mg/mL aqueous solution of the block copolymer measured with a laser light scattering photometer under the measurement conditions of a measurement temperature of 25° C., a scattering angle of 90°, and a wavelength of 632.8 nm is at least twice or more the light scattering intensity of toluene under the aforementioned measurement conditions.

According to another aspect, the present physiologically active substance-conjugated block copolymer is a block copolymer of a polyethylene glycol segment connected with a polyamino acid derivative segment containing an aspartic acid derivative and/or a glutamic acid derivative, the polyamino acid derivative having a physiologically active substance with a hydroxyl group and/or an amino group linked to a side chain carboxyl group of the derivative, in which the block copolymer has a nanoparticle-forming ability, and the molecular weight of the block copolymer is from 2 kilodaltons to 15 kilodaltons.

That is, this block type copolymer is a DDS preparation in which a block type copolymer having a polyethylene glycol segment and a polyamino acid derivative segment connected by an appropriate linking group is used as a main chain, and a physiologically active substance is linked to this. The details thereof will be explained below.

The polyethylene glycol segment for the present block copolymer is a segment having a repeating structure of an ethyleneoxy group: $(CH_2CH_2O)$ unit. The polyethylene glycol segment is preferably a segment structure that includes a polyethylene glycol chain having a degree of ethyleneoxy group unit polymerization of 10 to 300 units, and more preferably a degree of polymerization of 20 to 270 units.

That is, the polyethylene glycol segment is preferably a segment part having a molecular weight of 0.4 kilodaltons to 13 kilodaltons as a molecular weight corresponding to polyethylene glycol, more preferably a structural part having a molecular weight of 0.8 kilodaltons to 12 kilodaltons, and particularly preferably a structural part having a molecular weight of 1 kilodaltons to 10 kilodaltons. A polyethylene glycol segment having a molecular weight of 1 kilodaltons to 5 kilodaltons is especially preferable.

Regarding the molecular weight of the polyethylene glycol segment used for the present invention, the average molecular weight of a polyethylene glycol segment structural compound used in preparing the present block copolymer, which is determined by the peak top molecular weight measured by a GPC method based on polyethylene glycol standard products, is employed.

The terminal group at one end of the polyethylene glycol segment is a connecting group to be linked to the polyamino acid derivative segment that will be described below. The terminal group at the other end is not particularly limited, and examples thereof may include, but not limited to, a hydrogen atom, a hydroxyl group, a C1-C6 alkoxy group which may have a substituent, and a C7-C20 aralkyloxy group which may have a substituent. Examples of the substituent for the alkoxy group and the aralkyloxy group include, but not limited to, a hydroxyl group, an amino group, a formyl group, and a carboxyl group. The polyethylene glycol segment may also be provided with a targeting molecule via the substituent described above. Examples of the targeting molecule include, but not limited to, a protein, a peptide, and folic acid.

The C1-C6 alkoxy group which may have a substituent with regard to the terminal group may be a linear, branched or cyclic C1-C6 alkoxy group. Examples thereof include, but not limited to, a methoxy group, an ethoxy group, a n-propoxy group, an isopropoxy group, a n-butoxy group, an isobutoxy group, a t-butoxy group, a n-pentyloxy group, an isopentyloxy group, a 2-methylbutoxy group, a neopentyloxy group, a 1-ethylpropoxy group, a n-hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, a 2-ethylbutoxy group, a cyclopropoxy group, a cyclopentyloxy group, and a cyclohexyloxy group. A C1-C4 alkoxy group is preferred, and examples thereof include, but not limited to, a methoxy group, an ethoxy group, a n-propoxy group, an isopropoxy group, a n-butoxy group, a s-butoxy group, and a t-butoxy group. Particularly preferred examples include, but not limited to, a methoxy group, an ethoxy group, a n-propoxy group, and an isopropoxy group.

The C7-C20 aralkyloxy group which may have a substituent with regard to the terminal group may be a linear or branched alkyl group of which hydrogen atom at any one site is substituted by an aryl group. Examples thereof include, but not limited to, a benzyloxy group, a 2-phenylethyloxy group, a 4-phenylbutyloxy group, a 3-phenylbutyloxy group, a 5-phenylpentyloxy group, a 6-phenylhexyloy group, and a 8-phenyloctyloxy group. Preferred examples include, but not limited to, a benzyloxy group a 4-phenylbutyloxy group, and a 8-phenyloctyloxy group.

The terminal group of the polyethylene glycol segment is preferably a hydroxyl group or a C1-C6 alkoxy group which may have a substituent.

The polyamino acid derivative segment according to the present invention is a polyamino acid segment including an aspartic acid derivative and/or polyglutamic acid derivative, in which a physiologically active substance with a hydroxyl group and/or an amino group is linked to a side chain carboxyl group of the derivative. That is, the polyamino acid derivative segment is a polyamino acid segment that includes an aspartic acid derivative and/or a glutamic acid derivative, to which at least one or more units of the physiologically active substance are linked. The polyamino acid segment may be a linear polyamino acid segment or may be a segment having a branched structure through side chains. It is preferable that the polyamino acid segment has a segment structure in which 2 to 30 units of amino acids are polymerized. The polyamino acid segment is preferably a polymer of 3 to 25 units, and especially preferably a polymer of 5 to 20 units.

There are no particular limitations on the amino acids that constitute the polyamino acid segment, and any of naturally occurring amino acids, synthetic amino acids, and side chain-modified forms thereof may be used. It is also acceptable to use any of the L-form, D-form, and racemates. Examples of the amino acids may include, but not limited to, glycine, alanine, β-alanine, leucine, phenylalanine, serine, threonine, tyrosine, aspartic acid, glutamic acid, lysine, arginine, histidine, ornithine, and cysteine. Examples of an amino acid having a modified side chain include, but not limited to, an alkyl ester of aspartic acid or glutamic acid, an aralkyl ester of aspartic acid or glutamic acid, an alkylamide of aspartic acid or glutamic acid, an aralkylamide of aspartic acid or glutamic acid, and an alkyloxycarbonyl lysine such as Boc-lysine. The polyamino acid segment may be such that any one kind of these amino acids constitutes the segment, or a mixture of plural kinds of these amino acids may constitute the segment.

Since the polyamino acid segment includes an aspartic acid derivative and/or polyglutamic acid derivative having a side chain carboxyl group to which a physiologically active substance with a hydroxyl group and/or an amino group is linked, it is preferable that the polyamino acid segment is a polyamino acid segment constructed from aspartic acid and/or glutamic acid. More preferably, it is preferable that the polyamino acid segment is a polyaspartic acid segment constructed from aspartic acid only, or a polyglutamic acid segment constructed from glutamic acid only. That is, when the polyamino acid segment includes an aspartic acid derivative in which a physiologically active substance with a hydroxyl group and/or an amino group is linked to a side chain carboxyl group of the derivative, it is preferable to employ a polyaspartic acid segment, and when the polyamino acid segment includes a glutamic acid derivative in which a physiologically active substance with a hydroxyl group and/or an amino group is linked to a side chain carboxyl group of the derivative, it is preferable to employ a polyglutamic acid segment. The mode of polymerization for the polyaspartic acid or polyglutamic acid is a peptide bond, and the polymer may be an α-bonded body, a β-bonded body, or a γ-bonded body, or may be a mixture thereof.

The terminal group at one end of the polyamino acid segment is a connecting group to be linked to the polyethylene glycol segment described above. The terminal group at the other end may be a N-terminal group or a C-terminal group, may be any of an unprotected free amino group, a free carboxylic acid, and a salt thereof, or may be an appropriately modified form of the N-terminal group or the C-terminal group.

Examples of the modified form of the N-terminal group may include, but not limited to, an acylamide type modified form, an alkoxycarbonylamide type modified form (urethane type modified form), and an alkylaminocarbonylamide type modified form (urea type modified form). On the other hand, examples of the modified form of the C-terminal group include, but not limited to, an ester type modified form, an amide type modified form, and a thioester type modified form.

The modifying group for the N-terminal group or the C-terminal group may be any arbitrary modifying group, and preferred examples thereof may include, but not limited to, terminal-modified groups such as a C1-C6 linear, branched or cyclic alkyl group which may have a substituent, a C6-C18 aromatic group which may have a substituent, and a C7-C20 aralkyl group which may have a substituent, all of which are linked to via an appropriate linking group that is linked to the N-terminal group and the C-terminal group.

That is, the N-terminal group is preferably an appropriate acylamide type modified form or alkoxycarbonylamide type modified form (urethane-type modified form), and it is preferable that the N-terminal group is the C1-C6 linear, branched or cyclic alkyl group which may have a substituent, the C6-C18 aromatic group which may have a substituent, or the C7-C20 aralkyl group which may have a substituent, all of which are linked to via a carbonyl group or a carbonyloxy group.

On the other hand, the C-terminal group is preferably an appropriate amide type substituent or ester type substituent, and it is preferable that the C-terminal group is a C1-C8 linear, branched or cyclic alkyl group which may have a substituent, a C6-C18 aromatic group which may have a substituent, or a C7-C20 aralkyl group which may have a substituent, all of which are linked to via an amide group or an ester group.

Examples of the C1-C6 linear, branched or cyclic alkyl group which may have a substituent with regard to the terminal group include, but not limited to, a methyl group, an ethyl group, a n-propyl group, an isopropyl group, a n-butyl group, a t-butyl group, and a cyclohexyl group.

Examples of the C6-C18 aromatic group which may have a substituent with regard to the terminal group include, but not limited to, a phenyl group, a pyridyl group, and a naphthyl group.

The C7-C20 aralkyl group which may have a substituent with regard to the terminal group is a linear or branched alkyl group of which hydrogen atom at any one site is substituted by an aryl group. Examples thereof include, but not limited to, a benzyl group, a 2-phenylethyl group, a 4-phenylbutyl group, and a 8-phenyloctyl group.

It is preferable that the terminal groups of the polyamino acid segment are modified forms based on the N-terminal group and the C-terminal group.

The present invention relates to a block copolymer in which a polyamino acid derivative segment including an aspartic acid derivative and/or a polyglutamic acid derivative is connected with a polyethylene glycol segment, and a physiologically active substance with a hydroxyl group and/or an amino group is linked to the derivative. Regarding the physiologically active substance with a hydroxyl group and/or an amino group, any physiologically active substance with a hydroxyl group and/or an amino group as a bonding-forming functional group by means of an ester bond or an amide bond may be applied without any particular limitations. Any substance including a physiologically active substance may be used, and this physiologically active substance may be applied as the physiologically active substance with a hydroxyl group and/or an amino group, by introducing a hydroxyl group and/or an amino group into the physiologically active substance by converting the physiologically active substance into a derivative or a prodrug.

The present invention is a technology related to the use of a block copolymer as a physiologically active substance carrier, and is a highly usable technology that may be applied to all substances without being particularly affected by the pharmacological activity function or the chemical structure and physical properties of the physiologically active substance used. Therefore, the present invention is not intended to be limited to these physiologically active substances that are applied to the treatment of diseases, and may be applied to any substance as long as the substance is a physiologically active substance having a bond-forming hydroxyl group and/or amino group.

Since the present block copolymer has a feature of having enhanced tissue-penetrating performance, it is preferable to use the block copolymer for the treatment of local tissue diseases. Examples of such a disease include malignant tumor diseases, inflammatory diseases, and infectious diseases. Therefore, in regard to the physiologically active substance according to the present invention, it is preferable to apply active ingredients of pharmaceutical products or pharmaceutically active ingredient candidate compounds to be used for the treatment of these diseases, or to apply active ingredients obtained by converting those compounds into derivatives or prodrugs. Examples of the physiologically active substances that are applicable to the present invention will be listed below; however, the present invention is not intended to be limited to these.

Examples of the physiologically active substance that is used for malignant tumor diseases include, but not limited to, camptothecin derivatives such as 7-ethyl-10-hydroxycamptothecin, irinotecan, nogitecan, and 9-aminocamptothecin; taxane derivatives such as paclitaxel, docetaxel, and cabazitaxel; resorcinol derivatives having HSP90 inhibiting activity, such as ganetespib and luminespib; anthracycline derivatives such as doxorubicin, epirubicin, amrubicin, daunorubicin, idarubicin, and pirarubicin; rapamycin derivatives such as sirolimus, everolimus, and temsirolimus; cytidine-based antimetabolites such as gemcitabin, cytosine arabinoside, enocitabine, cytarabine ocfosfate, ethynylcytidine, azacytidine, and decitabine; folic acid antimetabolites such as methotrexate, pemetrexed, levofolinate, and folinate; purine-based antimetabolites such as fludarabine, nelarabine, pentostatin, and cladribine; fluorinated pyrimidine-based antimetabolites such as doxifluridine, capecitabine, tegafur, fluorouracil, and carmofur; platinum-containing compounds such as cisplatin, carboplatin, oxaliplatin, and nedaplatin; mitomycin derivatives such as mitomycin C; bleomycin derivatives such as bleomycin and libromycin; vinca alkaloid derivatives such as vincristine, vinblastine, vindesine, and vinorelbine; podophyllotoxin derivatives such as etoposide and teniposide; halichondrin derivatives such as eribulin; staurosporine derivatives such as rebeccamycin and UCN-01; thalidomide derivatives such as lenalidomide and pomalidomide; vitamin A derivatives such as tretinoin and tamibarotene; proteasome inhibitors such as bortezomib, carfilzomib, and ixazomib; combretastatin derivatives such as combretastatin A4; MEK inhibitors such as binimetinib, cobimetinib, and trametinib; CDK inhibitors such as dinaciclib, flavopiridol, and palbociclib; Raf kinase inhibitors such as dabrafenib, sorafenib, and vemurafenib; HDAC inhibitors such as vorinostat, belinostat, panabinostat, and romidepsin; actin polymerization inhibitors such as cytochalasin, latrunculin, and phalloidin; PARP inhibitors such as veliparib, rucaparib, and olaparib; tyrosine kinase inhibitors such as crizotinib, imatinib, gefitinib, erlotinib, afatinib, dasatinib, bosutinib, vandetanib, sunitinib, axitinib, pazopanib, lenvatinib, lapatinib, nintedanib, nilotinib, ceritinib, alectinib, ruxolitinib, crizotinib, and ibrutinib; nitrogen mustard-based alkylating agents such as bendamustine, cyclophosphamide, ifosfamide, busulfan, and melphalan; nitrosourea-based alkylating agents such as nimustine, ranimustine, and lomustine; alkylating agents such as dacarbazine, temozolomide, procarbazine, and thiotepa; aromatase inhibitors such as anastrozole, exemestane, letrozole, and fadrozole; antiandrogen derivatives such as hydroxyflutamide, flutamide, bicalutamide, and enzalutamide; CYP17 (lyase) inhibitors such as abiraterone; antiestrogen agents such as tamoxifen and toremifene; and hormone agents such as estramustine, progesterone, mitotane, and medroxyprogesterone.

Examples of the physiologically active substance that is used for inflammatory diseases include, but not limited to, tacrolimus derivatives such as tacrolimus; steroid derivatives such as dexamethasone and prednisolone; rapamycin derivatives such as sirolimus, everolimus, and temsirolimus; immunosuppressants such as cyclosporine, fingolimod, azathioprine, mizoribine, mycophenolate mofetil, and gusperimus; and NSAIDs such as diflunisal and tiaramide.

Examples of the physiologically active substance that is used for infectious diseases include, but not limited to, antifungal agents, such as polyene-based antibiotic substances such as amphotericin B and nystatin, azole-based derivatives such as fluconazole and voriconazole, candin-based derivatives such as micafungin, and pyrimidine derivatives such as flucytosine; antiviral agents such as acyclovir, valacyclovir, and ganciclovir; and antiviral agents such as zanamivir, oseltamivir, and laninamivir.

The present invention is a technology related to the use of a block copolymer as a physiologically active substance carrier, and is a highly usable technology that may be applied to all substances without being particularly affected by the pharmacological activity function or the chemical structure and physical properties of the physiologically active substance used. Therefore, the present invention is not intended to be limited to these physiologically active substances that are applied to the treatment of diseases, and may be applied to any substance as long as the substance is a physiologically active substance having a bond-forming hydroxyl group and/or amino group.

In regard to the physiologically active substance with a hydroxyl group and/or an amino group according to the present invention, it is more preferable to directly use a known pharmaceutically active ingredient or pharmaceutically active ingredient candidate compound, which has a hydroxyl group and/or an amino group, without converting the compound into a derivative or a prodrug. Examples of such a physiologically active substance may include, but not limited to, the following compounds.

Examples of the physiologically active substance that is used for malignant tumor diseases include, but not limited to, camptothecin derivatives such as 7-ethyl-10-hydroxycamptothecin, irinotecan, nogitecan, and 9-aminocamptothecin; taxane derivatives such as paclitaxel, docetaxel, and cabazitaxel; resorcinol derivatives having HSP90 inhibiting activity, such as ganetespib and luminespib; anthracycline derivatives such as doxorubicin, epirubicin, amrubicin, daunorubicin, idarubicin, and pirarubicin; rapamycin derivatives such as sirolimus, everolimus, and temsirolimus; cytidine-based antimetabolites such as gemcitabin, cytosine arabinoside, enocitabine, cytarabine ocfosfate, ethynylcytidine, azacytidine, and decitabine; folic acid antimetabolites such as methotrexate, pemetrexed, levofolinate, and folinate; purine-based antimetabolites such as fludarabine, nelarabine, pentostatin, and cladribine; fluorinated pyrimidine-based antimetabolites such as doxifluridine and capecitabine; platinum-containing compounds such as cisplatin, carboplatin, oxaliplatin, and nedaplatin; mitomycin derivatives such as mitomycin C; bleomycin derivatives such as bleomycin and libromycin; vinca alkaloid derivatives such as vincristine, vinblastine, vindesine, and vinorelbine; podophyllotoxin derivatives such as etoposide and teniposide; halichondrin derivatives such as eribulin; staurosporine derivatives such as rebeccamycin and UCN-01; thalidomide derivatives such as lenalidomide and pomalidomide; vitamin A derivatives such as tretinoin; proteasome inhibitors such as bortezomib and ixazomib; combretastatin derivatives such as combretastatin A4; MEK inhibitors such as binimetinib and cobimetinib; CDK inhibitors such as dinaciclib and flavopiridol; Raf kinase inhibitors such as dabrafenib; HDAC inhibitors such as vorinostat, belinostat and panabinostat; actin polymerization inhibitors such as cytochalasin, latrunculin, and phalloidin; tyrosine kinase inhibitors such as bosutinib, crizotinib, and ibrutinib; nitrogen mustard-based alkylating agents such as melphalan; nitrosourea-based alkylating agents such as nimustine and ranimustine; alkylating agents such as dacarbazine and procarbazine; CYP17 (lyase) inhibitors such as antiandrogen derivatives such as hydroxyflutamide and bicalutamide; antiestrogen agents such as tamoxifen; and hormone agents such as estramustine.

Examples of the physiologically active substance that is used for inflammatory diseases include, but not limited to, tacrolimus derivatives such as tacrolimus; steroid derivatives such as dexamethasone and prednisolone; rapamycin derivatives such as sirolimus, everolimus, and temsirolimus; immunosuppressants such as cyclosporine, fingolimod, mizoribine, mycophenolate mofetil, and gusperimus; and NSAIDs such as diflunisal and tiaramide.

Examples of the physiologically active substance that is used for infectious diseases include, but not limited to, antifungal agents, such as polyene-based antibiotic substances such as amphotericin B and nystatin, azole-based derivatives such as fluconazole and voriconazole, candin-based derivatives such as micafungin, and pyrimidine derivatives such as flucytosine; antiviral agents such as acyclovir, valacyclovir, and ganciclovir; and antiviral agents such as zanamivir, oseltamivir, and laninamivir.

The block copolymer of the present invention has enhanced properties of migrating and penetrating into a target diseased tissue, and has a performance of enhanced excretability through the kidneys and the like. Therefore, sensitization of the physiologically active substance to a normal tissue other than a target diseased tissue is suppressed, and an effect of reducing adverse effects is provided. Therefore, it is preferable to apply a physiologically active substance that is used for diseases with a problem of reducing adverse effects in normal tissues, and it is preferable to use an antitumor agent against malignant tumor diseases or a medicine against inflammatory diseases. Since the block copolymer to which an antitumor agent or an inflammatory disease medicine is applied as the physiologically active substance may enhance the properties of migrating to a tissue such as a tumor or an inflammation site and the properties of penetrating into the interior of a tissue, the block copolymer provides an effect by which an antitumor effect or an antiinflammatory action is enhanced. Since the block copolymer also has excretability through the kidneys and the like, the retention in vivo exhibited by a macromolecularized DDS preparation is controlled, undesirable migration to normal tissues may be suppressed, and reduction of adverse effects may be achieved.

Regarding the physiologically active substance that is used for malignant tumor diseases, the above-mentioned camptothecin derivatives, taxane derivatives, resorcinol derivatives, anthracycline derivatives, rapamycin derivatives, cytidine-based antimetabolites, folic acid antimetabolites, purine-based antimetabolites, fluorinated pyrimidine-based antimetabolites, platinum-containing compounds, mitomycin derivatives, bleomycin derivatives, vinca alkaloid derivatives, podophyllotoxin derivatives, halichondrin derivatives, staurosporine derivatives, thalidomide derivatives, vitamin A derivatives, proteasome inhibitors, combretastatin derivatives, MEK inhibitors, CDK inhibitors, Raf kinase inhibitors, HDAC inhibitors, actin polymerization inhibitors, PARP inhibitors, tyrosine kinase inhibitors, nitrogen mustard-based alkylating agents, nitrosourea-based alkylating agents, alkylating agents, aromatase inhibitors, antiandrogen agents, CYP17 (lyase) inhibitors, antiestrogen inhibitors, and hormone agents are preferred. Camptothecin derivatives, taxane derivatives, resorcinol derivatives, anthracycline derivatives, rapamycin derivatives, cytidine-based antimetabolites, folic acid antimetabolites, and the like are more preferred. Particularly preferred are camptothecin derivatives, taxane derivatives, resorcinol derivatives, and rapamycin derivatives.

Regarding the physiologically active substance that is used for inflammatory diseases, tacrolimus derivatives, steroid derivatives, rapamycin derivatives, immunosuppressants, NSAIDs, and the like are preferred. Tacrolimus derivatives, steroid derivatives, and rapamycin derivatives are particularly preferred.

The physiologically active substance described above is linked to the side chain carboxyl group of aspartic acid or glutamic acid via any arbitrary linking group. The physiologically active substance is linked to the side chain carboxyl group via an ester bond or an amide bond by a hydroxyl group and/or an amino group, and this bond needs to have a bonding property of being slowly cleaved hydrolytically after the block copolymer is administered in vivo and thereby releasing the physiologically active substance.

Since the physiologically active substance has a hydroxyl group and/or an amino group, an embodiment in which this group is used as a bond-forming functional group and is linked to the side chain carboxyl group through an ester bond or an amide bond may be mentioned. This case is a bonding mode that does not involve the use of an arbitrary linking group. Preferably, an embodiment in which a physiologically active substance with a hydroxyl group is used and linked to a side chain carboxyl group via an ester bond is preferred. Regarding the physiologically active substance having an amino bond, it is preferable to use a physiologically active substance having an aromatic amino group, such as a cytidine-based antimetabolite, and an embodiment in which the aromatic amino group is linked to a side chain carboxyl group via an amide bond is preferred.

Regarding the arbitrary linking group that bonds the physiologically active substance to the side chain carboxyl group of aspartic acid or glutamic acid, a group which is capable of linking via an ester bond or an amide bond by utilizing a hydroxyl group and/or an amino group of the physiologically active substance as a bond-forming functional group is preferable. Therefore, any appropriate connecting group having a carboxyl group as a terminal group on one end and with a hydroxyl group, an amino group or a mercapto group capable of linking to the side chain carboxyl group of aspartic acid or glutamic acid as a terminal group on the other end may be used without any particular limitations. Examples of the connecting group include a linear, branched or cyclic C1-C8 alkylene group which may have a substituent, and a C6-C12 aromatic group which may have a substituent.

When the above-mentioned linking group is a linking group that uses a methylene group which may have a substituent as the connecting group, the linking group may be an amino acid derivative or a glycolic acid derivative.

In the case of using an amino acid derivative as the linking group, any of a naturally occurring amino acid or a synthetic amino acid, and a side chain-modified form thereof may be used. Also, any of an L-form, a D-form, and a racemate may be used. Examples thereof may include, but not limited to, glycine, alanine, β-alanine, leucine, phenylalanine, serine, threonine, tyrosine, aspartic acid, glutamic acid, lysine, arginine, histidine, ornithine, and cysteine. Examples of the amino acid having a modified side chain include, but not limited to, an alkyl ester of aspartic acid or glutamic acid, an aralkyl ester of aspartic acid or glutamic acid, an alkylamide of aspartic acid or glutamic acid, an aralkylamide of aspartic acid or glutamic acid, and an alkyloxycarbonyl lysine such as Boc-lysine.

In the case of using a glycolic acid derivative as the linking group, examples include, but not limited to, glycolic acid, lactic acid, malic acid, tartaric acid, and citric acid. In the case of using a polyvalent carboxylic acid, it is preferable that a carboxyl group on one end is linked to the physiologically active substance, and a carboxyl group on the other end is an ester derivative or an amide derivative.

The linking group may be a linking group of a single kind, or there may be a mixture of plural kinds of linking groups.

The polyamino acid derivative segment according to the present invention may include an aspartic acid derivative and/or polyglutamic acid derivative unit, which does not have the physiologically active substance linked to a side chain carboxyl group. In that case, the side chain carboxyl group may be in the form of a free acid or may be in the form of a pharmaceutically acceptable carboxylic acid salt. Examples of the carboxylic acid salt may include, but not limited to, a lithium salt, a sodium salt, a potassium salt, a magnesium salt, a calcium salt, and an ammonium salt.

The aspartic acid derivative and/or polyglutamic acid derivative unit in the polyamino acid derivative segment may be an ester derivative and/or an amide derivative, both having an appropriate substituent. Such a substituent may be arbitrarily introduced for the purpose of controlling the physical properties of the present physiologically active substance-conjugated block copolymer. For example, hydrophobicity of the polyamino acid derivative segment of the physiologically active substance-conjugated block copolymer may be increased by introducing a hydrophobic group thereinto. Meanwhile, hydrophilicity of the polyamino acid segment of the physiologically active substance-conjugated block copolymer may be increased by introducing a hydrophilic substituent including an ionic functional group that is capable of forming a salt, such as an amino group a carboxyl group, or a hydroxyl group.

The ester derivative and/or amide derivative of the aspartic acid derivative and/or polyglutamic acid derivative unit is preferably one or more selected from the group consisting of, for example, a C1-C30 alkoxy group which may have a substituent, a C1-C30 alkylamino group which may have a substituent, a di-C1-C30 alkylamino group which may have a substituent, and a C1-C8 alkylaminocarbonyl-C1-C8 alkylamino group which may have a substituent.

The C1-C30 alkoxy group which may have a substituent may be a linear, branched or cyclic C1-C30 alkoxy group which may have a substituent. That is, it is a derivative in which a side chain carboxyl group has been converted to an ester type derivative. Regarding the substituent, the alkoxy group may include a hydroxyl group, a halogen atom, an amino group, an alkylamino group, a dialkylamino group, an alkoxy group, an aryl group, or the like. Examples of the C1-C30 alkoxy group include, but not limited to, a methoxy group, an ethoxy group, a propoxy group, an isopropoxy group, a butoxy group, a t-butoxy group, a cyclohexyloxy group, a benzyloxy group, a 4-phenylbutoxy group, an octyloxy group, a decyloxy group, a dodecyloxy group, a tetradecyloxy group, a hexadecyloxy group, an octadecyloxy group, an eicosyloxy group, a docosyloxy group, a tetracosyloxy group, a hexacosyloxy group, an octacosyloxy group, and a triacontyloxy group.

The C1-C30 alkylamino group which may have a substituent may be a linear, branched or cyclic C1-C30 alkylamino group which may have a substituent. That is, it is a derivative in which a side chain carboxyl group has been converted to an alkylamide type derivative. Regarding the substituent, the alkylamino group may include a hydroxyl group, a halogen atom, an amino group, an alkylamino group, a dialkylamino group, an alkoxy group, an aryl group, or the like. Examples of the C1-C30 alkylamino group include, but not limited to, a methylamino group, an ethylamino group, a propylamino group, an isopropylamino group, a butylamino group, a t-butylamino group, a cyclohexylamino group, a benzylamino group, a 4-phenylbutylamino group, an octylamino group, a decylamino group, a dodecylamino group, a tetradecylamino group, a hexadecylamino group, an octadecylamino group, an eicosylamino group, a docosylamino group, a tetracosylamino group, a hexacosylamino group, an octacosylamino group, and a triacontylamino group.

The class of the alkylamino group also includes a residue of an amino acid having a protected carboxyl group or a fluorescent substance having an amino group. As the amino acid having a protected carboxyl group, for example, glycine methyl ester, glycine benzyl ester, β-alanine methyl ester, β-alanine benzyl ester, alanine methyl ester, leucine methyl ester, and phenylalanine methyl ester may be used.

Regarding the fluorescent substance having an amino group, for example, 2-(2-aminoethoxy)-9-(diethylamino)-5H-benzo[a]phenoxazin-5-one, BODIPY (registered trademark) TR Cadaverine, BODIPY (registered trademark) FL Ethylenediamine, ALEXA FLUOR (registered trademark) 594 Cadaverine, TEXAS RED (registered trademark) Cadaverine, and ATTO 594 amine are also included, and amide bond residues thereof are included.

The di-C1-C30 alkylamino group which may have a substituent may be a linear, branched or cyclic di-C1-C30 alkylamino group which may have a substituent. That is, it is a derivative in which a side chain carboxyl group has been converted to a dialkylamide type derivative. Regarding the substituent, the dialkylamino group may include a hydroxyl group, a halogen atom, an amino group, an alkylamino group, a dialkylamino group, an alkoxy group, an aryl group, and the like. Examples of the di-C1-C30 alkylamino group include, but not limited to, a dimethylamino group, a diethylamino group, a dipropylamino group, a diisopropylamino group, a dibutylamino group, a pyrrolidino group, a piperidino group, a dibenzylamino group, a N-benzyl-N-methylamino group, a dioctylamino group, a dinonylamino group, a didecylamino group, a didodecylamino group, a ditetradecylamino group, a dihexadecylamino group, a dioctadecylamino group, and a dieicoylamino group.

The C1-C8 alkylaminocarbonyl-C1-C8 alkylamino group which may have a substituent may be a urea type derivative substituted with a linear, branched or cyclic C1-C8 alkyl group which may have a substituent. The alkyl groups may be of the same kind or may be of different kinds. Regarding the substituent, the alkylaminocarbonylalkylamino group may include a hydroxyl group, a halogen atom, an amino group, an alkylamino group, a dialkylamino group, an alkoxy group, an aryl group, and the like. When the alkylaminocarbonylalkylamino group has a substituent, a dialkylamino group is preferred. Examples of the C1-C8 alkylaminocarbonyl-C1-C8 alkylamino group which may have a substituent include, but not limited to, a methylaminocarbonylmethylamino group, an ethylaminocarbonylethylamino group, an isopropylaminocarbonylisopropylamino group, a cyclohexylaminocarbonylcyclohexylamino group, an ethylaminocarbonyl-(3-dimethylaminopropyl)amino group, and a (3-dimethylaminopropyl)aminocarbonylethylamino group.

The ester derivative and/or amide derivative of the aspartic acid derivative and/or polyglutamic acid derivative unit may be derivatives of the same kind, or may be a mixture of derivatives of different kinds. It is also acceptable that the side chain carboxyl group is a free acid or a mixture of salts thereof.

In the present block copolymer, a polyethylene glycol segment and a polyamino acid derivative segment are connected together. The linkage mode is not particularly limited as long as a group which links two polymer segments by chemical bonding is used, and a connecting group including functional groups that may be respectively linked to a polyethylene glycol terminal group and a polyamino acid derivative terminal group is desirable. Preferred is a C1-C6 alkylene group having bonding functional groups as terminal groups. The type of bonding to the polyethylene glycol segment is preferably an ether bond by means of a terminal oxygen atom of a polyoxyethylene group: ($CH_2CH_2O$), and the type of bonding to the polyamino acid derivative segment is preferably an amide bond or an ester bond. That is, the connecting group is preferably a —($CH_2$)s-NH— group (wherein s represents an integer of 1 to 6) or a —($CH_2$)s-CO— group (wherein s represents an integer of 1 to 6).

The present block copolymer is characterized by having a molecular weight of from 2 kilodaltons to 15 kilodaltons. Regarding the molecular weight of the block copolymer, a calculated value obtained by summing the respective constituent molecular weight of each constituent part is employed as the molecular weight of the block copolymer. That is, the calculated value obtained by summing (1) the molecular weight of the polyethylene glycol segment, (2) the molecular weight of the main chain part of the polyamino acid derivative segment, (3) the total molecular weight of the physiologically active substance obtained by multiplying the molecular weight of a residue of the physiologically active substance by the number of the bonds thereof, and (4) the total molecular weight of substituents other than the physiologically active substance obtained by multiplying the molecular weight of residues of the substituents by the number of the bonds thereof, is employed as the molecular weight. Therefore, the two terminal groups of the block copolymer or the connecting groups that constitute the block copolymer are not taken into consideration for the calculation of the molecular weight of the block copolymer, as far as there is no particular reason.

The molecular weight of the block copolymer may be a molecular weight defined with an accuracy of the unit of kilodaltons. Therefore, the method for analyzing the various constituent parts is not particularly limited as long as it is an analysis method with sufficient accuracy for the measurement of the molecular weight of the polyamino acid derivative to the unit of kilodaltons, and various analysis methods may be selected as appropriate. Preferable analysis method for the each constituent part will be described below.

The molecular weight of the polyethylene glycol segment in the above (1) is a measured value of the molecular weight of the polyethylene glycol compound that constitutes the polyethylene glycol segment, and an average molecular weight that may be determined by the peak top molecular weight measured by a GPC method based on polyethylene glycol standard products is employed.

The molecular weight of the main chain part of the polyamino acid derivative segment in the above (2) is a calculated value obtained by multiplying the average molecular weight of the polymerized monomer unit of the segment by the average number of polymerized units. Regarding the number of polymerized units, it is preferable to use a number of polymerized units calculated by a method of quantitatively determining the side chain carboxyl groups of the polyamino acid by neutralization titration, or a number of polymerized units calculated from the integral values of $^1$H-NMR. It is preferable to use a neutralization titration method.

The total molecular weight of the physiologically active substance in the above (3) is a calculated value obtained by multiplying the molecular weight of the physiologically active substance by the number of the bonds. The number of the bonds may be determined by a method of calculating the number of the bonds from weight measurement of an unreacted portion of the physiologically active substance in the reaction liquid by HPLC, or by a method of cleaving the physiologically active substance from the physiologically active substance-conjugated block copolymer, and quantitatively analyzing the released physiologically active substance or fragment molecules originating therefrom.

The total molecular weight of substituents other than the physiologically active substance in the above (4) is a calculated value obtained by multiplying the molecular weight of the residues of the substituents by the number of the bonds thereof. The number of bonds of the substituents may be determined by a method of measuring and calculating unreacted residues in the reaction liquid by HPLC, or by a quantitative analysis after hydrolysis from polyamino acid. The number of polymerized units may also be calculated from the integral values of $^1$H-NMR.

The present block copolymer has a molecular weight of from 2 kilodaltons to 15 kilodaltons. When the molecular weight is smaller than 2 kilodaltons, this implies that the physiologically active substance-conjugated block copolymer does not have a sufficient nanoparticle-forming ability, and sufficient penetrating performance into a target tissue is not obtained. Therefore, the pharmacological action effect of the physiologically active substance may not be efficiently manifested. On the other hand, when the molecular weight is larger than 15 kilodaltons, the block copolymer has suppressed kidney excretability, and thus, retention in vivo is enhanced. Accordingly, sensitization of the physiologically active substance to normal tissues other than a target diseased tissue may occur, and therefore, there is a risk that normal tissues may exhibit disorders. For example, when a cytotoxic physiologically active substance is used, persistence of blood toxicity associated with myelopathy may be considered. Therefore, it is necessary to control the molecular weight to be 15 kilodaltons or less. The molecular weight of the block copolymer is preferably from 3 kilodaltons to 12 kilodaltons, and more preferably from 3 kilodaltons to 10 kilodaltons.

The present block copolymer having a physiologically active substance conjugated therewith has a property of exhibiting self-association in an aqueous solution. That is, the physiologically active substance-conjugated block copolymer has a property in which when a 1 mg/mL aqueous solution of the physiologically active substance-conjugated block copolymer is subjected to a particle size distribution analysis based on a dynamic light scattering method using laser light, the physiologically active substance-conjugated block copolymer is measured as nanoparticles having a volume average particle diameter of about a few nanometers to about 20 nanometers. It is preferable that the present physiologically active substance-conjugated block copolymer has a property in which the block copolymer forms nanoparticles having a particle size of less than 20 nanometers at the maximum in a 1 mg/mL aqueous solution. In this case, a particle size distribution analysis in an aqueous solution based on pure water is employed. Preferably, the physiologically active substance-conjugated block copolymer is characterized in that the volume average particle diameter is measured to be less than 20 nanometers by a particle size distribution analysis method based on a dynamic light scattering method using laser light, and more preferably, the block copolymer has a property in which the block copolymer is analyzed as nanoparticles having a particle size of 3 to 15 nanometers.

The volume average particle diameter according to the present invention is the particle size of the peak that exists at the largest proportion in a volume distribution that may be measured with, for example, a ZetaPotential/Particlesizer NICOMP 380 ZLS (analysis method: NICOMP method) manufactured by Particle Sizing Systems, LLC, or a particle size zeta potential analyzer, ZETASIZER NANO ZS (analysis method: NNLS method) manufactured by Malvern Instruments, Ltd.

Since the present physiologically active substance-conjugated block copolymer is a block copolymer in which a hydrophilic polyethylene glycol segment is connected with a polyamino acid derivative segment that exhibits hydrophobicity by means of a physiologically active substance or another hydrophobic side chain, it is considered that in an aqueous solution, the polyamino acid derivative segments of a plurality of the block copolymer molecules associate with one another based on the hydrophobic interaction of the polyamino acid derivative segment. Consequently, it is speculated that micelle-like associated bodies having a core-shell structure are formed, in which the polyamino acid derivative segment forms an inner core (core part) and the hydrophilic polyethylene glycol segment covers the periphery of the inner core and forms an outer shell layer (shell part), and these are observed as the nanoparticle described above.

The present physiologically active substance-conjugated block copolymer needs to have a property of forming nanoparticles in an aqueous solution, for the purpose of enhancing the pharmacological action effect of the physiologically active substance and/or reducing adverse effects.

It is effective to use the light scattering intensity obtained by using laser light, as an index for the nanoparticle-forming properties of the present block copolymer conjugated with a physiologically active substance. That is, the nanoparticle-forming properties of the physiologically active substance-conjugated block copolymer in an aqueous solution may be checked by utilizing the laser light scattering intensity as an index. In that case, a method of checking the nanoparticle-forming properties of the physiologically active substance-conjugated block copolymer in an aqueous solution by using toluene as a light scattering intensity standard sample, and utilizing the relative intensity with respect to toluene as an index, is effective.

The present block copolymer conjugated with a physiologically active substance is such that the laser light scattering intensity in a 1 mg/mL aqueous solution of the block copolymer is at least twice or more as a relative intensity with respect to the light scattering intensity of toluene.

If the relative light scattering intensity is smaller than twice, it is shown that the physiologically active substance-conjugated block copolymer does not have sufficient nanoparticle-forming properties, and sufficient penetrating performance into a target tissue is not obtained. Therefore, the pharmacological action effect of the physiologically active substance may not be efficiently manifested. According to the present invention, the value of the relative light scattering intensity is an index indicating that the block copolymer has a nanoparticle-forming ability, and any value is acceptable as long as it is twice the light scattering intensity of toluene, without any particular limitations. That is, it can be said that even if the relative light scattering intensity is higher than 100 times, the block copolymer has a sufficient nanoparticle-forming ability. However, it may be considered that there is a possibility that if the light scattering intensity is higher than 100 times, the block copolymer may not have desirable excretability. In that case, since the retention in vivo of the block copolymer increases, sensitization of the physiologically active substance to normal tissues other than a target diseased tissue may occur, and therefore, there is a risk that normal tissues may exhibit disorders. Therefore, it is appropriate to control the relative light scattering intensity to be 100 times or less.

The present physiologically active substance-conjugated block copolymer is such that the light scattering intensity of an aqueous solution thereof is preferably 2 times to 50 times, and more preferably from 2 times to 30 times, as a relative intensity with respect to the light scattering intensity of toluene.

In regard to the method for measuring the light scattering intensity obtained by using laser light for the analysis of the nanoparticle-forming properties of the present physiologically active substance-conjugated block copolymer, a method of using a 1 mg/mL aqueous solution of the physiologically active substance-conjugated block copolymer as a measurement sample, and measuring the light scattering intensity with a laser light scattering photometer at a measurement temperature of 25° C., a scattering angle of 90°, and a wavelength of 632.8 nm is suitable. Examples of the measuring instrument may include, but not limited to, a dynamic light scattering photometer manufactured by Otsuka Electronics Co., Ltd., DLS-8000DL (measurement temperature: 25° C., scattering angle: 900, wavelength: 632.8 nm, ND filter: 2.5%, PH1: OPEN, PH2: SLIT).

The measurement of the light scattering intensity is an analyzed value obtained by using an aqueous solution prepared using pure water that does not include microparticles as an analytic sample. The aqueous solution may be optionally dissolved by means of ultrasonic irradiation during solution preparation. The aqueous solution thus prepared is preferably an aqueous solution that has been further subjected to a filtration treatment in order to remove submicron-sized microparticles.

Regarding toluene that is used as a standard substance for the measurement of light scattering intensity, any toluene may be used without particular limitations as long as the toluene has reagent-level purity. It is preferable to use toluene that has been subjected to pretreatment filtration, which is usually performed for the preparation of a sample for a light scattering analysis.

The present block copolymer is preferably such that the mass content of the polyethylene glycol segment is from 10% by mass to 80% by mass. That is, it is preferable that the proportion occupied by the molecular weight corresponding to the polyethylene glycol segment in the molecular weight of the block copolymer is 10% by mass to 80% by mass. If the mass content of the polyethylene glycol segment is less than 10% by mass, there is a risk that water-solubility may be decreased noticeably, and thus nanoparticles based on self-association may not be formed in an aqueous solution. On the other hand, if the mass content of the polyethylene glycol segment is more than 80% by mass, the constitution part of the polyamino acid derivative segment that is responsible for self-association properties is reduced, and therefore, there is a risk that nanoparticle-forming properties based on hydrophobic interaction may be lowered. It is preferable to set the mass content of the polyethylene glycol segment so as to achieve sufficient efficacy and reduction of adverse effects.

The ratio of the mass molecular weight of the polyethylene glycol segment is more preferably from 20% by mass to 70% by mass, and especially preferably from 30% by mass to 65% by mass.

The present block copolymer is preferably such that the mass content of the physiologically active substance with a hydroxyl group and/or an amino group is preferably from 10% by mass to 60% by mass. If the content ratio of the physiologically active substance is lower than 10% by mass, there is a risk that the amount of the active ingredient exhibiting pharmacological activity may become small, and efficacy may be lowered. On the other hand, if the content ratio of the physiologically active substance is larger than 60% by mass, there is a risk that the balance of self-association properties of the block copolymer may be noticeably deteriorated, and the desirable nanoparticle-forming properties may not be provided.

The mass content of the pharmacologically active substance is preferably from 10% by mass to 50% by mass, and more preferably from 10% by mass to 40% by mass.

The present block copolymer is preferably a block copolymer represented by General Formula (1):

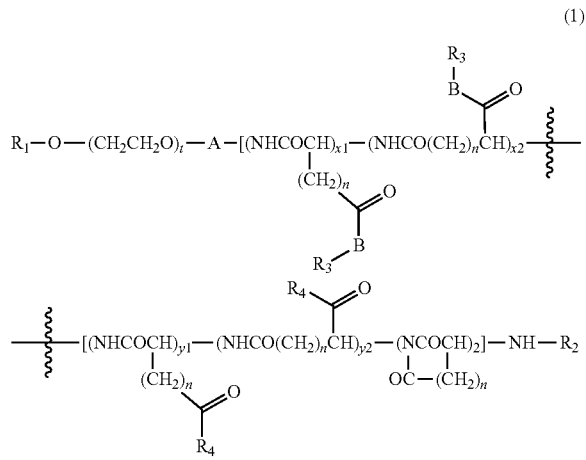

wherein $R_1$ represents a hydrogen atom or a C1-C6 alkyl group which may have a substituent; t represents an integer of 20 to 270; A represents a C1-C6 alkylene group which may have a substituent; $R_2$ represents a substituent selected from the group consisting of a hydrogen atom, a C1-C6 acyl group, and a C1-C6 alkoxycarbonyl group; $R_3$ represents a residue of a physiologically active substance with a hydroxyl group and/or an amino group;

$R_4$'s represent one or more substituents selected from the group consisting of a linear, branched or cyclic C1-C30 alkoxy group which may have a substituent, a linear, branched or cyclic C1-C30 alkylamino group which may have a substituent, a linear, branched or cyclic C1-C30 dialkylamino group which may have a substituent, a C1-C8 alkylaminocarbonyl-C1-C8 alkylamino group which may have a substituent, a residue of a hydrophobic fluorescent substance, and a hydroxyl group; B represents a connecting group; n represents 1 or 2; $x_1$, $x_2$, $y_1$, $y_2$, and z each independently represent an integer of 0 to 25; $(x_1+x_2)$ represents an integer of 1 to 25; $(x_1+x_2+y_1+y_2+z)$ represents an integer of 3 to 25; and the each constituent unit to which $R_3$ or $R_4$ is linked, and the constituent unit in which a side chain carbonyl group is intramolecularly cyclized are each independently randomly arranged.

The C1-C6 alkyl group which may have a substituent for $R_1$ may be a linear, branched or cyclic C1-C6 alkyl group which may have a substituent. Examples thereof include, but not limited to, a methyl group, an ethyl group, a n-propyl group, an isopropyl group, a n-butyl group, a s-butyl group, a t-butyl group, a n-pentyl group, a cyclopentyl group, a n-hexyl group, and a cyclohexyl group.

Examples of the substituent that may be carried may include, but not limited to, a halogen atom, a nitro group, a cyano group, a hydroxyl group, a mercapto group, a carbocyclic or heterocyclic aryl group, an alkylthio group, an arylthio group, an alkylsulfinyl group, an arylsulfinyl group, an alkylsulfonyl group, an arylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, an alkoxycarbonylamino group, a ureido group, a sulfonylamino group, a sulfamoylamino group, a formyl group, an acyl group, a carboxyl group, an alkoxycarbonyl group, a carbamoyl group, and a silyl group. The position of substitution on the aromatic ring may be the ortho-position, the meta-position, or the para-position.

Examples of $R_1$ include, but not limited to, a methyl group, an ethyl group, a n-propyl group, an isopropyl group, a n-butyl group, a s-butyl group, a t-butyl group, a benzyl group, a 2,2-dimethoxyethyl group, a 2,2-diethoxyethyl group, and a 2-formylethyl group. Particularly, a methyl group, an ethyl group, a n-propyl group, an isopropyl group, a n-butyl group, a s-butyl group, a t-butyl group, and the like are more preferred.

t in General Formula (1) represents the number of polymerized ethyleneoxy groups in the polyethylene glycol segment. This t is an integer of 20 to 270. That is, the molecular weight of the polyethylene glycol segment is 0.8 kilodaltons to 12 kilodaltons.

If this t is smaller than 20, the physiologically active substance-conjugated block copolymer thus obtainable does not have sufficient water-solubility, and there is a risk that the desired biokinetics may not be presented. On the other hand, if this t is larger than 270, the content of the polyamino acid derivative segment that is responsible for relative hydrophobicity becomes smaller, and therefore, there is a risk that desired self-association properties may not be obtained, and the biokinetics associated therewith may not be presented. This t is preferably an integer of 22 to 230, and more preferably an integer of 30 to 180. That is, the molecular weight of the polyethylene glycol segment is preferably 1 kilodalton to 10 kilodaltons, and more preferably 1.3 kilodaltons, to 8 kilodaltons.

Examples of the C1-C6 alkylene group which may have a substituent for A include, but not limited to, a methylene group, an ethylene group, a n-propylene group, and a n-butylene group. Regarding the substituent that may be carried, a hydroxyl group, a halogen atom, an amino group, an alkylamino group, a dialkylamino group, an alkoxy group, an aryl group, or the like may be included.

Particularly, this A is more preferably an ethylene group or a n-propylene group.

The C1-C6 acyl group which may have a substituent for $R_2$ may be a linear, branched or cyclic C1-C6 acyl group which may have a substituent. Regarding the substituent, a hydroxyl group, a halogen atom, an amino group, an alkylamino group, a dialkylamino group, an alkoxy group, an aryl group, or the like may be included. Examples of the C1-C6 acyl group for $R_2$ include, but not limited to, a formyl group, an acetyl group, a trichloroacetyl group, a trifluoroacetyl group, a propionyl group, a pivaloyl group, a benzylcarbonyl group, and a phenethylcarbonyl group. A linear, branched or cyclic C1-C4 acyl group which may have a substituent is more preferred, and an acetyl group, a trichloroacetyl group, and a trifluoroacetyl group are more preferred.

The C1-C6 alkoxycarbonyl group which may have a substituent for $R_2$ may be a linear, branched or cyclic C1-C6 alkoxycarbonyl group which may have a substituent. Regarding the substituent, a hydroxyl group, a halogen atom, an amino group, an alkylamino group, a dialkylamino group, an alkoxy group, an aryl group, or the like may be included. Examples of the C1-C6 alkoxycarbonyl group for $R_2$ include, but not limited to, a methoxycarbonyl group, an ethoxycarbonyl group, a t-butoxycarbonyl group, a benzyloxycarbonyl group, and a 9-fluorenylmethyloxycarbonyl group.

$R_3$ represents a residue for a physiologically active substance with a hydroxyl group and/or an amino group. That is, the hydroxyl group and/or amino group is a linkable functional group, and the residue represents a residue obtained by excluding a hydrogen atom from this bond-forming functional group. This physiologically active substance with a hydroxyl group and/or an amino group may be used without any particular limitations. However, since the purpose of the present invention is to be used as a pharmaceutical product, it is preferable to use an active ingredient of a pharmaceutical product, and it is preferable to use a known pharmaceutically active ingredient or pharmaceutically active ingredient candidate compound, which has a hydroxyl group and/or an amino group. Furthermore, as the physiologically active substance with a hydroxyl group and/or an amino group, any substance including a known pharmaceutically active ingredient or a pharmaceutically active ingredient candidate compound may be applied without any particular limitations. That is, by converting the pharmaceutically active ingredient or a candidate compound thereof into a derivative or a prodrug and introducing a hydroxyl group and/or an amino group, the pharmaceutically active ingredient or a candidate compound thereof may be applied as the physiologically active substance with a hydroxyl group and/or an amino group.

Since the block copolymer of the present invention has a feature of having enhanced tissue-penetrating performance, it is preferable to use the block copolymer for the treatment of local tissue diseases. Examples of such diseases include malignant tumor diseases, inflammatory diseases, infectious diseases, and the like. Therefore, regarding the physiologically active substance according to the present invention, it is preferable to apply an active ingredient for a pharmaceutical product that is used for the treatment of these diseases.

Examples of the physiologically active substance that is used for malignant tumor diseases include, but not limited to, camptothecin derivatives such as 7-ethyl-10-hydroxycamptothecin, irinotecan, nogitecan, and 9-aminocamptothecin; taxane derivatives such as paclitaxel, docetaxel, and cabazitaxel; anthracycline derivatives such as doxorubicin, epirubicin, amrubicin, daunorubicin, idarubicin, and pirarubicin; rapamycin derivatives such as sirolimus, everolimus, and temsirolimus; cytidine-based antimetabolites such as gemcitabin, cytosine arabinoside, enocitabine, cytarabine ocfosfate, ethynylcytidine, azacytidine, and decitabine; folic acid antimetabolites such as methotrexate, pemetrexed, levofolinate, and folinate; purine-based antimetabolites such as fludarabine, nelarabine, pentostatin, and cladribine; fluorinated pyrimidine-based antimetabolites such as doxifluridine, capecitabine, tegafur, fluorouracil, and carmofur; platinum-containing compounds such as cisplatin, carboplatin, oxaliplatin, and nedaplatin; resorcinol derivatives having HSP90 inhibiting activity, such as ganetespib and luminespib; mitomycin derivatives such as mitomycin C; bleomycin derivatives such as bleomycin and libromycin; vinca alkaloid derivatives such as vincristine, vinblastine, vindesine, and vinorelbine; podophyllotoxin derivatives such as etoposide and teniposide; halichondrin derivatives such as eribulin; staurosporine derivatives such as rebeccamycin and UCN-01; thalidomide derivatives such as lenalidomide and pomalidomide; vitamin A derivatives such as tretinoin and tamibarotene; proteasome inhibitors such as bortezomib, carfilzomib, and ixazomib; combretastatin derivatives such as combretastatin A4; MEK inhibitors such as binimetinib, cobimetinib, and trametinib; CDK inhibitors such as dinaciclib, flavopiridol, and palbociclib; Raf kinase inhibitors such as dabrafenib, sorafenib, and vemurafenib; HDAC inhibitors such as vorinostat, belinostat, panabinostat, and romidepsin; actin polymerization inhibitors such as cytochalasin, latrunculin, and phalloidin; PARP inhibitors such as veliparib, rucaparib, and olaparib; tyrosine kinase inhibitors such as crizotinib, imatinib, gefitinib, erlotinib, afatinib, dasatinib, bosutinib, vandetanib, sunitinib, axitinib, pazopanib, lenvatinib, lapatinib, nintedanib, nilotinib, ceritinib, alectinib, ruxolitinib, crizotinib, and ibrutinib; nitrogen mustard-based alkylating agents such as bendamustine, cyclophosphamide, ifosfamide, busulfan, and melphalan; nitrosourea-based alkylating agents such as nimustine, ranimustine, and lomustine; alkylating agents such as dacarbazine, temozolomide, procarbazine, and thiotepa; aromatase inhibitors such as anastrozole, exemestane, letrozole, and fadrozole; antiandrogen derivatives such as hydroxyflutamide, flutamide, bicalutamide, and enzalutamide; CYP17 (lyase) inhibitors such as abiraterone; antiestrogen agents such as tamoxifen and toremifene; and hormone agents such as estramustine, progesterone, mitotane, and medroxyprogesterone.

Examples of the physiologically active substance that is used for inflammatory diseases include, but not limited to, tacrolimus derivatives such as tacrolimus; steroid derivatives such as dexamethasone and prednisolone; rapamycin derivatives such as sirolimus, everolimus, and temsirolimus; immunosuppressants such as cyclosporine, fingolimod, azathioprine, mizoribine, mycophenolate mofetil, and gusperimus; and NSAIDs such as diflunisal and tiaramide.

Examples of the physiologically active substance that is used for infectious diseases include, but not limited to, antifungal agents, such as polyene-based antibiotic substances such as amphotericin B and nystatin, azole-based derivatives such as fluconazole and voriconazole, candin-based derivatives such as micafungin, and pyrimidine derivatives such as flucytosine; antiviral agents such as acyclovir, valacyclovir, and ganciclovir; and antiviral agents such as zanamivir, oseltamivir, and laninamivir.

The present invention is a technology related to the use of a block copolymer as a physiologically active substance carrier, and is a highly usable technology that may be applied to all substances without being particularly affected by the pharmacological activity function or the chemical structure and physical properties of the physiologically active substance used. Therefore, the present invention is not intended to be limited to these physiologically active substances that are applied to the treatment of diseases, and may be applied to any substance as long as the substance is a physiologically active substance having a bond-forming hydroxyl group and/or amino group.

Regarding the physiologically active substance with a hydroxyl group and/or an amino group according to the present invention, it is more preferable that the physiologically active substance is a known pharmaceutically active ingredient or a pharmaceutically active ingredient candidate compound, which has a hydroxyl group and/or an amino group, without being converted to a derivative or a prodrug.

Examples of the physiologically active substance that is used for malignant tumor diseases include, but not limited to, camptothecin derivatives such as 7-ethyl-10-hydroxycamptothecin, irinotecan, nogitecan, and 9-aminocamptothecin; taxane derivatives such as paclitaxel, docetaxel, and cabazitaxel; anthracycline derivatives such as doxorubicin, epirubicin, amrubicin, daunorubicin, idarubicin, and pirarubicin; rapamycin derivatives such as sirolimus, everolimus, and temsirolimus; cytidine-based antimetabolites such as gemcitabin, cytosine arabinoside, enocitabine, cytarabine ocfosfate, ethynylcytidine, azacytidine, and decitabine; folic acid antimetabolites such as methotrexate, pemetrexed, levofolinate, and folinate; purine-based antimetabolites such as fludarabine, nelarabine, pentostatin, and cladribine; fluorinated pyrimidine-based antimetabolites such as doxifluridine and capecitabine; platinum-containing compounds such as cisplatin, carboplatin, oxaliplatin, and nedaplatin; resorcinol derivatives having HSP90 inhibiting activity, such as ganetespib and luminespib; mitomycin derivatives such as mitomycin C; bleomycin derivatives such as bleomycin and libromycin; vinca alkaloid derivatives such as vincristine, vinblastine, vindesine, and vinorelbine; podophyllotoxin derivatives such as etoposide and teniposide; halichondrin derivatives such as eribulin; staurosporine derivatives such as rebeccamycin and UCN-01; thalidomide derivatives such as lenalidomide and pomalidomide; vitamin A derivatives such as tretinoin; proteasome inhibitors such as bortezomib, carfilzomib, and ixazomib; combretastatin derivatives such as combretastatin A4; MEK inhibitors such as binimetinib and cobimetinib; CDK inhibitors such as dinaciclib and flavopiridol; Raf kinase inhibitors such as dabrafenib; HDAC inhibitors such as vorinostat, belinostat, and panabinostat; actin polymerization inhibitors such as cytochalasin, latrunculin, and phalloidin; tyrosine kinase inhibitors such as bosutinib, crizotinib, and ibrutinib; nitrogen mustard-based alkylating agents such as melphalan; nitrosourea-based alkylating agents such as nimustine and ranimustine; alkylating agents such as dacarbazine and procarbazine; CYP17 (lyase) inhibitors such as antiandrogen agents such as hydroxyflutamide and bicalutamide; antiestrogen agents such as tamoxifen; and hormone agents such as estramustine.

Examples of the physiologically active substance that is used for inflammatory diseases include, but not limited to, tacrolimus derivatives such as tacrolimus; steroid derivatives such as dexamethasone and prednisolone; rapamycin derivatives such as sirolimus, everolimus, and temsirolimus; immunosuppressants such as cyclosporine, fingolimod, azathioprine, mizoribine, mycophenolate mofetil, and gusperimus; and NSAIDs such as diflunisal and tiaramide.

Examples of the physiologically active substance that is used for infectious diseases include, but not limited to, antifungal agents, such as polyene-based antibiotic substances such as amphotericin B and nystatin, azole-based derivatives such as fluconazole and voriconazole, candin-based derivatives such as micafungin, and pyrimidine derivatives such as flucytosine; antiviral agents such as acyclovir, valacyclovir, and ganciclovir; and antiviral agents such as zanamivir, oseltamivir, and laninamivir.

The present invention has enhanced properties of migrating and penetrating into a target diseased tissue, and has a performance of enhanced excretability through the kidneys and the like. Therefore, sensitization of the physiologically active substance to a normal tissue other than a target diseased tissue is suppressed, and an effect of reducing adverse effects is provided. Therefore, it is preferable to apply a physiologically active substance that is used for a disease having a problem of reducing adverse effects in normal tissues. Examples of such a disease include malignant tumor diseases and inflammatory diseases. Therefore, as the physiologically active substance used in the present invention, it is preferable to use an antitumor agent against a malignant tumor disease. Also, it is preferable to use a physiologically active substance against an inflammatory disease.

Regarding the physiologically active substance that is used for malignant tumor diseases, the above-mentioned camptothecin derivatives, taxane derivatives, resorcinol derivatives, anthracycline derivatives, rapamycin derivatives, cytidine-based antimetabolites, folic acid antimetabolites, purine-based antimetabolites, fluorinated pyrimidine-based antimetabolites, platinum-containing compounds, mitomycin derivatives, bleomycin derivatives, vinca alkaloid derivatives, podophyllotoxin derivatives, halichondrin derivatives, staurosporine derivatives, thalidomide derivatives, vitamin A derivatives, proteasome inhibitors, combretastatin derivatives, MEK inhibitors, CDK inhibitors, Raf kinase inhibitors, HDAC inhibitors, actin polymerization inhibitors, PARP inhibitors, tyrosine kinase inhibitors, nitrogen mustard-based alkylating agents, nitrosourea-based alkylating agents, alkylating agents, derivatives of aromatase inhibitors, antiandrogen agents, CYP17 (lyase) inhibitors, antiestrogen inhibitors, and hormone agents are preferred.

Camptothecin derivatives, taxane derivatives, resorcinol derivatives, anthracycline derivatives, rapamycin derivatives, cytidine-based antimetabolites, folic acid antimetabolites, and the like are more preferred. Particularly preferably, camptothecin derivatives, taxane derivatives, resorcinol derivatives, rapamycin derivatives, and the like are preferred.

As the physiologically active substance that is used for inflammatory diseases, the above-mentioned tacrolimus derivatives, steroid derivatives, rapamycin derivatives, immunosuppressants, NSAIDs, and the like are preferred, and tacrolimus derivatives, steroid derivatives, and rapamycin derivatives are particularly preferred.

The physiologically active substance of $R_3$ is such that identical compounds may exist in the same molecule of the physiologically active substance-conjugated block copolymer, or plural kinds of compounds may exist as a mixture. It is preferable that $R_3$'s represent identical compounds.

In General Formula (1), n represents 1 or 2. When n is 1, the amino acid that constitutes the polyamino acid derivative segment is aspartic acid. Meanwhile, when n is 2, the amino acid that constitutes the polyamino acid derivative segment is glutamic acid. Therefore, the polyamino acid derivative segment for General Formula (1) a polyaspartic acid segment, a polyglutamic acid, or a poly(mixed aspartic acid-glutamic acid) segment.

B in General Formula (1) is a linking group of a residue of the physiologically active substance with a hydroxyl group and/or an amino group of $R_3$ and a side chain carboxyl group of an aspartic acid unit and/or a glutamic acid unit.

The linking group of B is a linking group that forms an ester bond and/or an amide bond with a hydroxyl group and/or an amino group of the physiologically active substance, and forms an ester bond, an amide bond, or a thioester bond with the side chain carboxyl group of the aspartic acid unit and/or glutamic acid unit. Examples include, but not limited to, —CO—$(CH_2)_x$—O— (wherein x represents an integer of 1 to 8), —CO—$(CH_2)_x$—NH— (wherein x represents an integer of 1 to 8), and —CO—$(CH_2)_x$—S— (wherein x represents an integer of 1 to 8).

An amino acid derivative may be used as the linking group of B. The embodiment of using the linking group in the case of using an amino acid derivative as a linking group, is an embodiment in which a N-terminal amino group of the amino acid derivative forms an amide bond with the side chain carboxyl group, and a C-terminal carboxyl group forms an ester bond or an amide bond with a hydroxyl group and/or an amino group of the physiologically active substance.

In a case in which an amino acid derivative is used as the linking group of B, any one of a naturally occurring amino acid or a synthetic amino acid and a side chain-modified form thereof may be used. Any one of the L-form, the D-form, and a racemate may also be used. Examples thereof may include, but not limited to, glycine, alanine, β-alanine, leucine, phenylalanine, serine, threonine, tyrosine, aspartic acid, glutamic acid, lysine, arginine, histidine, ornithine, and cysteine. Examples of the amino acid having a modified side chain include, but not limited to, an alkyl ester of aspartic acid or glutamic acid, an aralkyl ester of aspartic acid or glutamic acid, an alkylamide of aspartic acid or glutamic acid, an aralkylamide of aspartic acid or glutamic acid, and an alkyloxycarbonyl lysine such as Boc-lysine.

A glycolic acid derivative that arranges a hydroxyl group and a carboxyl group via a methylene group as the linking group, may also be used. The embodiment of using a linking group in a case in which glycolic acid derivative as a linking group is an embodiment in which a hydroxyl group of the glycolic acid derivative forms an ester bond with the side chain carboxyl group, and a carboxyl group forms an ester bond or an amide bond with a hydroxyl group and/or an amino group of the physiologically active substance.

Examples of the glycolic acid derivative include, but not limited to, glycolic acid, lactic acid, malic acid, tartaric acid, and citric acid. In the case of using a polyvalent carboxylic acid, the glycolic acid derivative is preferably such that the physiologically active substance is linked to one of the carboxylic acid groups, and the other carboxyl group is an ester derivative or an amide derivative.

The linking groups may be linking groups of a single kind, or plural kinds of linking groups may exist as a mixture.

Furthermore, B is desirably a "bond". The term "bond" refers to an embodiment in which the side chain carboxyl group of the aspartic acid unit and/or glutamic acid unit is directly linked to a hydroxyl group and/or an amino group of the physiologically active substance via an ester bond or an amide bond, particularly without involving a linking group.

$R_4$'s in General Formula (1) represent one or more substituents selected from the group consisting of a linear, branched or cyclic C1-C30 alkoxy group which may have a substituent, a linear, branched or cyclic C1-C30 alkylamino group which may have a substituent, a linear, branched or cyclic C1-C30 dialkylamino group which may have a substituent, a C1-C8 alkyaminocarbonyl-C1-C8 alkylamino group which may have a substituent, a residue of a hydrophobic fluorescent substance, and a hydroxyl group.

For this $R_4$, any group may be arbitrarily introduced for the purpose of controlling the physical properties of the present physiologically active substance-conjugated block copolymer. For example, by introducing a hydrophobic group into $R_4$, hydrophobicity of the poly(aspartic acid and/or glutamic acid) segment of the physiologically active substance-conjugated block copolymer may be increased. On the other hand, when a hydrophilic substituent including an ionic functional group capable of forming a salt, such as an amino group, a carboxyl group or a hydroxyl group, is introduced as $R_4$, hydrophilicity of the polyglutamic acid segment of the physiologically active substance-conjugated block copolymer may be increased. In a case in which $R_4$ is a hydroxyl group, the side chain carboxyl group of the poly(aspartic acid and/or glutamic acid) segment is a free carboxylic acid.

The substituents for $R_4$ may be substituents of a single kind, or may be substituents of plural kinds.

The linear, branched or cyclic C1-C30 alkoxy group which may have a substituent for $R_4$ is an alkoxy group in which an ester type modifying group is linked to a side chain carboxyl group of the poly(aspartic acid and/or glutamic acid) segment. The alkoxy group may have a hydroxyl group, a halogen atom, an amino group, an alkylamino group, a dialkylamino group, an alkoxy group, an aryl group, or the like as the substituent. Examples of the C1-C30 alkoxy group for $R_4$ include, but not limited to, a methoxy group, an ethoxy group, a 1-propyloxy group, an isopropyloxy group, a n-butoxy group, a t-butoxy group, a cyclohexyloxy group, a benzyloxy group, a 4-phenylbutyloxy group, a n-octyloxy group, a decyloxy group, a dodecyloxy group, a tetradecyloxy group, a hexadecyloxy group, an octadecyloxy group, an eicosyloxy group, a docosyloxy group, a tetracosyloxy group, a hexacosyloxy group, an octacosyloxy group, and a triacontyloxy group.

The linear, branched or cyclic C1-C30 alkylamino group which may have a substituent for $R_4$ is an alkylamino group in which an alkylamide type modifying group is linked to a side chain carboxyl group of the poly(aspartic acid and/or glutamic acid) segment. The alkylamino group may include a hydroxyl group, a halogen atom, an amino group, an alkylamino group, a dialkylamino group, an alkoxy group, an aryl group, or the like as the substituent. Examples of the C1-C30 alkylamino group for $R_4$ include, but not limited to, a methylamino group, an ethylamino group, a propylamino group, an isopropylamino group, a butylamino group, a t-butylamino group, a cyclohexylamino group, a benzylamino group, a 4-phenylbutylamino group, an octylamino group, a decylamino group, a dodecylamino group, a tetradecylamino group, a hexadecylamino group, an octadecylamino group, an eicosylamino group, a docosylamino group, a tetracosylamino group, a hexacosylamino group, an octacosylamino group, and a triacontylamino group.

Furthermore, an amino acid having a protected carboxyl group is included in the C1-C30 alkylamino group which may have a substituent. As the amino acid having a protected carboxyl group, for example, glycerin methyl ester, glycine benzyl ester, β-alanine methyl ester, β-alanine benzyl ester, alanine methyl ester, leucine methyl ester, and phenylalanine methyl ester may also be used.

The linear, branched or cyclic C1-C30 dialkylamino group which may have a substituent for $R_4$ is a dialkylamino group in which a side chain carboxyl group of the poly(aspartic acid and/or glutamic acid) segment is linked to a dialkylamide type modifying group. As the substituent, the dialkylamino group may include a hydroxyl group, a halogen atom, an amino group, an alkylamino group, a dialkylamino group, an alkoxy group, an aryl group, or the like. Examples of the di-C1-C30 alkylamino group for $R_4$ include, but not limited to, a dimethylamino group, a diethylamino group, a dipropylamino group, a diisopropylamino group, a dibutylamino group, a pyrrolidino group, a piperidino group, a dibenzylamino group, a N-benzyl-N-methylamino group, a dioctylamino group, a dinonylamino group, a didecylamino group, a didodecylamino group, a dietradecylamino group, a dihexadecylamino group, a dioctadecylamino group, and a dieicosylamino group.

The C1-C8 alkylaminocarbonyl-C1-C8 alkylamino group which may have a substituent for $R_4$ is a group in which a side chain carboxyl group of the poly(aspartic acid and/or glutamic acid) segment is linked to a urea type modifying group. The alkyl groups may be of the same kind, or may be of different kinds. As the substituent, the group may include a hydroxyl group, a halogen atom, an amino group, an alkylamino group, a dialkylamino group, an alkoxy group, an aryl group, or the like. In the case of having a substituent, a dialkylamino group is preferred. Examples of the C1-C8 alkylaminocarbonyl-C1-C8 alkylamino group which may have a substituent include, but not limited to, a methylaminocarbonylmethylamino group, an ethylaminocarboylethylamino group, an isopropylaminocarbonylisopropylamino group, a cyclohexylaminocarbonylcyclohexylamino group, an ethylaminocarbonyl-(3-dimethylaminopropyl)amino group, and a (3-dimethylaminopropyl)aminocarbonylethylamino group.

$R_4$ is desirably a residue of a fluorescent substance. Regarding the fluorescent substance, it is preferable to use a fluorescent substance with a hydroxyl group and/or an amino group for linking to a side chain carboxyl group of an aspartic acid unit and/or a glutamic acid unit. Therefore, in a case in which $R_4$ represents a residue of a fluorescent substance, this refers to a residue of a fluorescent substance in which a hydrogen atom has been removed from the hydroxyl group and/or amino group.

The fluorescent substance is preferably a fluorescent substance having an amino group, and examples thereof include, but not limited to, 2-(2-aminoethoxy)-9-(diethylamino)-5H-benzo[a]phenoxazin-5-one, BODIPY (registered trademark) TR Cadaverine, BODIPY (registered trademark) FL Ethylenediamine, ALEXA FLUOR (registered trademark) 594 Cadaverine, TEXAS RED (registered trademark) Cadaverine, and ATTO 594 amine. Therefore, the residue of a fluorescent substance of $R_4$ includes such a residue after amide bonding.

$R_4$ in General Formula (1) may be a hydroxyl group. That is, the side chain carboxylic acid of the poly(aspartic acid and/or glutamic acid) segment is a free carboxylic acid. In this case, the side chain carboxylic acid may be in the form of free acid, or may be in the form of any pharmaceutically acceptable carboxylic acid salt. Examples of the carboxylic acid salt include, but not limited to, a lithium salt, a sodium salt, a potassium salt, a magnesium salt, a calcium salt, and an ammonium salt, which are included in the present invention.

In General Formula (1), $x_1$, $x_2$, $y_1$, $y_2$, and $z$ each represent the content of a constituent unit of an aspartic acid derivative unit and/or a glutamic acid derivative unit in the poly (aspartic acid and/or glutamic acid) segment of the block copolymer, and each represent an integer of 0 to 25. Furthermore, $(x_1+x_2+y_1+y_2+z)$ represents the number of polymerized units of the poly(aspartic acid and/or glutamic acid) segment, and is an integer of 3 to 25. That is, it is implied that the poly(aspartic acid and/or glutamic acid) segment is a polymer having an average number of polymerized units of 3 to 25. If the value of $(x_1+x_2+y_1+y_2+z)$ is smaller than 3, the block copolymer thus obtainable does not have self-associating properties, and there is a risk that the laser light scattering intensity may not fall in an optimal range. On the other hand, if the number of polymerized units is larger than 25, there is a possibility that the molecular weight of the physiologically active substance-conjugated block copolymer thus obtainable may exceed 15 kilodaltons, and there is a risk that desired pharmacokinetics may not be presented. That is, if the value of $(x_1+x_2+y_1+y_2+z)$, which is the number of polymerized units of the poly(aspartic acid and/or glutamic acid) segment, is not in the range of 3 to 25, there is a risk that the action of enhancing the pharmacological action effect of the physiologically active substance and an effect of reducing adverse effects may not be obtained. It is preferable that the number of polymerized units of the polyamino acid derivative is appropriately set in consideration of the molecular weight of the physiologically active substance-conjugated block copolymer. The value of $(x_1+x_2+y_1+y_2+z)$ is preferably an integer of 5 to 20.

The value of $(x_1+x_2+y_1+y_2+z)$, which is the number of polymerized units of the polyamino acid derivative, may be determined by performing an analysis by $^1$H-NMR, or performing neutralization titration on the polyethylene glycol-poly(aspartic acid and/or glutamic acid) block copolymer before $R_3$ and $R_4$ are linked thereto.

In General Formula (1), $(x_1+x_2)$ represents the total number of aspartic acid units and/or glutamic acid units conjugated with the physiologically active substance of $R_3$. It is an essential configuration to have the units conjugated with the physiologically active substance, and this $(x_1+x_2)$ is an integer of 1 to 25. Preferably, this $(x_1+x_2)$ is an integer of 2 to 20, and more preferably an integer of 3 to 15. The proportion of $(x_1+x_2)$ with respect to $(x_1+x_2+y_1+y_2+z)$, which is the number of polymerized units of the poly (aspartic acid and/or glutamic acid) derivative segment, is 4% to 100%, preferably 10% to 90%, and more preferably 20% to 80%.

The number of the contained physiologically active substance-conjugated aspartic acid units and/or glutamic acid units of $(x_1+x_2)$, is calculated from the amount of the physiologically active substance conjugated thereto and the number of polymerized units of the poly(aspartic acid and/or glutamic acid) segment. The amount of the physiologically active substance conjugated thereto may be determined by a method of cleaving the physiologically active substance from the physiologically active substance-conjugated block copolymer, and quantitatively analyzing the released physiologically active substance. Furthermore, a method of calculating the amount from the reaction ratio of the physiologically active substance at the time of producing the physiologically active substance-conjugated block copolymer may also be used.

In General Formula (1), $(y_1+y_2)$ represents the total number of aspartic acid units and/or glutamic acid units to which $R_4$ is linked. Furthermore, z represents the total number of aspartic acid units and/or glutamic acid units having a structure in which the side chain carboxyl group has been intramolecularly cyclized. These are optional configurations, and $(y_1+y_2)$ and z are each an integer of 0 to 24. Preferably, these $(y_1+y_2)$ and z are each an integer of 1 to 20. The proportion of $(y_1+y_2+z)$ with respect to $(x_1+x_2+y_1+y_2+z)$, which is the number of polymerized units of the poly (aspartic acid and/or glutamic acid) derivative segment, is 0% to 96%, and preferably 4% to 90%.

The number of the included aspartic acid units and/or glutamic acid units to which $R_4$ is linked, which is related to $(y_1+y_2)$, is calculated from the amount to which substituents of $R_4$ is linked to and the number of polymerized units of the poly(aspartic acid and/or glutamic acid) segment. The amount to which substituents of $R_4$ is linked to may be determined by a method of cleaving the substituent of $R_4$ from the block copolymer and quantitatively analyzing the released physiologically active substance. A method of calculating the amount from the reaction ratio of the substituent of $R_4$ at the time of producing the block copolymer may also be used. The amount may also be calculated from the integral values of $^1$H-NMR.

In regard to the physiologically active substance-conjugated block copolymer according to the present invention, the poly(aspartic acid and/or glutamic acid) segment is a polymer segment which includes a mixture of an aspartic acid unit and/or glutamic acid unit having $R_3$ at a side chain carboxyl group, an aspartic acid unit and/or glutamic acid unit having $R_4$, and an aspartic acid unit and/or glutamic acid unit having a structure in which side chain carboxyl groups are intramolecularly cyclized. The segment structure is a segment structure in which one or more units exist for each of the constituent units, arrangement thereof is not particularly limited, and the constituent units are randomly and irregularly arranged.

The physiologically active substance-conjugated block copolymer represented by General Formula (1) is preferably such that the mass content of the physiologically active substance represented by $R_2$ is from 10% by mass to 60% by mass. If the content of the physiologically active substance is smaller than 10% by mass, there is a risk that the content of the physiologically active substance may be small, and a pharmacological activity effect may not be sufficiently provided. On the other hand, if the content of the physiologically active substance is larger than 60% by mass, there is a risk that the hydrophilicity-hydrophobicity balance of the physiologically active substance-conjugated block copolymer may significantly change, and the block copolymer may not have appropriate self-associating properties and may not present the desired pharmacokinetics. The mass content of the physiologically active substance is preferably from 10% by mass to 50% by mass, and even more preferably from 10% by mass to 40% by mass.

The block copolymer represented by General Formula (1) has a feature that the molecular weight is from 2 kilodaltons to 15 kilodaltons. Regarding the molecular weight of the block copolymer, a calculated value obtained by summing the respective constituent molecular weight of each constituent part is employed as the molecular weight of the block copolymer. That is, a calculated value obtained by summing: (1) the molecular weight of the polyethylene glycol segment; (2) the molecular weight of the main chain part of the polyamino acid derivative segment; (3) the total molecular weight of the physiologically active substance obtained by multiplying the molecular weight of the residue of the physiologically active substance by the number of bonds thereof; and (4) the total molecular weight of substituents other than the physiologically active substance obtained by multiplying the molecular weight of residues of the substituents by the number of bonds thereof, is employed as the molecular weight.

The molecular weight of the block copolymer may be a molecular weight defined with an accuracy of the unit of kilodaltons. Therefore, the method for analyzing the each constituent part is not particularly limited as long as it is an analysis method with sufficient accuracy for the measurement of the molecular weight of the polyamino acid derivative to the unit of kilodaltons, and various analysis methods may be selected as appropriate. Preferable analysis methods for the each constituent part will be described below.

The molecular weight of the polyethylene glycol segment in the above (1) is a measured value of the molecular weight of the polyethylene glycol compound that constitutes the polyethylene glycol segment, and an average molecular weight that may be determined by the peak top molecular weight measured by a GPC method based on polyethylene glycol standard products is employed.

The molecular weight of the main chain part of the polyamino acid derivative segment in the above (2) is a calculated value obtained by multiplying the molecular weight of the polymerized monomer unit of the segment by the average number of polymerized units. In regard to the number of polymerized unit, it is preferable to use a number of polymerized units calculated by a method of quantitatively determining the side chain carboxyl groups of the polyamino acid by neutralization titration, or a number of polymerized units calculated from the integral values of $^1$H-NMR. It is preferable to use a neutralization titration method.

The total molecular weight of the physiologically active substance in the above (3) is a calculated value obtained by multiplying the molecular weight of the physiologically active substance by the number of polymerized units. The number of polymerized units may be determined by a method of calculating the number of polymerized units from weight measurement of an unreacted portion of the physiologically active substance in the reaction liquid by HPLC, or by a method of cleaving the physiologically active substance from the physiologically active substance-conjugated block copolymer, and quantitatively analyzing the released physiologically active substance or fragment molecules originating therefrom.

The total molecular weight of substituents other than the physiologically active substance in the above (4) is a calculated value obtained by multiplying the molecular weight of the residues of the substituents by the number of the bonds thereof. The number of bonds of the substituents may be determined by a method of measuring and calculating unreacted residues in the reaction liquid by HPLC, or by a quantitative analysis after hydrolysis from polyamino acid. The number of polymerized units may also be calculated from the integral values of $^1$H-NMR.

The present block copolymer has a molecular weight of from 2 kilodaltons to 15 kilodaltons. When the molecular weight is smaller than 2 kilodaltons, this implies that the physiologically active substance-conjugated block copolymer does not have a sufficient nanoparticle-forming ability, and sufficient penetrating performance into a target tissue is not obtained. Therefore, the pharmacological action effect of the physiologically active substance may not be efficiently manifested. On the other hand, when the molecular weight is larger than 15 kilodaltons, the block copolymer has suppressed kidney excretability, and thus, retention in vivo is enhanced. Accordingly, sensitization of the physiologically active substance to normal tissues other than a target diseased tissue may occur, and therefore, there is a risk that normal tissues may exhibit disorders. For example, when a cytotoxic physiologically active substance is used, persistence of blood toxicity associated with myelopathy may be considered. Therefore, it is necessary to control the molecular weight to be 15 kilodaltons or less. The molecular weight of the block copolymer is preferably from 3 kilodaltons to 12 kilodaltons, and more preferably from 3 kilodaltons to 10 kilodaltons.

The physiologically active substance-conjugated block copolymer represented by General Formula (1) has a property of exhibiting self-association in an aqueous solution. That is, the physiologically active substance-conjugated block copolymer has a property in which when a 1 mg/mL aqueous solution of the physiologically active substance-conjugated block copolymer is subjected to a particle size distribution analysis based on a dynamic light scattering method using laser light, the physiologically active substance-conjugated block copolymer is measured as nanoparticles having a volume average particle diameter of about a few nanometers to about 20 nanometers. It is preferable that the present physiologically active substance-conjugated block copolymer has a property in which the block copolymer forms nanoparticles having a particle size of less than 20 nanometers at the maximum in a 1 mg/mL aqueous solution. In this case, a particle size distribution analysis in an aqueous solution based on pure water is employed. Preferably, the physiologically active substance-conjugated block copolymer is characterized in that the volume average particle diameter is measured to be less than 20 nanometers by a particle size distribution analysis method based on a dynamic light scattering method using laser light, and more preferably, the block copolymer has a property in which the block copolymer is analyzed as nanoparticles having a particle size of 3 to 15 nanometers.

The volume average particle diameter according to the present invention is the particle size of the peak that exists at the largest proportion in a volume distribution that may be measured with, for example, a ZetaPotential/Particlesizer NICOMP 380 ZLS (analysis method: NICOMP method) manufactured by Particle Sizing Systems, LLC, or a particle size zeta potential analyzer, ZETASIZER NANO ZS (analysis method: NNLS method) manufactured by Malvern Instruments, Ltd.

Since the physiologically active substance-conjugated block copolymer represented by General Formula (1) is a block copolymer in which a hydrophilic polyethylene glycol segment is connected with a polyamino acid derivative segment that exhibits hydrophobicity by means of a physiologically active substance or another hydrophobic side chain, it is considered that in an aqueous solution, the polyamino acid derivative segments of a plurality of the block copolymer molecules associate with one another based on the hydrophobic interaction of the polyamino acid derivative segment. Consequently, it is speculated that micelle-like associated bodies having a core-shell structure are formed, in which the polyamino acid derivative segment forms an inner core (core part) and the hydrophilic polyethylene glycol segment covers the periphery of the inner core and forms an outer shell layer (shell part), and these are observed as the nanoparticle described above.

The physiologically active substance-conjugated block copolymer represented by General Formula (1) needs to have a property of forming nanoparticles in an aqueous solution, for the purpose of enhancing the pharmacological action effect of the physiologically active substance and/or reducing adverse effects.

It is effective to use the light scattering intensity obtained by using laser light, as an index for the nanoparticle-forming properties of the block copolymer conjugated with a physiologically active substance. That is, the nanoparticle-forming properties of the physiologically active substance-conjugated block copolymer in an aqueous solution may be checked by utilizing the laser light scattering intensity as an index. In that case, a method of checking the nanoparticle-forming properties of the physiologically active substance-conjugated block copolymer in an aqueous solution by using toluene as a light scattering intensity standard sample, and utilizing the relative intensity with respect to toluene as an index, is effective.

The present block copolymer conjugated with a physiologically active substance is such that the laser light scattering intensity in a 1 mg/mL aqueous solution of the block copolymer is at least twice or more as a relative intensity with respect to the light scattering intensity of toluene.

If the relative light scattering intensity is smaller than twice, it is implied that the physiologically active substance-conjugated block copolymer does not have sufficient nanoparticle-forming properties, and sufficient penetrating performance into a target tissue is not obtained. Therefore, the pharmacological action effect of the physiologically active substance may not be efficiently exhibited. According to the present invention, the value of the relative light scattering intensity is an index indicating that the block copolymer has a nanoparticle-forming ability, and any value is acceptable as long as it is twice the light scattering intensity of toluene, without any particular limitations. That is, even if the relative light scattering intensity is higher than 100 times, it may be said that the block copolymer has a sufficient nanopaticle-forming ability. However, if the light scattering intensity is higher than 100 times, it may be considered that there is a possibility that the block copolymer may not have desirable excretability. In that case, since the retention in vivo of the block copolymer increases, sensitization of the physiologically active substance to normal tissues other than a target diseased tissue may occur, and therefore, there is a risk that normal tissues may exhibit disorders. Therefore, it is appropriate to control the relative light scattering intensity to be 100 times or less.

The present physiologically active substance-conjugated block copolymer is such that the light scattering intensity of an aqueous solution thereof is preferably 2 times to 50 times, and more preferably from 2 times to 30 times, as a relative intensity with respect to the light scattering intensity of toluene.

In regard to the method for measuring the light scattering intensity obtained by using laser light for the analysis of the nanoparticle-forming properties of the present physiologically active substance-conjugated block copolymer, a method of using a 1 mg/mL aqueous solution of the physiologically active substance-conjugated block copolymer as a measurement sample, and measuring the light scattering intensity with a laser light scattering photometer at a measurement temperature of 25° C., a scattering angle of 90°, and a wavelength of 632.8 nm is suitable. Examples of the measuring instrument may include, but not limited to, a dynamic light scattering photometer manufactured by Otsuka Electronics Co., Ltd., DLS-8000DL (measurement temperature: 25° C., scattering angle: 900, wavelength: 632.8 nm, ND filter: 2.5%, PH1: OPEN, PH2: SLIT).

The measurement of the light scattering intensity is an analyzed value obtained by using an aqueous solution prepared using pure water that does not include microparticles as an analytic sample. The aqueous solution may be optionally dissolved by means of ultrasonic irradiation during solution preparation. The aqueous solution thus prepared is preferably an aqueous solution that has been further subjected to a filtration treatment in order to remove submicron-sized microparticles.

Regarding toluene that is used as a standard substance for the measurement of light scattering intensity, any toluene may be used without particular limitations as long as the toluene has reagent-level purity. It is preferable to use toluene that has been subjected to pretreatment filtration, which is usually performed for the preparation of a sample for a light scattering analysis.

Next, the method for producing the present block copolymer conjugated with a physiologically active substance will be explained. A method of producing an AB-block copolymer in which the polyethylene glycol segment of the present block copolymer is connected with a polyamino acid segment including aspartic acid and/or glutamic acid, and producing the physiologically active substance-conjugated block copolymer by a condensation reaction between this AB-block copolymer and a physiologically active substance; a method of connecting a polymer component including the polyethylene glycol segment with a polyamino acid derivative linked to a physiologically active substance; and the like may be mentioned. The former method of producing in advance an AB-block copolymer in which a polyethylene glycol segment is connected with a polyamino acid segment, and producing the physiologically active substance-conjugated block copolymer by performing a condensation reaction between this block copolymer and a physiologically active substance, is preferred.

Regarding the method for producing an AB-block copolymer in which a polyethylene glycol segment is connected with a polyamino acid segment, a method of constructing a polyamino acid segment by sequentially polymerizing an amino acid-N-carboxylic acid anhydride with a compound including a polyethylene glycol segment; a method of linking a polyethylene glycol segment to a polyamino acid segment; and the like may be mentioned. For the reason that the block copolymer has high reactivity, and it is easy to control the number of polymerized units of the polyamino acid, it is preferable to use the former method.

An embodiment of the production method for obtaining a block copolymer according to the present invention by producing in advance an AB-block copolymer in which a polyethylene glycol segment is connected with a polyamino acid derivative segment, and linking a physiologically active substance with a hydroxyl group and/or an amino group to the AB-block copolymer, will be described.

First, a polyethylene glycol derivative having an amino group at one end (for example, methoxypolyethylene glycol-1-propylamine) is sequentially reacted with a N-carbonylamino acid anhydride having an appropriately protected side chain functional group of the amino acid, and an AB-block type copolymer skeleton in which the polyethylene glycol segment is connected with the polyamino acid segment is constructed by polymerization in sequence. In this case, aspartic acid and/or glutamic acid may be incorporated into the polyamino acid segment by incorporating N-carbonylaspartic acid anhydride and/or N-carbonylglutamic acid anhydride, both having an appropriate protected side chain carboxyl group, as the N-carbonylamino acid anhydride. Subsequently, the resultant is subjected to an appropriate deprotection reaction, and thus the AB-block copolymer including aspartic acid and/or glutamic acid having a deprotected side chain carboxyl group may be produced. Regarding the deprotection reaction, in a case in which the side chain carboxyl group is a β-benzyl ester, a deprotection reaction may be achieved by hydrolysis under alkaline condition or a hydrogenolysis reaction.

This polyethylene glycol-polyamino acid AB-block copolymer may be reacted with a physiologically active substance having an amino group and/or a hydroxyl group, in an appropriate reaction solvent under condensation reaction conditions.

In regard to the solvent that is used for the condensation reaction between the polyethylene glycol-polyamino acid AB-block copolymer and a physiologically active substance, any solvent may be used without particular limitations as long as it is a solvent in which both the compounds may dissolve. Examples thereof may include, but not limited to, water-soluble organic solvents such as N,N-dimethylformamide (DMF), N-methylpyrrolidone (NMP), and 1,3-dimethyl-2-imidazolidinone (DMI). These solvents may be used singly, or a mixed solvent of these may be used. The solvent may also be a mixed solvent of the above-mentioned solvents and other organic solvents.

Regarding the condensing agent to be used, any conventional dehydration condensing agent that induces an ester reaction between a carboxylic acid and a hydroxyl group by a dehydration condensation reaction, and/or an amidation reaction between a carboxylic acid and an amino group by a dehydration condensation reaction, may be used without any particular problem. Examples of the condensing agent that may be used include, but not limited to, carbodiimide-based condensing agents such as dicyclohexylcarbodiimide (DCC), diisopropylcarbodiimide (DIPCI), and 1-ethyl-3-(3-dimethylaminopropyl)carbodiimide hydrochloride (WSC); triazine-based condensing agents such as 4-(4,6-dimethoxy-1,3,5-triazin-2-yl)-4-methylmorpholium chloride n-hydrate (DMT-MM); 1-ethoxycarbonyl-2-ethoxy-1,2-dihydroquinoline (EEDQ), and di-tert-butyl dicarbonate ($Boc_2O$). At the time of the condensation reaction, a reaction aid such as N,N-dimethylaminopyridine (DMAP), 1-hydroxybenzotriazole (HOBt), or N-hydroxysuccinimide (HOSu) may also be used. When a carbodiimide-based condensing agent is used, a C1-C8 alkylaminocarbonyl-(C1-C8) alkylamino group which may have a substituent may be introduced simultaneously with a physiologically active substance into $R_4$ of General Formula (1).

Regarding the reaction temperature, the reaction may be carried out usually at a temperature of 0° C. to 180° C., and preferably 5° C. to 100° C.

For the purpose of adjusting the self-associating properties of the present physiologically active substance-conjugated copolymer, another hydrophobic substituent such as the C1-C30 alkoxy group, the C1-C30 alkylamino group, or the di-C1-C30 alkylamino group may be incorporated into the polyamino acid segment. Regarding the method, a method of activating carboxyl groups of the polyethylene glycol-polyamino acid copolymer by adding a condensing agent, and then reacting the copolymer with an alcohol compound or an amino compound, which corresponds to the hydrophobic substituent that is wished to be introduced, at desired equivalents; or a method of activating the alcohol compound or the amino compound, and then reacting the activated compound with the polyamino acid segment of the copolymer, may be employed.

In this case, a physiologically active substance may be introduced after a hydrophobic substituent is introduced by means of the alcohol compound or the amino compound, or the introduction may be achieved in a reverse order. The physiologically active substance and the hydrophobic substituent may also be introduced simultaneously.

The hydrophobic substituents may be substituents of a single kind, or may be substituents of plural kinds. In a case in which plural kinds of substituents are introduced, a mixture of various hydrophobic substituents may be synthesized if different alcohol compounds or amino compounds are reacted repeatedly.

After a physiologically active substance and an optional hydrophobic substituent are introduced into the polyethylene glycol-polyamino acid AB-block copolymer, conventional separation operations or purification operations are optionally performed. Thereby, the present physiologically active substance-conjugated block copolymer may be produced.

The present physiologically active substance-conjugated block copolymer has a property of slowly cleaving and releasing the physiologically active substance, after being administered in vivo. The released physiologically active substance is capable of presenting a pharmacological effect. Therefore, the present physiologically active substance-conjugated block copolymer may be used as a pharmaceutical product containing the physiologically active substance as an active ingredient.

When the present physiologically active substance-conjugated block copolymer is used as a pharmaceutical product, the block copolymer may be used via any of peroral route of administration and parenteral route of administration. It is preferable that the physiologically active substance-conjugated block copolymer is formulated to be used for the route of administration by parenteral injection. Administration by injection is carried out by intravenous administration, intra-arterial administration, subcutaneous administration, intramuscular administration, intratumor administration, or the like.

For the formulation of the present physiologically active substance-conjugated block copolymer pharmaceutically acceptable carriers that are conventionally used, for example, a binder, a lubricating agent, a disintegrant, a solvent, an excipient, a solubilizing agent, a dispersant, a stabilizer, a suspending agent, a preservative, a soothing agent, a colorant, and a fragrance may be used.

In the case of an injectable liquid preparation, a solvent is usually used. Examples of the solvent include, but not limited to, water, physiological saline, a 5% glucose or mannitol solution; water-soluble organic solvents such as, for example, glycerol, ethanol, dimethyl sulfoxide, N-methylpyrrolidone, polyethylene glycol, and a chromophore, and mixed liquids thereof; and mixed liquids of water and the water-soluble organic solvents. It is preferable that the physiologically active substance-conjugated block copolymer is used after being prepared into an administrable pharmaceutical preparation using these additives for formulation.

The dose of the present physiologically active substance-conjugated block copolymer may be definitely varied depending on the kind of the physiologically active substance to be conjugated, the age, gender, physiological condition, and disease condition of the patient, or the like. However, it is preferable to administer the physiologically active substance-conjugated block copolymer parenterally, usually at a dose of 0.01 to 500 $mg/m^2$, and preferably 0.1 to 250 $mg/m^2$, in terms of the active ingredient, per day for an adult.

A preferred embodiment of the present invention may be the above-described block copolymer that uses a camptothecin derivative, which is an antitumor agent, as the physiologically active substance. A camptothecin derivative-conjugated block copolymer that uses a camptothecin derivative as the physiologically active substance will be explained below.

The camptothecin derivative is, for example, a camptothecin derivative such as 7-ethyl-10-hydroxycamptothecin, irinotecan, or nogitecan. These camptothecin derivatives have a hydroxyl group at the 20-position of the camptothecin skeleton. Furthermore, 7-ethyl-10-hydroxycamptothecin and nogitecan have a hydroxyl group at the 10-position.

This hydroxyl group at the 10-position and/or the 20-position forms an ester bond with the side chain carboxyl group of aspartic acid and/or glutamic acid directly or by using an appropriate linking group.

Regarding the camptothecin derivative, a camptothecin derivative represented by General Formula (2) is preferably used:

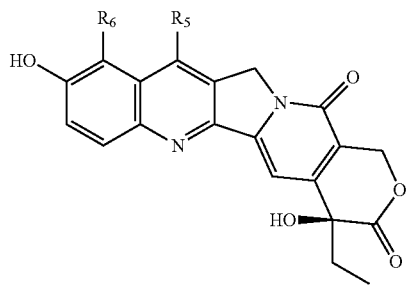

(2)

wherein $R_5$ represents a substituent selected from the group consisting of a hydrogen atom, a C1-C6 alkyl group which may have a substituent, and a silyl group which may have a substituent; and $R_6$ represents a hydrogen atom, or a C1-C6 alkyl group which may have a substituent.

The bonding mode of the residue according to an embodiment is a bonding mode based on an ester bond between a hydroxyl group of the camptothecin derivative and the side chain carboxyl group of aspartic acid and/or glutamic acid of the polyamino acid segment. The ester bond may be formed with any one of the hydroxyl group at the 10-position and the hydroxyl group at the 20-position of the camptothecin derivative, or may be a mixture thereof. Preferably, the bonding mode of the residue is an ester bond formed by the hydroxyl group at the 10-position. An embodiment that does not include an ester bond of the hydroxyl group at the 20-position of the camptothecin derivative is more preferred.

The C1-C6 alkyl group which may have a substituent for $R_5$ in General Formula (2) may be a linear, branched or cyclic C1-C6 alkyl group which may have a substituent. As the substituent, the alkyl group may include a hydroxyl group, a halogen atom, an amino group, an alkylamino group, a dialkylamino group, an alkoxy group, an aryl group, or the like. Examples of the C1-C6 alkyl group for $R_5$ include, but not limited to, a methyl group, an ethyl group, a n-propyl group, an isopropyl group, a n-butyl group, a s-butyl group, a t-butyl group, and a benzyl group. A linear, branched or cyclic C1-C4 alkyl group which may have a substituent is more preferred, and particularly, an ethyl group is more preferred.

Examples of the silyl group which may have a substituent for $R_5$ include, but not limited to, a trimethylsilyl group, a triethylsilyl group, a t-butyldimethylsilyl group, a triisopropylsilyl group, and a t-butyldiphenylsilyl group. A t-butyldimethylsilyl group is preferred.

Regarding $R_5$, a hydrogen atom or a C1-C6 alkyl group which may have a substituent is preferred. A hydrogen atom or an ethyl group is particularly preferred.

The C1-C6 alkyl group which may have a substituent for $R_6$ of General Formula (2) may be a linear, branched or cyclic C1-C6 alkyl group which may have a substituent. As the substituent, the alkyl group may have a hydroxyl group, a halogen atom, an amino group, an alkylamino group, a dialkylamino group, an alkoxy group, an aryl group, or the like. Examples of the C1-C6 alkyl group for $R_6$ include, but not limited to, a methyl group, an ethyl group, a n-propyl group, an isopropyl group, a n-butyl group, a s-butyl group, a t-butyl group, a benzyl group, and a dimethylaminomethyl group. $R_6$ is particularly preferably a hydrogen atom or a dimethylaminomethyl group.

The camptothecin derivative of $R_3$ of General Formula (1) is preferably 7-ethyl-10-hydroxycamptothecin and/or nogitecan (9-dimethylaminomethyl-10-hydroxycamptothecin). That is, 7-ethyl-10-hydroxycamptothecin, which is a compound represented by General Formula (2) having an ethyl group for $R_5$ and a hydrogen atom for $R_6$, is preferred. Alternatively, nogitecan (9-dimethylaminomethyl-10-hydroxycamptothecin), which is a compound represented by General Formula (2) having a hydrogen atom for $R_5$ and a dimethylaminomethyl group for $R_6$, is preferred.

An embodiment of using the camptothecin derivative as a pharmacologically active substance according to the present invention, is preferably a camptothecin derivative-conjugated block copolymer, in which $R_3$ in General Formula (1) is a camptothecin derivative. This will be explained below.

The present camptothecin derivative-conjugated block copolymer is a block copolymer represented by General Formula (1), in which polyethylene glycol segment is connected with a poly(aspartic acid and/or glutamic acid) derivative segment, and is a camptothecin derivative-conjugated block copolymer in which $R_3$ represents a residue of a camptothecin derivative. That is, the present camptothecin derivative-conjugated block copolymer is a camptothecin derivative-conjugated block copolymer represented by General Formula (1):

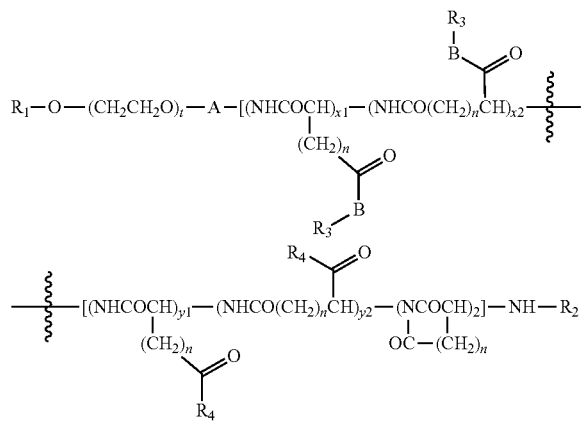

(1)

wherein $R_1$ represents a hydrogen atom or a C1-C6 alkyl group which may have a substituent; t represents an integer of 20 to 270; A represents a C1-C6 alkylene group which may have a substituent; $R_2$ represents substituent selected from the group consisting of a hydrogen atom, a C1-C6 acyl group, and a C1-C6 alkoxycarbonyl group; $R_3$ represents a residue of a camptothecin derivative; $R_4$'s represent one or more substituents selected from the group consisting of a linear, branched or cyclic C1-C30 alkoxy group which may have a substituent, a linear, branched or cyclic C1-C30 alkylamino group which may have a substituent, a linear, branched or cyclic C1-C30 dialkylamino group which may have a substituent, a C1-C8 alkylaminocarbonyl-C1-C8 alkylamino group which may have a substituent, a residue of a hydrophobic fluorescent substance, and a hydroxyl group;

B represents a linking group; n represents 1 or 2; $x_1$, $x_2$, $y_1$, $y_2$, and z each independently represent an integer of 0 to 25; $(x_1+x_2)$ represents an integer of 1 to 25; $(x_1+x_2+y_1+y_2+z)$ represents an integer of 3 to 25; and the each constituent unit to which $R_3$ or $R_4$ is linked, and the constituent unit in which a side chain carbonyl group has been intramolecularly cyclized are each independently randomly arranged.

Here, General Formulae $R_1$, $R_2$, $R_4$, A, B, t, $x_1$, $x_2$, $y_1$, $y_2$, and z have the same meanings as described above.

When $R_3$ of General Formula (1) is a residue of a camptothecin derivative, the camptothecin derivative may be 7-ethyl-10-hydroxycamptothecin, irinotecan, nogitecan, or the like. These camptothecin derivatives have a hydroxyl group at the 20-position of the camptothecin skeleton. Furthermore, 7-ethyl-10-hydroxycamptothecin and nogitecan have a hydroxyl group at the 10-position. Therefore, the camptothecin derivative is such that this hydroxyl group at the 10-position and/or the hydroxyl group the 20-position form an ester bond with the side chain carboxyl group of aspartic acid and/or glutamic acid.

Regarding the camptothecin derivative in connection with the residue of the camptothecin derivative of $R_3$, it is preferable to use a camptothecin derivative represented by General Formula (2):

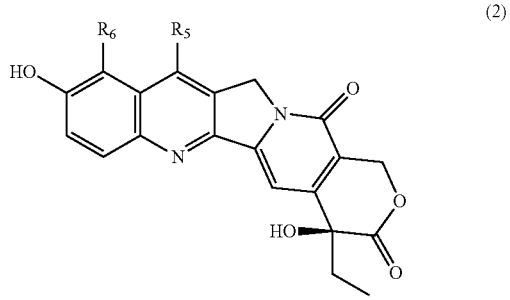

(2)

the polyamino acid segment. The ester bond may be formed by any one of the hydroxyl group at the 10-position and the hydroxyl group at the 20-position of the camptothecin derivative, or may be a mixture thereof. Preferably, the bonding mode of the residue is an ester bond formed by the hydroxyl group at the 10-position. An embodiment that does not include an ester bond of the hydroxyl group at the 20-position of the camptothecin derivative is more preferred.

The camptothecin derivative of $R_3$ of General Formula (1) is preferably 7-ethyl-10-hydroxycamptothecin and/or nogitecan (9-dimethylaminomethyl-10-hydroxycamptothecin). That is, 7-ethyl-10-hydroxycamptothecin, which is a compound represented by General Formula (2) having an ethyl group for $R_5$ and a hydrogen atom for $R_6$, is preferred. Alternatively, nogitecan (9-dimethylaminomethyl-10-hydroxycamptothecin), which is a compound represented by General Formula (2) having a hydrogen atom for $R_5$ and a dimethylaminomethyl group for $R_6$, is preferred.

In regard to the camptothecin derivative of $R_3$ of General Formula (1), identical compounds may exist in the same molecule of the camptothecin derivative-conjugated block copolymer, or plural kinds of compounds may exist as a mixture. It is preferable that $R_3$'s are identical compounds.

A preferred embodiment of the case in which the present physiologically active substance is a camptothecin derivative, may be a block copolymer in which a polyethylene glycol segment is connected with a polyglutamic acid derivative segment, and is a camptothecin derivative-conjugated block copolymer in which a camptothecin derivative is linked to the side chain carboxyl group of a glutamic acid unit. That is, it is preferable to use a polyglutamic acid segment as the polyamino acid segment of the block copolymer. That is, in regard to General Formula (1), it is preferable that n is 2.

A more preferred embodiment of the camptothecin derivative-conjugated block copolymer is a camptothecin derivative-conjugated block copolymer represented by General Formula (4):

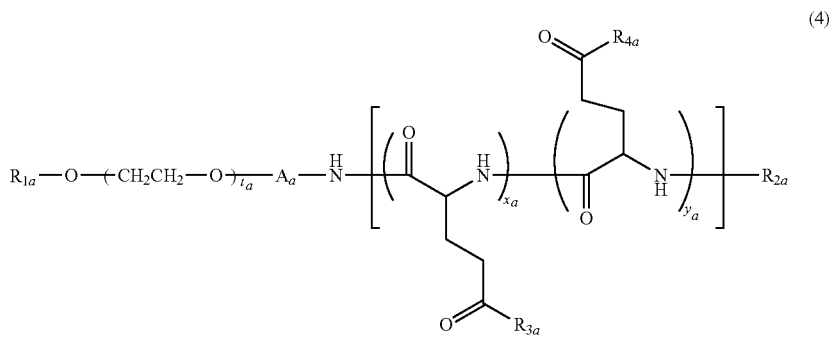

(4)

wherein $R_5$ represents one substituent selected from the group consisting of a hydrogen atom, a C1-C6 alkyl group which may have a substituent, and a silyl group which may have a substituent; and $R_6$ represents a hydrogen atom, or a C1-6 alkyl group which may have a substituent.

Here, $R_5$ and RE in General Formula (2) have the same meanings as described above.

According to an embodiment, the bonding mode of the residue is a bonding mode based on an ester bond between a hydroxyl group of the camptothecin derivative and the side chain carboxyl group of aspartic acid and/or glutamic acid of wherein $R_{1a}$ represents a hydrogen atom or a C1-C6 alkyl group which may have a substituent; $t_a$ represents an integer of 20 to 270; $A_a$ represents a C1-C6 alkylene group which may have a substituent; $x_a$ and $y_a$ each represent an integer; $(x_a+y_a)$ represents an integer of 3 to 20; the proportion of $x_a$ with respect to $(x_a+y_a)$ is 1 to 100%, while the proportion of $y_a$ is 0% to 99%; $R_{2a}$ represents one selected from the group consisting of a hydrogen atom, a C1-C6 acyl group which may have a substituent, and a C1-6 alkoxycarbonyl group which may have a substituent; $R_{3a}$ represents a residue of a camptothecin derivative; $R_{4a}$'s may be identical or different, and represent one or more substituents selected from the group consisting of a C1-C8 alkoxy group which may have a substituent, a C1-C8 alkylamino group which may have a substituent, a di-C1-C8 alkylamino group which may have a substituent, a C1-C8 alkylaminocarbonyl-C1-C8 alkylamino group which may have a substituent, and a hydroxyl group; and the each constituent unit to which $R_3$ or $R_4$ is linked, and the glutamic acid units to which $R_{3a}$ is linked and the glutamic acid units to which $R_{4a}$ is linked are each independently polymerized in a random arrangement.

The C1-C6 alkyl group which may have a substituent for $R_{1a}$ may be a linear, branched or cyclic C1-C6 alkyl group which may have a substituent. Examples thereof include, but not limited to, a methyl group, an ethyl group, a n-propyl group, an isopropyl group, a n-butyl group, a s-butyl group, a t-butyl group, a n-pentyl group, a cyclopentyl group, a n-hexyl group, and a cyclohexyl group.

Examples of the substituent that may be carried may include, but not limited to, a halogen atom, a nitro group, a cyano group, a hydroxyl group, a mercapto group, a carbocyclic or heterocyclic aryl group, an alkylthio group, an arylthio group, an alkylsulfinyl group, an arylsulfinyl group, an alkylsulfonyl group, an arylsulfonyl group, a sulfamoyl group, an alkoxy group, an aryloxy group, an acyloxy group, an alkoxycarbonyloxy group, a carbamoyloxy group, a substituted or unsubstituted amino group, an acylamino group, an alkoxycarbonylamino group, a ureido group, a sulfonylamino group, a sulfamoylamino group, a formyl group, an acyl group, a carboxyl group, an alkoxycarbonyl group, a carbamoyl group, and a silyl group. The position of substitution on the aromatic ring may be the ortho-position, the meta-position, or the para-position.

Examples of $R_{1a}$ include, but not limited to, a methyl group, an ethyl group, a n-propyl group, an isopropyl group, a n-butyl group, a s-butyl group, a t-butyl group, a benzyl group, a 2,2-dimethoxyethyl group, a 2,2-diethoxyethyl group, and a 2-formylethyl group. A linear, branched or cyclic C1-C4 alkyl group which may have a substituent is more preferred. Particularly, a methyl group, an ethyl group, a n-propyl group, an isopropyl group, a n-butyl group, a s-butyl group, a t-butyl group, and the like are more preferred.

Examples of the C1-C6 alkylene group which may have a substituent for $A_a$ include, but not limited to, a methylene group, an ethylene group, a n-propylene group, and a n-butylene group. As the substituent that may be carried, the alkylene group may have a hydroxyl group, a halogen atom, an amino group, an alkylamino group, a dialkylamino group, an alkoxy group, an aryl group, or the like.

Particularly, $A_a$ is more preferably an ethylene group or a n-propylene group.

$t_a$ of General Formula (4) represents the number of polymerized units of an ethyleneoxy group in the polyethylene glycol segment. This $t_a$ is an integer of 20 to 270. That is, the molecular weight of the polyethylene glycol segment is 0.8 kilodaltons to 12 kilodaltons. If the value of $t_a$, which is the degree of polymerization of the polyethylene glycol segment, is smaller than 20, the camptothecin derivative-conjugated block copolymer thus obtainable does not have sufficient water-solubility, and there is a risk that desired biokinetics may not be presented. On the other hand, if $t_a$ is larger than 270, there is a risk that the total molecular weight of the camptothecin derivative-conjugated block copolymer thus obtainable becomes so large that desired biokinetics may not be presented, and unexpected tissue disorders such as hepatotoxicity may develop. This $t_a$ is preferably an integer of 22 to 230, and more preferably an integer of 30 to 180. That is, the molecular weight of the polyethylene glycol segment is preferably 1 kilodalton to 10 kilodaltons, and more preferably 1.3 kilodaltons to 8 kilodaltons.

The block copolymer of General Formula (4) has a polyglutamic acid derivative segment, and $(x_a+y_a)$ represents the number of polymerized units of the polyglutamic acid derivative. The number of polymerized units of the polyglutamic acid derivative is 3 to 20, that is, $(x_a+y_a)$ is an integer of 3 to 20. If the value of $(x_a+y_a)$ is smaller than 3, there is a risk that in regard to the camptothecin derivative-conjugated block copolymer thus obtainable, the laser light scattering intensity that will be described below may not fall in an optimal range. On the other hand, if the value of $(x_a+y_a)$ is larger than 20, the total molecular weight of the camptothecin derivative-conjugated block copolymer thus obtainable becomes large, and also, there is a risk that the laser light scattering intensity that will be described below may not fall in an optimal range. That is, if the value of $(x_a+y_a)$ is not in the range of 3 to 20, there is a risk that the action of enhancing the antitumor effect and/or an effect of reducing adverse effects may not be obtained. It is preferable that the number of polymerized units of the polyglutamic acid derivative is appropriately set in consideration of the total molecular weight of the camptothecin derivative-conjugated block copolymer. This $(x_a+y_a)$ is preferably an integer of 5 to 15.

$(x_a+y_a)$, which is the number of polymerized units of the polyglutamic acid derivative, may be determined by an analysis by $^1$H-NMR, or by performing neutralization titration on the polyethylene glycol-polyglutamic acid block copolymer before $R_{3a}$ and $R_{4a}$ are linked thereto.

The C1-C6 acyl group which may have a substituent for $R_{2a}$ may be a linear, branched or cyclic C1-C6 acyl group which may have a substituent. Regarding the substituent, a hydroxyl group, a halogen atom, an amino group, an alkylamino group, a dialkylamino group, an alkoxy group, an aryl group, or the like may be included. Examples of the C1-C6 acyl group for $R_{2a}$ include, but not limited to, a formyl group, an acetyl group, a trichloroacetyl group, a trifluoroacetyl group, a propionyl group, a pivaloyl group, a benzylcarbonyl group, and a phenethylcarbonyl group. A linear, branched or cyclic C1-C4 acyl group which may have a substituent is more preferred, and an acetyl group, a trichloroacetyl group, and a trifluoroacetyl group are more preferred.

The C1-C6 alkoxycarbonyl group which may have a substituent for $R_{2a}$ may be a linear, branched or cyclic C1-C6 alkoxycarbonyl group which may have a substituent. Regarding the substituent, a hydroxyl group, a halogen atom, an amino group, an alkylamino group, a dialkylamino group, an alkoxy group, an aryl group, or the like may be included. Examples of the C1-C6 alkoxycarbonyl group for $R_{2a}$ include, but not limited to, a methoxycarbonyl group, an ethoxycarbonyl group, a t-butoxycarbonyl group, a benzyloxycarbonyl group, and a 9-fluorenylmethyloxycarbonyl group.

$R_{3a}$ in General Formula (4) is a residue of a camptothecin derivative represented by General Formula (2):

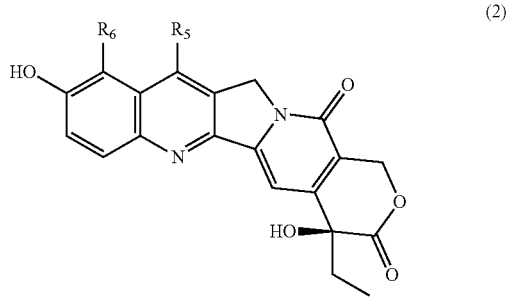

(2)

wherein $R_5$ represents one substituent selected from the group consisting of a hydrogen atom, a C1-C6 alkyl group which may have a substituent, and a silyl group which may have a substituent; and $R_6$ represents a hydrogen atom or a C1-C6 alkyl group which may have a substituent.

$R_5$ and $R_6$ in General Formula (2) have the same meanings as described above.

The bonding mode of the residue according to an embodiment is preferably a bonding mode based on an ester bond between a hydroxyl group of the camptothecin derivative and a side chain carboxyl group of the polyglutamic acid segment. The ester bond may be formed with any one of the hydroxyl group at the 10-position and the hydroxyl group at the 20-position of the camptothecin derivative, or may be a mixture thereof. Preferably, the bonding mode of the residue is an ester bond formed by the hydroxyl group at the 10-position. An embodiment that does not include an ester bond of the hydroxyl group at the 20-position of the camptothecin derivative is more preferred.

The camptothecin derivative of $R_{3a}$ of General Formula (4) is preferably 7-ethyl-10-hydroxycamptothecin and/or nogitecan (9-dimethylaminomethyl-10-hydroxycamptothecin). That is, 7-ethyl-10-hydroxycamptothecin, which is a compound represented by General Formula (2) having an ethyl group for $R_5$ and a hydrogen atom for $R_6$, is preferred. Alternatively, nogitecan (9-dimethylaminomethyl-10-hydroxycamptothecin), which is a compound represented by General Formula (2) having a hydrogen atom for $R_5$ and a dimethylaminomethyl group for $R_6$, is preferred.

In regard to the camptothecin derivative of $R_{3a}$ of General Formula (4), identical compounds may exist in the same molecule of the camptothecin derivative-conjugated block copolymer, or plural kinds of compounds may exist as a mixture. It is preferable that $R_{3a}$'s are identical compounds.

In General Formula (4), $x_a$ represents the total number of glutamic acid units to which the camptothecin derivative of $R_{3a}$ is linked. It is an essential configuration to have the glutamic acid unit to which the camptothecin derivative is linked, and $x_a$ is an integer of 1 or larger. Preferably, $x_a$ is an integer of 2 to 18, and more preferably an integer of 3 to 16.

The proportion of $x_a$ with respect to $(x_a+y_a)$, which is the number of polymerized units of the polyglutamic acid derivative, is 1% to 100%. The proportion of $x_a$ with respect to $(x_a+y_a)$ is preferably 10% to 90%, and more preferably 20% to 80%.

The number of bonds of camptothecin of $x_a$ may be obtained by hydrolyzing the camptothecin derivative-conjugated block copolymer thus obtainable, quantitatively determining by HPLC those released camptothecin derivative molecules or fragment molecules originating therefrom, thereby calculating the content of the camptothecin derivative, and calculating the number of bonds from the value.

$R_{4a}$'s in General Formula (4) are one or more substituents selected from the group consisting of a C1-C8 alkoxy group which may have a substituent, a C1-C8 alkylamino group which may have a substituent, a di-C1-C8 alkylamino group which may have a substituent, a C1-C8 alkylaminocarbonyl-C1-C8 alkylamino group which may have a substituent, and a hydroxyl group.

This $R_{4a}$ may be optionally introduced for the purpose of controlling the physical properties of the present camptothecin derivative-conjugated block copolymer. For example, hydrophobicity of the polyglutamic acid segment of the camptothecin derivative-conjugated block copolymer may be increased by introducing a hydrophobic group into $R_{4a}$. On the other hand, when a hydrophilic substituent including an ionic functional group that is capable of forming a salt, such as an amino group, a carboxyl group, or a hydroxyl group, is introduced as $R_{4a}$, hydrophilicity of the polyglutamic acid segment of the camptothecin derivative-conjugated block copolymer may be increased. In a case in which $R_{4a}$ is a hydroxyl group, the side chain carboxyl group of the polyglutamic acid segment is a free carboxylic acid.

The substituents for $R_{4a}$ may be substituents of a single kind, or may be substituents of plural kinds.

The C1-C8 alkoxy group which may have a substituent for $R_{4a}$ may be a linear, branched or cyclic C1-C8 alkoxy group which may have a substituent. That is, this is an alkoxy group in which an ester type modifying group is linked to a side chain carboxyl group of the polyglutamic acid segment. The alkoxy group may have a hydroxyl group, a halogen atom, an amino group, an alkylamino group, a dialkylamino group, an alkoxy group, an aryl group, or the like as the substituent. Examples of the C1-C8 alkoxy group for $R_{4a}$ include, but not limited to, a methoxy group, an ethoxy group, a propoxy group, an isopropoxy group, a butoxy group, a t-butoxy group, a cyclohexyloxy group, and a benzyloxy group.

The C1-C8 alkylamino group which may have a substituent for $R_{4a}$ may be a linear, branched or cyclic C1-C8 alkylamino group which may have a substituent. That is, this is an alkylamino group in which an alkylamide type modifying group is linked to a side chain carboxyl group of the polyglutamic acid segment. The alkylamino group may include a hydroxyl group, a halogen atom, an amino group, an alkylamino group, a dialkylamino group, an alkoxy group, an aryl group, or the like as the substituent. Examples of the C1-C8 alkylamino group for $R_{4a}$ include, but not limited to, a methylamino group, an ethylamino group, a propylamino group, an isopropylamino group, a butylamino group, a t-butylamino group, a cyclohexylamino group, and a benzylamino group.

An amino acid having a protected carboxyl group is also included in the C1-C8 alkylamino group which may have a substituent. Examples of the amino acid having a protected carboxyl group that may be used include, but not limited to, glycine methyl ester, glycine benzyl ester, β-alanine methyl ester, β-alanine benzyl ester, alanine methyl ester, leucine methyl ester, and phenylalanine methyl ester.

The di-C1-C8 alkylamino group which may have a substituent for $R_{4a}$ may be a linear, branched or cyclic di-C1-C8 alkylamino group which may have a substituent. That is, this is a dialkylamino group in which a dialkylamide type modifying group is linked to a side chain carboxyl group of the polyglutamic acid segment. As the substituent, the dialkylamino group may include a hydroxyl group, a halogen atom, an amino group, an alkylamino group, a dialkylamino group, an alkoxy group, an aryl group, or the like. Examples of the di-C1-C8 alkylamino group for $R_{4a}$ include, but not limited to, a dimethylamino group, a diethylamino group, a dipropylamino group, a diisopropylamino group, a dibutylamino group, a pyrrolidino group, a piperidino group, a dibenzylamino group, and a N-benzyl-N-methylamino group.

The substituent for $R_{4a}$ may also be a C1-C8 alkylaminocarbonyl-C1-C8 alkylamino group which may have a substituent. This is a group in which a urea type modifying group is linked to a side chain carboxyl group of the polyglutamic acid segment, and which has —N($R_{4ax}$)CONH ($R_{4ay}$) [wherein $R_{4ax}$ and $R_{4ay}$ may be identical or different, and each represents a linear, branched or cyclic C1-C8 alkyl group which may be substituted with a tertiary amino group] as the side chain carboxyl group.

Examples of the linear, branched or cyclic C1-C8 alkyl group which may be substituted with a tertiary amino group for $R_{4ax}$ and $R_{4ay}$ may include, but not limited to, a methyl group, an ethyl group, a n-propyl group, an isopropyl group, a cyclohexyl group, a 2-dimethylaminoethyl group, and a 3-dimethylaminopropyl group.

Examples of the C1-C8 alkylaminocarbonyl-C1-C8 alkylamino group which may have a substituent for $R_{4a}$ include, but not limited to, a methylaminocarbonylmethylamino group, an ethylaminocarbonylethyamino group, an isopropylaminocarbonylisopropylamino group, a cyclohexylaminocarbonylcyclohexylamino group, an ethylaminocarbonyl-(3-dimethylaminopropyl)amino group, and a (3-dimethylaminopropyl)aminocarbonylethylamino group.

$R_{4a}$ in General Formula (4) may also be a hydroxyl group. That is, the side chain carboxylic acid of glutamic acid is a free carboxylic acid. In this case, the side chain carboxylic acid may be in the form of free acid, or may be in the form of any pharmaceutically acceptable carboxylic acid salt. Examples of the carboxylic acid salt include, but not limited to, a lithium salt, a sodium salt, a potassium salt, a magnesium salt, a calcium salt, and an ammonium salt, which are included in the present invention.

$R_{4a}$ in General Formula (4) is preferably a C1-C8 alkylaminocarbonyl-C1-C8 alkylamino group and/or a hydroxyl group. That is, an embodiment in which $R_{4a}$'s include a mixture of a C1-C8 alkylaminocarbonyl-C1-C8 alkylamino group and a hydroxyl group, or an embodiment in which $R_{4a}$'s include hydroxyl groups only, is preferred.

In General Formula (4), $y_a$ represents the total number of glutamic acid units to which $R_{4a}$ is linked. The glutamic acid unit to which $R_{4a}$ is linked is an optional configuration, and $y_a$ is an integer of 0 to 19. Preferably, $y_a$ is an integer of 2 to 18, and more preferably 4 to 17.

The proportion of $y_a$ with respect to $(x_a+y_a)$, which is the number of polymerized units of the polyglutamic acid derivative, is 0% to 99%. The proportion of $y_a$ with respect to $(x_a+y_a)$ is preferably 10% to 90%, and more preferably 20% to 80%.

$y_a$, which is the number of bonds of $R_{4a}$, may be determined by measuring the resulting camptothecin derivative-conjugated block copolymer by $^1$H-NMR under alkaline conditions, and calculating $y_a$ from the signal intensity ratio.

In regard to the camptothecin derivative-conjugated block copolymer according to the present invention, the polyglutamic acid derivative segment is a polymer segment including a mixture of a glutamic acid derivative unit that includes $R_{3a}$ at a side chain carboxyl group, and a glutamic acid derivative unit that includes $R_{4a}$. The glutamic acid derivative unit that includes $R_{3a}$ and the glutamic acid derivative unit that includes $R_{4a}$ may be of block polymerized type, in which the glutamic acid derivative units are arranged in a polarized manner, or may be of randomly polymerized type, in which the glutamic acid derivative units are arranged irregularly. Preferred is a randomly polymerized type polyglutamic acid derivative segment in which the glutamic acid derivative units including $R_{3a}$ and the glutamic acid derivative units including $R_{4a}$ are irregularly arranged.

The present camptothecin derivative-conjugated block copolymer has a molecular weight of from 2 kilodaltons to 15 kilodaltons. If the molecular weight is smaller than 2 kilodaltons, there is a risk that the pharmacokinetics characteristics based on macromolecularization may not be presented, and desired pharmacological action such as the action of enhancing an antitumor effect may not be obtained. Meanwhile, if the molecular weight is more than 15 kilodaltons, there is a risk that avoidance of adverse effects from an antitumor effect is not easily achieved, and adverse effects may be strongly presented. Particularly, camptothecin derivatives have a feature that persistence of hematotoxicity such as myelosuppression is strongly manifested. If the molecular weight is more than 15 kilodaltons, hematotoxicity is strongly manifested. Therefore, control of the molecular weight is very important for the present camptothecin derivative-conjugated block copolymer. The molecular weight of the present camptothecin derivative-conjugated block copolymer is preferably from 3 kilodaltons to 12 kilodaltons, and more preferably from 3 kilodaltons to 10 kilodaltons.

Regarding the molecular weight of the camptothecin derivative-conjugated block copolymer according to the present invention, the calculated value obtained by summing the respective constituent molecular weight of each constituent part is employed as the "molecular weight of the camptothecin derivative-conjugated block copolymer". That is, a calculated value obtained by summing: (1) the molecular weight of the polyethylene glycol segment; (2) the molecular weight of the polyglutamic acid main chain; (3) the total molecular weight of the camptothecin derivative obtained by multiplying the molecular weight of the residue of the camptothecin derivative by the number of bonds thereof; and (4) the total molecular weight of substituents other than the camptothecin derivative obtained by multiplying the molecular weight of residues of the substituents by the number of bonds thereof, is employed as the molecular weight.

The "molecular weight of the camptothecin derivative-conjugated block copolymer" may be a molecular weight defined with an accuracy of the unit of kilodaltons. Therefore, the method for analyzing the each constituent part is not particularly limited as long as it is an analysis method with sufficient accuracy for the measurement of the molecular weight of the polyamino acid derivative to the unit of kilodaltons, and various analysis methods may be selected as appropriate. Preferable analysis method for the each constituent part will be described below.

The molecular weight of the polyethylene glycol segment in the above (1) is a measured value of the molecular weight of the polyethylene glycol compound that constitutes the polyethylene glycol segment, and an average molecular weight that may be determined by the peak top molecular weight measured by a GPC method based on polyethylene glycol standard products is employed.

The molecular weight of the polyglutamic acid main chain in the above (2) is a calculated value obtained by multiplying the molecular weight of the polymerized monomer unit of the main chain by the number of polymerized units. In regard to the number of polymerized units, it is preferable to use a number of polymerized units calculated by a method of quantitatively determining the side chain carboxyl groups of the polyglutamic acid by neutralization titration, or a number of polymerized units calculated from the integral values of $^1$H-NMR. It is preferable to use a neutralization titration method.

The total molecular weight of the camptothecin derivative in the above (3) is a calculated value obtained by multiplying the molecular weight of the camptothecin derivative by the number of bonds thereof. The number of bonds may be determined by cleaving the camptothecin derivative from the camptothecin derivative-conjugated block copolymer, and quantitatively analyzing the released camptothecin derivative molecules or fragment molecules originating therefrom.

The total molecular weight of substituents other than the camptothecin derivative in the above (4) is a calculated value obtained by multiplying the molecular weight of the residues of the substituents by the number of bonds thereof. The number of bonds of the substituents may be determined by a quantitative analysis after hydrolysis from the polyglutamic acid. Also, the number of bonds may also be calculated from the integral values of $^1$H-NMR. In a case in which the substituent other than the camptothecin derivative is an ester type modifying group, a method of quantitatively analyzing a corresponding alcohol compound that has been ester-cleaved by hydrolysis is preferred. On the other hand, in a case in which the substituent other than the camptothecin derivative includes an amide type modifying group and a urea type modifying group, it is preferable to calculate the number of bonds by $^1$H-NMR.

The present camptothecin derivative-conjugated block copolymer has a property of exhibiting self-associating properties in an aqueous solution. That is, the camptothecin derivative-conjugated block copolymer has a property in which when a 1 mg/mL aqueous solution of the campcothecin derivative-conjugated block copolymer is subjected to a particle size distribution analysis based on a dynamic light scattering method using laser light, the camptothecin derivative-conjugated block copolymer is measured as nanoparticles having a volume average particle diameter of about a few nanometers to about 20 nanometers. It is preferable that the present camptothecin derivative-conjugated block copolymer has a property in which the derivative forms nanoparticles having a volume average particle diameter of less than 20 nanometers at the maximum in a 1 mg/mL aqueous solution. In this case, a particle size distribution analysis in an aqueous solution based on pure water is employed. Preferably, the camptothecin derivative-conjugated block copolymer is characterized in that the volume average particle diameter is measured to be less than 20 nanometers by a particle size distribution analysis method based on a dynamic light scattering method using laser light, and more preferably, the block copolymer has a property in which the block copolymer is analyzed as nanoparticles having a particle size of 3 to 15 nanometers.

The volume average particle diameter according to the present invention is the particle size of the peak that exists at the largest proportion in a volume distribution that may be measured with, for example, a ZetaPotential/Particlesizer NICOMP 380 ZLS (analysis method: NICOMP method) manufactured by Particle Sizing Systems, LLC, or a particle size zeta potential analyzer, ZETASIZER NANO ZS (analysis method: NNLS method) manufactured by Malvern Instruments, Ltd.

Since the present camptothecin derivative-conjugated block copolymer is a block copolymer in which a hydrophilic polyethylene glycol segment is connected with a polyglutamic acid segment that includes a hydrophobic camptothecin derivative via an ester bond, it is considered that in an aqueous solution, the polyglutamic acid segments of a plurality of the block copolymer molecules associate with one another based on the hydrophobic interaction of the polyglutamic acid derivative segment. Consequently, it is speculated that micelle-like associated bodies having a core-shell structure are formed, in which the polyglutamic acid segment forms an inner core (core part) and the hydrophilic polyethylene glycol segment covers the periphery of the inner core and forms an outer shell layer (shell part), and these are observed as the nanoparticle described above.

The present camptothecin derivative-conjugated block copolymer needs to have a property of forming nanoparticles in an aqueous solution, for the purpose of reducing adverse effects. Particularly, it is important that the camptothecin derivative-conjugated block copolymer has nanoparticle-forming properties for the purpose of suppressing the occurrence of hepatotoxicity.

It is effective to use the light scattering intensity obtained by using laser light, as an index for the nanoparticle-forming properties of the present camptothecin derivative-conjugated block copolymer. That is, the nanoparticle-forming properties of the camptothecin derivative-conjugated block copolymer in an aqueous solution may be checked by utilizing the laser light scattering intensity as an index. In that case, a method of checking the nanoparticle-forming properties in an aqueous solution of the camptothecin derivative-conjugated block copolymer by using toluene as a light scattering intensity standard sample, and utilizing the relative intensity with respect to toluene as an index, is effective.

The present camptothecin derivative-conjugated block copolymer is such that the laser light scattering intensity in a 1 mg/mL aqueous solution of the block copolymer is from 2 times to 10 times as a relative intensity with respect to the light scattering intensity of toluene. If the relative light scattering intensity is smaller than twice, it is implied that the camptothecin derivative-conjugated block copolymer does not have sufficient nanoparticle-forming properties, and there is a risk that adverse effects such as hepatotoxicity may be manifested. According to the present invention, the value of the relative light scattering intensity is an index indicating that the substance has a nanoparticle-forming ability, and any value is acceptable as long as it is twice or more the light scattering intensity of toluene, without any particular limitations. That is, it is understood that even if the relative light scattering intensity is higher than 10 times, the polymer derivative has a sufficient nanoparticle-forming ability. However, in that case, although there is no risk of highly frequent occurrence of hepatotoxicity, there is a risk of persistence of hematotoxicity. Therefore, it is appropriate to control the relative light scattering intensity to be 10 times or less.

In regard to the aqueous solution, an analyzed value obtained by using an aqueous solution prepared using pure water that does not include microparticles as an analytic sample. The aqueous solution may be optionally dissolved by means of ultrasonic irradiation during solution preparation. The aqueous solution thus prepared is preferably an aqueous solution that has been further subjected to a filtration treatment in order to remove submicron-sized microparticles.

The present camptothecin derivative-conjugated block copolymer is such that the light scattering intensity of an aqueous solution thereof is preferably from 2 times to 8 times, and more preferably from 2 times to 6 times, as a relative intensity with respect to the light scattering intensity of toluene.

In regard to the method for measuring the light scattering intensity obtained by using laser light for the analysis of the nanoparticle-forming properties of the present camptothecin derivative-conjugated block copolymer, a method of using a 1 mg/mL aqueous solution of the camptothecin derivative-conjugated block copolymer as a measurement sample, and measuring the light scattering intensity with a laser light scattering photometer at a measurement temperature of 25° C., a scattering angle of 90°, and a wavelength of 632.8 nm is suitable. Examples of the measuring instrument may include, but not limited to, a dynamic light scattering photometer manufactured by Otsuka Electronics Co., Ltd., DLS-8000DL (measurement temperature: 25° C., scattering angle: 900, wavelength: 632.8 nm, ND filter: 2.5%, PH1: OPEN, PH2: SLIT).

Regarding toluene that is used as a standard substance for the measurement of light scattering intensity, any toluene may be used without particular limitations as long as the toluene has reagent-level purity. It is preferable to use toluene that has been subjected to pretreatment filtration, which is usually performed for the preparation of a sample for a light scattering analysis.

In regard to the present camptothecin derivative-conjugated block copolymer, the mass content of the camptothecin derivative represented by General Formula (2) is from 10% by mass to 60% by mass. If the content of the camptothecin derivative is smaller than 10% by mass, since the content of the hydrophobic camptothecin derivative is small, the nanoparticle-forming properties based on hydrophobic interaction are deteriorated. On the other hand, if the content of the camptothecin derivative is larger than 60% by mass, there is a risk that the water-solubility of the camptothecin derivative-conjugated block copolymer may be markedly decreased. The mass content of the physiologically active substance is preferably from 15% by mass to 50% by mass, and even more preferably from 15% by mass to 40% by mass.

When $R_{4a}$ in General Formula (4) is a C1-C8 alkoxy group which may have a substituent, a C1-C8 alkylamino group which may have a substituent, a di-C1-C8 alkylamino group which may have a substituent, or a C1-C8 alkylaminocarbonyl-C1-C8 alkylamino group which may have a substituent, since the linking group of $R_{4a}$ is an optional substituent, the content ratio of the substituent is 30% by mass or less. The content ratio of the substituent is preferably from 1% by mass to 20% by mass.

The mass content of the polyethylene glycol segment in the present camptothecin derivative-conjugated block copolymer is preferably from 10% by mass to 80% by mass. If the mass content of the polyethylene glycol segment is lower than 10% by mass, the camptothecin derivative-conjugated block copolymer does not have sufficient water-solubility, and therefore, there is a risk that the nanoparticle-forming properties in an aqueous solution may not be secured. On the other hand, if the mass content is larger than 80% by mass, since the mass content of the polyglutamic acid segment including the camptothecin derivative is relatively decreased, there is a risk that the nanoparticle-forming properties in an aqueous solution may not be secured. The mass content of the polyethylene glycol segment is preferably from 20% by mass to 70% by mass, and more preferably from 30% by mass to 65% by mass.

Examples of the method for producing the present camptothecin derivative-conjugated block copolymer may include, but not limited to, a method of producing the camptothecin derivative-conjugated block copolymer by a condensation reaction between a block copolymer in which a polyethylene glycol segment is connected with a polyglutamic acid segment, and a camptothecin derivative with a hydroxyl group at the 10-position; and a method of producing the camptothecin derivative-conjugated block copolymer by linking a polymer component including a polyethylene glycol segment, to a camptothecin-conjugated polyglutamic acid derivative. A method of producing in advance a block copolymer in which a polyethylene glycol segment is connected with a polyglutamic acid segment, and subjecting this block copolymer and a camptothecin derivative with a hydroxyl group at the 10-position to a condensation reaction, is preferred.

Regarding the method for producing a block copolymer in which a polyethylene glycol segment is connected with a polyglutamic acid segment, a method of constructing a polyglutamic acid segment by sequentially polymerizing a glutamic acid-N-carboxylic acid anhydride with a compound including a polyethylene glycol segment; a method of linking a polyethylene glycol segment to a polyamino acid segment; and the like may be mentioned. For the reason that the linking the polyethylene glycol segment to the polyglutamic acid segment is achieved with high reactivity, and it is easy to control the number of polymerized units of the polyglutamic acid, it is preferable to use the former method.

That is, the present camptothecin derivative-conjugated block copolymer may be produced by constructing a polyglutamic acid segment by sequentially polymerizing a glutamic acid-N-carboxylic acid anhydride with a compound including a polyethylene glycol segment, producing a block copolymer in which a polyethylene glycol segment is connected with a polyglutamic acid segment, and reacting this block copolymer with a camptothecin derivative using a condensing agent.

It is preferable that the present camptothecin derivative-conjugated block copolymer is produced according to the method described in Patent Literature 1. That is, a polyethylene glycol compound having a terminal amino group is reacted with a N-carbonylglutamic acid anhydride having a protected side chain carboxyl group at appropriate equivalents, thereby a polyglutamic acid segment having a desired number of polymerized units of glutamic acid is constructed. Subsequently, the side chain carboxyl group is deprotected, and thereby a polyethylene glycol-polyglutamic acid block copolymer in which the side chain carboxyl group contains a free carboxylic acid group is produced. The polyethylene glycol-polyglutamic acid block copolymer is reacted with a camptothecin derivative with a hydroxyl group at the 10-position as represented by General Formula (2) in an appropriate solvent using a condensing agent, and thereby, the present camptothecin derivative-conjugated block copolymer may be produced.

Regarding the solvent that is used for the condensation reaction between the polyethylene glycol-polyglutamic acid block copolymer and the camptothecin derivative, any solvent in which both the compounds are dissolved may be used without any particular limitations. Examples thereof may include, but not limited to, water-soluble organic solvents such as N,N-dimethylformamide (DMF), N-methylpyrrolidone (NMP), and 1,3-dimethyl-2-imidazolidinone (DMI). These solvents may be used singly, or may be used as mixed solvents thereof. A mixed solvent of the above-mentioned solvents and other organic solvents may also be used. Regarding the reaction temperature, the reaction may be carried out usually at a temperature of 0° C. to 180° C., and preferably 5° C. to 50° C.

Regarding the condensing agent to be used, any conventional dehydration condensing agent that induces an ester reaction between a carboxylic acid and a hydroxyl group by a dehydration condensation reaction may be used without any particular problem. Examples of the condensing agent that may be used include, but not limited to, carbodiimide-based condensing agents such as dicyclohexylcarbodiimide (DCC), diisopropylcarbodiimide (DIPCI), and 1-ethyl-3-(3-dimethylaminopropyl)carbodiimide hydrochloride (WSC); triazine-based condensing agents such as 4-(4,6-dimethoxy-1,3,5-triazin-2-yl)-4-methylmorpholium chloride n-hydrate (DMT-MM); 1-ethoxycarbonyl-2-ethoxy-1,2-dihydroquinoline (EEDQ), and di-tert-butyl dicarbonate ($Boc_2O$).

When the above-mentioned carbodiimide-based condensing agents are used, a C1-C8 alkylaminocarbonyl-C1-C8 alkylamino group which may have a substituent: —N($R_{4ax}$)CONH($R_{4ay}$) [wherein $R_{4x}$ and $R_{4ay}$ may be identical or different, and each represent a linear, branched or cyclic C1-C8 alkyl group which may be substituted with a tertiary amino group] may be simultaneously introduced together with the camptothecin derivative, into $R_4$ of General Formula (1) and $R_{4a}$ of General Formula (4). At the time of this condensation reaction, a reaction aid such as N,N-dimethyl-4-aminopyridine (DMAP) may also be used.

The composition of the substituent of $R_{4a}$ in the polyglutamic acid segment in the polymer derivative may be adjusted by regulating the reaction conditions or the like. For example, according to an active esterification method of using EEDQ, $Boc_2O$ or the like as a condensing agent, or an acid chloride forming method of using phosphorus oxychloride, a polyglutamic acid segment including a camptothecin derivative for $R_{3a}$ and a hydroxyl group for $R_{4a}$ in regard to General Formula (4) may be obtained. In the case of introducing an alkylaminocarbonylalkylamino group into $R_{4a}$, a reaction of using a carbodiimide-based condensing agent as described above may be employed.

In regard to General Formula (4), for the purpose of adjusting hydrophobicity of the polyglutamic acid segment, the C1-C8 alkoxy group, the C1-C8 alkylamino group, or the di-C1-C8 alkylamino group may be introduced into $R_{4a}$. Examples of the method used in that case include, but not limited to, a method of activating carboxyl groups of the polyethylene glycol-polyglutamic acid copolymer by adding a condensing agent, and then reacting the copolymer with an alcohol compound or an amino compound, which corresponds to the substituent for $R_{4a}$ that is wished to be introduced, at desired equivalents; or a method of activating the alcohol compound or the amino compound, and then reacting the activated compound with the polyglutamic acid segment of the copolymer. In this case, $R_{4a}$ may be introduced by means of the alcohol compound or the amino compound, and then the camptothecin derivative of $R_{3a}$ may be introduced, or the reverse order is also acceptable. $R_{3a}$ and $R_{4a}$ may also be simultaneously introduced.

The groups corresponding to $R_{4a}$ may be functional groups of a single kind, or may be functional groups of plural kinds. In a case in which plural kinds of functional groups are introduced, when different alcohol compounds or amino compounds are repeatedly reacted, a camptothecin derivative-conjugated block copolymer having a mixture of various substituents for $R_{4a}$ may be synthesized.

After the camptothecin derivative of $R_{3a}$ and the optional substituent of $R_{4a}$ are introduced by the condensation reaction, conventional separation operations or purification operations are optionally carried out, and thereby, the camptothecin derivative-conjugated block copolymer may be obtained.

The present camptothecin derivative-conjugated block copolymer may exhibit a pharmacological effect by slowly cleaving and releasing the camptothecin derivative after being administered in vivo. Therefore, the present camptothecin derivative-conjugated block copolymer may be used as an antitumor agent that is used for the treatment of malignant tumors.

When the present camptothecin derivative-conjugated block copolymer is used as an antitumor agent, the dose may be definitely changed depending on the gender, age, physiological condition, disease condition, and the like of the patient. However, it is preferable to administer the camptothecin derivative-conjugated block copolymer parenterally, usually at a dose of 0.01 to 500 mg/m$^2$ (body surface area), and preferably 0.1 to 250 mg/m$^2$, in terms of the active ingredient, per day for an adult. Regarding the route of administration, it is preferable to use the camptothecin derivative-conjugated block copolymer by parenteral administration. Administration by injection is carried out by intravenous administration, intra-arterial administration, subcutaneous administration, intramuscular administration, intratumor administration, or the like.

It is preferable that the present camptothecin derivative-conjugated block copolymer is used as a pharmaceutical preparation that is conventionally used, for example, an injectable preparation, a tablet, or a powder. In regard to formulation, pharmaceutically acceptable carriers that are conventionally used, for example, a binder, a lubricating agent, a disintegrant, a solvent, an excipient, a solubilizing agent, a dispersant, a stabilizer, a suspending agent, a preservative, a soothing agent, a colorant, and a fragrance may be used. In the case of an injectable liquid preparation, a solvent is usually used. Examples of the solvent include, but not limited to, water, physiological saline, a 5% glucose or mannitol solution; water-soluble organic solvents, such as glycerol, ethanol, dimethyl sulfoxide, N-methylpyrrolidone, polyethylene glycol, a chromophore; mixed liquids thereof; and mixed liquids of water and the water-soluble organic solvents. It is preferable that the camptothecin derivative-conjugated block copolymer is used after being prepared into an administrable pharmaceutical preparation using these additives for formulation.

Regarding the use of the present camptothecin derivative-conjugated block copolymer as an antitumor agent, the block copolymer is used for the treatment of malignant tumor diseases. The malignant tumors that may be treated are not particularly limited, and the camptothecin derivative-conjugated block copolymer may be applied to the treatment of malignant tumors such as breast cancer, non-small cell lung cancer, small cell lung cancer, colorectal cancer, non-Hodgkin's lymphoma (NHL), renal cell carcinoma, prostate cancer, hepatocarcinoma, stomach cancer, pancreatic cancer, soft tissue sarcoma, malignant skin cancer, carcinoid tumors, head and neck cancer, melanoma, ovarian cancer, cholangiocarcinoma, mesothelioma, and multiple myeloma. Particularly, the camptothecin derivative-conjugated block copolymer is adequate for the treatment of non-small cell lung cancer, cervical cancer, ovarian cancer, stomach cancer (inoperable or recurrent), colorectal cancer (inoperable or recurrent), breast cancer (inoperable or recurrent), squamous cell carcinoma, and malignant lymphoma (non-Hodgkin's lymphoma), for which camptothecin derivatives have been used for the treatment.

Another preferred embodiment of the present invention may be the block copolymer in which a resorcinol derivative having HSP90 inhibitory activity as a physiologically active substance. A resorcinol derivative-conjugated block copolymer that uses a resorcinol derivative as the physiologically active substance will be explained below.

Resorcinol derivatives are known to exhibit antitumor activity and the like by binding to the HSP90 (heat-shock protein 90) family proteins and inhibiting the functions of the HSP90 family proteins (Hsp90 inhibitors as novel cancer chemotherapeutic agents. Trends Mol Med. 2002; 8 (4 Suppl.): p. S55-61). Regarding the resorcinol derivatives having HSP90 inhibitory activity, compounds having a triazole skeleton (see WO 05/000300 A, WO 06/055760 A, WO 05/018674 A, and the like), an isoxazole skeleton (see WO 04/072051 A), and a pyrazole skeleton (see WO 03/055860 A, and the like are known. Since these compounds have a resorcinol structure having hydroxyl groups, the compounds may be applied to the present block copolymer by using the hydroxyl groups as linking groups. That is, the block copolymer is in the form in which a hydroxyl group of a resorciniol group forms an ester bond with the side chain carboxyl group of aspartic acid and/or glutamic acid directly or via an appropriate linking group.

A resorcinol derivative having HSP90 inhibitory activity is preferably a resorcinol derivative of General Formula (3):

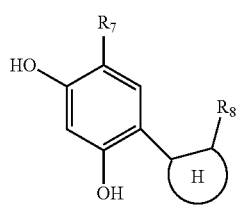

(3)

wherein $R_7$ represents one selected from the group consisting of a mercapto group, a hydroxyl group, a halogen atom, a nitro group, a cyano group, a C1-C20 alkyl group, a C2-C20 alkenyl group, a C2-C20 alkynyl group, a carbocyclic or heterocyclic aryl group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxy group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, a carboxyl group, a C1-C8 alkoxycarbonyl group, a carbamoyl group, and a C1-C8 alkylsilyl group;

$R_8$ represents one selected from the group consisting of a carbocyclic or heterocyclic aryl group which may have a substituent, a C1-C20 alkyl group, a C2-C20 alkenyl group, a C2-C20 alkynyl group, a C1-C20 alkylamino group, and a C1-C20 acylamino group; and ring H is a residue of a resorcinol derivative represented by a heterocyclic aryl group selected from the group consisting of General Formulae (3-1), (3-2) and (3-3):

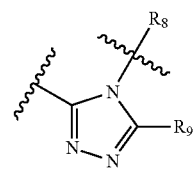

(3-1)

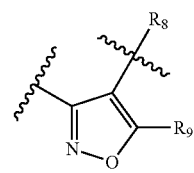

(3-2)

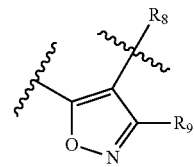

(3-3)

wherein $R_9$ represents one selected from the group consisting of a mercapto group, a hydroxyl group, a hydrogen atom, a halogen atom, a carbamoyl group, a C1-C8 alkoxycarbonyl group, a cyano group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxyl group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, and a C1-C8 alkylsilyl group.

The halogen atom for $R_7$ and $R_9$ represents a fluorine atom, a chlorine atom, a bromine atom, or an iodine atom.

The alkyl group for $R_7$ and $R_8$ represents a linear, branched or cyclic C1-C20 alkyl group. Examples of the linear alkyl group include, but not limited to, a methyl group, an ethyl group, a propyl group, a n-butyl group, a n-pentyl group, a n-hexyl group, an octyl group, a decyl group, a dodecyl group, a tetradecyl group, a hexadecyl group, an octadecyl group, and an eicosyl group. Examples of the branched alkyl group include, but not limited to, an isopropyl group, a t-butyl group, a 2,2-dimethylpropyl group, a 2,3-dimethylpentyl group, a 2,3-dimethyloctyl group, a 3-methyl-4-ethyldecyl group, and a 3,4-diethylundecyl group. Examples of the cyclic alkyl group include, but not limited to, a cyclopropyl group, a cyclobutyl group, a cyclopentyl group, a cyclohexyl group, an adamantyl group, a cyclododecyl group, a cyclohexadecyl group, a cyclooctadecyl group, and a cycloeicosyl group. The alkyl group is preferably a linear, branched or cyclic C1-C8 alkyl group.

The alkenyl group for $R_7$ and $R_8$ represents a linear, branched or cyclic C2-C20 alkenyl group having a carbon-carbon double bond at any one or more sites. Examples of the linear alkenyl group include, but not limited to, a 1-alkenyl group such as an ethenyl group, a 1-propenyl group, a 1-butenyl group, a 1-octenyl group, a 1-hexadecenyl group, or a 1-octadecyl group; and a 2-alkenyl group such as a 2-butenyl group, a 2-pentenyl group, a 2-octenyl group, a 2-hexadecenyl group, or a 2-octadecel group. Examples of the branched alkenyl group include, but not limited to, an isopropenyl group, a 3-methyl-1-butenyl group or a geranyl group, a 6-ethyl-3-methyl-1-octenyl group, and a 5,6-dimethyl-1-octadecel group. The alkenyl group is preferably a linear, branched or cyclic C2-C8 alkenyl group.

The alkynyl group for $R_7$ and $R_8$ represents a C2-C20 alkynyl group having a carbon-carbon triple bond at one or more sites. Examples include, but not limited to, a 1-alkynyl group such as an ethynyl group, a 1-propynyl group, a 3,3-dimethyl-1-butynyl group, a 1-octynyl group, a 1-hexadecynyl group, or a 1-octadecynyl group; and a 2-alkynyl group such as a 2-propynyl group, a 2-butynyl group, a 3-phenyl-2-propynyl group, a 4,4-dimethyl-2-pentynyl group, a 3-trimethylsilyl-2-propinyl group, a 2-hexynyl group, a 2-octynyl group, a 2-dodenicyl group, a 2-hexadecynyl group, or a 2-octadecynyl group. The alkynyl group is preferably a C2-C8 alkynyl group.

Examples of the carbocyclic aryl group for $R_7$ and $R_8$ include, but not limited to, a phenyl group and a naphthyl group. Furthermore, examples of the heterocyclic aryl group include, but not limited to, a pyridyl group, a pyrimidinyl group, a quinolyl group, a quinazolyl group, a naphthyridinyl group, a furyl group, a pyrrolyl group, an indolyl group, an imidazolyl group, a pyrazolyl group, an oxazolyl group, an isoxazolyl group, and a triazolyl group.

Examples of the substituent that may be carried by $R_8$ include, but not limited to, a hydrogen atom, a mercapto group, a hydroxyl group, a halogen atom, a nitro group, a cyano group, an alkyl group, an alkenyl group, an alkynyl group, a carbocyclic or heterocyclic aryl group, an alkylthio group, an arylthio group, an alkylsulfinyl group, an arylsulfinyl group, an alkylsulfonyl group, an arylsulfonyl group, a sulfamoyl group, an alkoxy group, an aryloxy group, an acyloxy group, an alkoxycarbonyloxy group, a carbamoyloxy group, an amino group, an acylamino group, an alkoxycarbonylamino group, a ureido group, a sulfonylamino group, a sulfamoylamino group, a formyl group, an acyl group, a carboxyl group, an alkoxycarbonyl group, a carbamoyl group, and a silyl group. The position of substitution on the aromatic ring may be the ortho-position, the meta-position, or the para-position.

The alkylthio group for $R_7$ and $R_9$ represents a C1-C8 alkylthio group, and examples thereof include, but not limited to, a methylthio group, an isopropylthio group, and a benzylthio group. Examples of the arylthio group include, but not limited to, a phenylthio group, a naphthylthio group, and a pyridylthio group.

The alkylsulfinyl group represents a C1-C8 alkylsulfinyl group, and examples thereof include, but not limited to, a methylsulfinyl group, an isopropylsulfinyl group, and a benzylsulfinyl group. Examples of the arylsulfinyl group include, but not limited to, a phenylsulfinyl group, a naphthylsulfinyl group, and a pyridylsulfinyl group.

The alkylsulfonyl group represents a C1-C8 alkylsulfonyl group, and examples thereof include, but not limited to, a methylsulfonyl group, an isopropylsulfonyl group, and a benzylsulfonyl group. Examples of the arylsulfonyl group include, but not limited to, a phenylsulfonyl group, a naphthylsulfonyl group, and a pyridylsulfonyl group.

Examples of the sulfamoyl group include, but not limited to, a dimethylsulfamoyl group and a phenylsulfamoyl group.

The alkoxy group for $R_7$ and $R_9$ represents a C1-C8 alkoxy group, and examples thereof include, but not limited to, a methoxy group, an isopropoxy group, and a benzyloxy group. Examples of the aryloxy group include, but not limited to, a phenoxyl group, a naphthyloxy group, and a pyridyloxy group.

The acyloxy group represents a C1-C8 acyloxy group, and examples thereof include, but not limited to, an acetoxy group and a benzoyloxy group.

The alkoxycarbonyloxy group represents a C1-C8 alkoxycarbonyloxy group, and examples thereof include, but not limited to, a methoxycarbonyloxy group and a trifluoromethoxycarbonyl group.

Examples of the carbamoyloxy group include, but not limited to, a dimethylcarbamoyloxy group and a phenylcarbamoyloxy group.

Examples of the amino group for $R_7$ and $R_9$ include, but not limited to, an unsubstituted amino group, a dimethylamino group, a morpholino group, a piperidinyl group, a 4-methylpiperazin-1-yl group, and a phenylamino group.

Examples of the acylamino group include, but not limited to, an acetylamino group and a benzoylamino group.

Examples of the alkoxycarbonylamino group include, but not limited to, a methoxycarbonylamino group, an ethoxycarbonylamino group, and a benzyloxycarbonylamino group.

Examples of the ureido group include, but not limited to, a trimethylureido group and a 1-methyl-3-phenylureido group.

Examples of the sulfonylamino group include, but not limited to a methanesulfonylamino group and a benzenesulfonylamino group.

Examples of the sulfamoylamino group include a dimethylsulfamoylamino group.

Examples of the acyl group for $R_7$ and $R_9$ include, but not limited to, an acetyl group, a pivaloyl group, a benzoyl group, and a pyridinecarbonyl group.

Examples of the alkoxycarbonyl group include, but not limited to, a methoxycarbonyl group and a benzyloxycarbonyl group.

Examples of the alkylsilyl group include, but not limited to, a trimethylsilyl group, a triisopropylsilyl group, and a t-butyldiphenylsilyl group.

Examples of the carbamoyl group for $R_7$ include, but not limited to, a dimethylcarbamoyl group and a phenylcarbamoyl group.

The alkylamino group which may have a substituent for $R_8$ represents a linear, branched or cyclic C1-C8 alkyl group having an amino group or an alkylamino group as a substituent. Examples include, but not limited to, an aminoethylene group, a morpholinomethylene group, a morpholino-3-propylene group, and a piperazino-3-propylene group.

Examples of the acylamino group which may have a substituent include an acetylamino group and a benzoylamino group.

The substituent that may be carried by $R_8$ has the same meaning as described above.

According to the present invention, a resorcinol derivative-conjugated block copolymer in which $R_3$ in General Formula (1) is a residue of a resorcinol derivative having HSP90 inhibitory activity is preferred. This will be explained below.

The present resorcinol derivative-conjugated block copolymer is a block copolymer represented by General Formula (1), in which a polyethylene glycol segment is connected with a poly(aspartic acid and/or glutamic acid) derivative segment, and $R_3$ is a residue of a resorcinol derivative. That is, the present resorcinol derivative-conjugated block copolymer is a resorcinol derivative-conjugated block copolymer represented by General Formula (1):

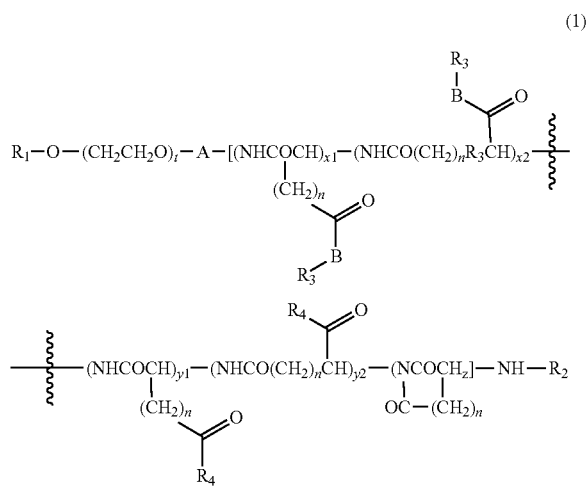
(1)

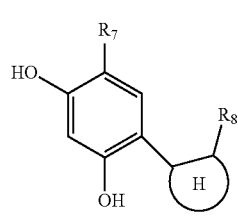
(3)

wherein $R_1$ represents a hydrogen atom or a C1-C6 alkyl group which may have a substituent; t represents an integer of 20 to 270; A represents a C1-C6 alkylene group which may have a substituent; $R_2$ represents a substituent selected from the group consisting of a hydrogen atom, a C1-C6 acyl group, and a C1-C6 alkoxycarbonyl group; $R_3$ represents a residue of a resorcinol derivative; $R_4$ represents one or more substituents selected from the group consisting of a linear, branched or cyclic C1-C30 alkoxy group which may have a substituent, a linear, branched or cyclic C1-C30 alkylamino group which may have a substituent, a linear, branched or cyclic C1-C30 dialkylamino group which may have a substituent, a C1-C8 alkylaminocarbonyl-C1-C8 alkylamino group which may have a substituent, a residue of a hydrophobic fluorescent substance, and a hydroxyl group; B represents a linking group; n represents 1 or 2; $x_1$, $x_2$, $y_1$, $y_2$ and z each independently represent an integer of 0 to 25; $(x_1+x_2)$ represents an integer of 1 to 25; $(x_1+x_2+y_1+y_2+z)$ represents an integer of 3 to 25; and the each constituent unit to which $R_3$ or $R_4$ is linked, and the constituent unit in which a side chain carbonyl group is intramolecularly cyclized are each independently randomly arranged.

Here, General Formulas $R_1$, $R_2$, $R_4$, A, B, t, $x_1$, $x_2$, $y_1$, $y_2$, and z have the same meanings as described above.

When $R_3$ of General Formula (1) is a residue of a resorcinol derivative, compounds having HSP90 inhibitory activity and having the above-mentioned triazole skeleton, isoxazole skeleton, and pyrazole skeleton are known as the resorcinol derivative. Since these have a resorcinol structure having hydroxyl groups, the compounds may be used as the present physiologically active substance. Preferably, the compounds having HSP90 inhibitory activity as described in WO 05/000300 A, WO 06/055760 A, and WO 05/018674 A, which are resorcinol derivatives having a triazole skeleton, are preferred.

The resorcinol derivative for the residue of the resorcinol derivative having HSP90 inhibitory activity of $R_3$ is preferably a resorcinol derivative which is a residue of a resorcinol derivative represented by General Formula (3):

wherein $R_7$ represents one selected from the group consisting of a mercapto group, a hydroxyl group, a halogen atom, a nitro group, a cyano group, a C1-C20 alkyl group, a C2-C20 alkenyl group, a C2-C20 alkynyl group, a carbocyclic or heterocyclic aryl group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxy group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, a carboxyl group, a C1-C8 alkoxycarbonyl group, a carbamoyl group, and a C1-C8 alkylsilyl group;

$R_8$ represents one selected from the group consisting of a carbocyclic or heterocyclic aryl group which may have a substituent, a C1-C20 alkyl group, a C2-C20 alkenyl group, a C2-C20 alkynyl group, a C1-C20 alkylamino group, and a C1-C20 acylamino group; and ring H represents a heterocyclic aryl group selected from the group consisting of General Formulae (3-1), (3-2), and (3-3):

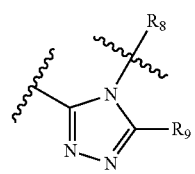
(3-1)

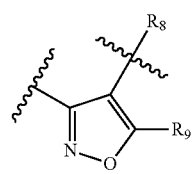
(3-2)

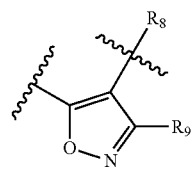
(3-3)

wherein $R_9$ represents one selected from the group consisting of a mercapto group, a hydroxyl group, a hydrogen atom, a halogen atom, a carbamoyl group, a C1-C20 alkoxycarbonyl group, a cyano group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxyl group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, and a C1-C8 alkylsilyl group.

$R_7$ to $R_9$ and ring H in General Formula (3) have the same meanings as described above.

The resorcinol derivative for the residue of the resorcinol derivative of $R_3$ is preferably a compound having a combination of $R_7$ to $R_9$ and ring H in General Formula (3) selected from the following group.

$R_7$ is preferably a halogen atom, a linear or branched C1-C8 alkyl group which may have a substituent, a linear or branched C1-C8 alkynyl group which may have a substituent, a carbamoyl group, or a sulfamoyl group, and a chlorine atom, a bromine atom, an ethyl group, an isopropyl group, and a 2-propynyl group are particularly preferred.

$R_8$ is preferably a linear or branched C1-C8 alkyl group which may have a substituent, a phenyl group which may have a substituent, a naphthyl group, a pyrrolyl group, or an indolyl group. The substituent for $R_8$ in General Formula (3) is preferably a hydroxyl group, a linear, branched or cyclic C1-C8 alkyl group, a C1-C8 alkoxy group, or an amino group which may have a substituent; and particularly preferably a hydroxyl group, a methoxy group, a morpholino group, or a 4-methylpiperazin-1-yl group.

$R_9$ is preferably a mercapto group, a hydroxyl group, an alkylsulfonyl group, a carbamoyl group, or an alkoxycarbonyl group; and particularly preferably a mercapto group or a hydroxyl group.

Ring H is preferably a triazolyl group or an isoxazolyl group.

When $R_9$ is a mercapto group or a hydroxyl group, and the ring H is a triazolyl group, tautomerization is enabled, and the respective tautomers may be employed.

Specific examples of the resorcinol derivative according to the present invention may include, but not limited to, the following eleven compounds (3a) to (3k).

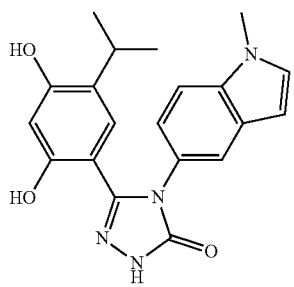
(3a)

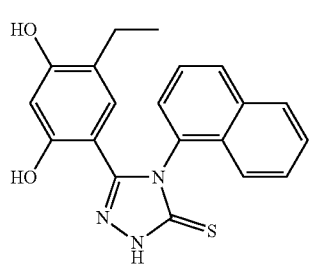
(3b)

-continued

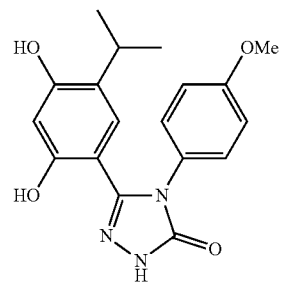
(3c)

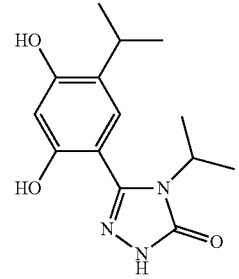
(3d)

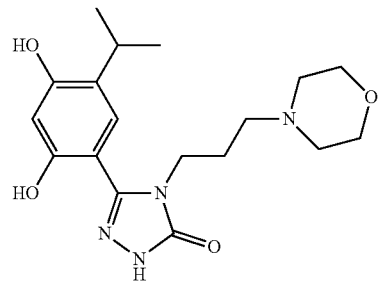
(3e)

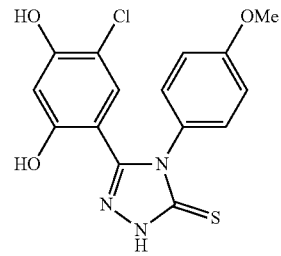
(3f)

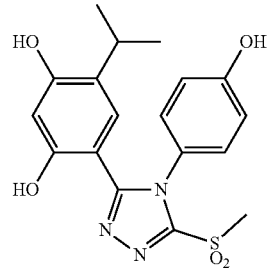
(3g)

-continued

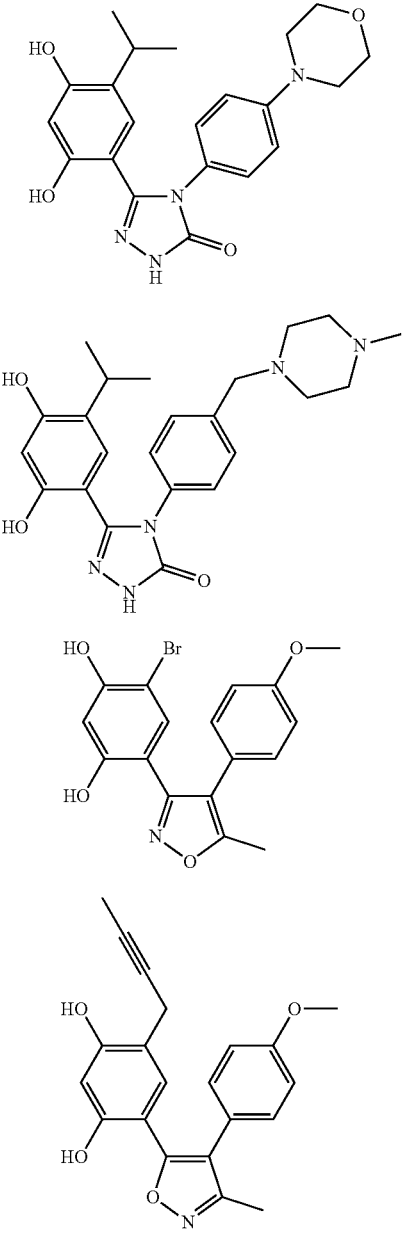

(3h)

(3i)

(3j)

(3k)

The resorcinol derivative of $R_3$ is preferably 4-isopropyl-6-(4-(1-methyl-1H-indol-5-yl)-5-methylene-4,5-dihydro-1H-1,2,4-triazol-3-yl)benzene-1,3-diol (general name: Ganetespib) of Structural Formula (3a).

The resorcinol derivative of $R_3$ of General Formula (1) is such that identical compounds may exist in the same molecule of the resorcinol-conjugated block copolymer, or plural kinds of compounds may exist as a mixture. It is preferable that $R_3$'s represent identical compound.

A preferred embodiment of the case in which the present physiologically active substance is a resorcinol derivative having HSP90 inhibitory activity, may be a resorcinol derivative-conjugated block copolymer in which a polyethylene glycol segment is connected with a polyglutamic acid derivative segment, and the side chain carboxyl group of a glutamic acid unit is linked to a resorcinol derivative. That is, it is preferable to use a polyglutamic acid segment as the polyamino acid segment of the block copolymer. That is, n in General Formula (1) is preferably 2.

A more preferred embodiment of the resorcinol derivative-conjugated block copolymer is a resorcinol derivative-conjugated block copolymer represented by General Formula (5):

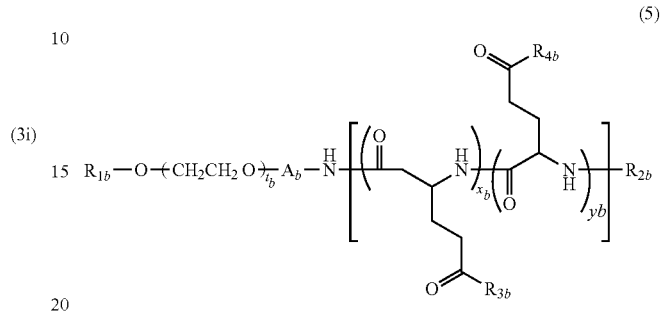

(5)

wherein $R_{1b}$ represents a hydrogen atom or a C1-C6 alkyl group which may have a substituent; $t_b$ represents an integer of 20 to 270; $A_b$ represents a C1-C6 alkylene group which may have a substituent; $x_b$ and $y_b$ are each an integer; $(x_b+y_b)$ represents an integer of 3 to 20; the proportion of $x_b$ with respect to $(x_b+y_b)$ is 1% to 100%, while the proportion of $y_b$ is 0% to 99%; $R_{2b}$ represents one selected from the group consisting of a hydrogen atom, a C1-C6 acyl group which may have a substituent, and a C1-C6 alkoxycarbonyl group which may have a substituent; $R_{3b}$ represents a residue of a resorcinol derivative having HSP90 inhibitory activity; $R_{4b}$'s may be identical or different, and represent one or more substituents selected from the group consisting of a C1-C8 alkoxy group which may have a substituent, a C1-C8 alkylamino group which may have a substituent, a di-C1-C8 alkylamino group which may have a substituent, a C1-C8 alkylaminocarbonyl-C1-C8 alkylamino group which may have a substituent, and a hydroxyl group; and the glutamic acid unit to which $R_{3b}$ is linked, and the glutamic acid unit to which $R_{4b}$ is linked are each independently polymerized in a random arrangement.

The C1-C6 alkyl group which may have a substituent for $R_{1b}$ may be a linear, branched or cyclic C1-C6 alkyl group which may have a substituent. Examples thereof include, but not limited to, a methyl group, an ethyl group, a n-propyl group, an isopropyl group, a n-butyl group, a s-butyl group, a t-butyl group, a n-pentyl group, a cyclopentyl group, a n-hexyl group, and a cyclohexyl group.

Examples of the substituent that may be carried may include, but not limited to, a halogen atom, a nitro group, a cyano group, a hydroxyl group, a mercapto group, a carbocyclic or heterocyclic aryl group, an alkylthio group, an arylthio group, an alkylsulfinyl group, an arylsulfinyl group, an alkylsulfonyl group, an arylsulfonyl group, a sulfamoyl group, an alkoxy group, an aryloxy group, an acryloxy group, an alkoxycarbonyloxy group, a carbamoyloyx group, a substituted or unsubstituted amino group, an acylamino group, an alkoxycarbonylamino group, a ureido group, a sulfonylamino group, a sulfamoylamino group, a formyl group, an acyl group, a carboxyl group, an alkoxycarbonyl group, a carbamoyl group, and a silyl group. The position of substitution on the aromatic ring may be the ortho-position, the meta-position, or the para-position.

Examples of $R_{1b}$ include, but not limited to, a methyl group, an ethyl group, a n-propyl group, an isopropyl group, a n-butyl group, a s-butyl group, a t-butyl group, a benzyl group, a 2,2-dimethoxyethyl group, a 2,2-diethoxyethyl group, and a 2-formylethyl group. A linear, branched or cyclic C1-C4 alkyl group which may have a substituent is more preferred. Particularly, a methyl group, an ethyl group, a n-propyl group, an isopropyl group, a n-butyl group, a s-butyl group, a t-butyl group, and the like are more preferred.

The C1-C6 alkylene group which may have a substituent for $A_b$ include, but not limited to, a methylene group, an ethylene group, a n-propylene group, and a n-butylene group. Regarding the substituent that may be carried, the alkylene group may include a hydroxyl group, a halogen atom, an amino group, an alkylamino group, a dialkylamino group, an alkoxy group, an aryl group, or the like.

Particularly, $A_b$ is more preferably an ethylene group or a n-propylene group.

$t_b$ in General Formula (5) represents the number of polymerized units of an ethyleneoxy group in the polyethylene glycol segment. This $t_b$ is an integer of 20 to 270. That is, the molecular weight of the polyethylene glycol segment is 0.8 kilodaltons to 12 kilodaltons. If $t_b$, which is the degree of polymerization of the polyethylene glycol segment, is smaller than 20, the resorcinol derivative-conjugated block copolymer thus obtainable does not have sufficient water-solubility, and there is a risk that desired biokinetics may not be presented. On the other hand, if $t_b$ is larger than 270, there is a risk that the total molecular weight of the resorcinol derivative-conjugated block copolymer thus obtainable becomes so large that desired biokinetics may not be presented, and thereby unexpected tissue disorders such as hematotoxicity may develop. This $t_b$ is preferably an integer of 22 to 230, and more preferably an integer of 30 to 180. That is, the molecular weight of the polyethylene glycol segment is preferably 1 kilodalton to 10 kilodaltons, and more preferably 1.3 kilodaltons to 8 kilodaltons.

The block copolymer of General Formula (5) has a polyglutamic acid derivative segment, and $(x_b+y_b)$ represents the number of polymerized units of the polyglutamic acid derivative. The number of polymerized units of the polyglutamic acid derivative is 3 to 20, that is, $(x_b+y_b)$ is an integer of 3 to 20. If the value of $(x_b+y_b)$ is smaller than 3, there is a risk that in regard to the camptothecin derivative-conjugated block copolymer thus obtainable, the laser light scattering intensity that will be described below may not fall in an optimal range. On the other hand, if the value of $(x_b+y_b)$ is larger than 20, the total molecular weight of the camptothecin derivative-conjugated block copolymer thus obtainable becomes large, and also, there is a risk that the laser light scattering intensity that will be described below may not fall in an optimal range. That is, if the value of $(x_a+y_a)$ is not in the range of 3 to 20, there is a risk that the action of enhancing the antitumor effect and/or an effect of reducing adverse effects may not be obtained. It is preferable that the number of polymerized units of the polyglutamic acid derivative is appropriately set in consideration of the total molecular weight of the camptothecin derivative-conjugated block copolymer. This $(x_b+y_b)$ is preferably an integer of 5 to 15.

$(x_b+y_b)$, which is the number of polymerized units of the polyglutamic acid derivative, may be determined by an analysis by $^1$H-NMR, or by performing neutralization titration on the polyethylene glycol-polyglutamic acid block copolymer before $R_{3b}$ and $R_{4b}$ are linked thereto.

The C1-C6 acyl group which may have a substituent for $R_{2b}$ may be a linear, branched or cyclic C1-C6 acyl group which may have a substituent. Regarding the substituent, a hydroxyl group, a halogen atom, an amino group, an alkylamino group, a dialkylamino group, an alkoxy group, an aryl group, or the like may be included. Examples of the C1-C6 acyl group for $R_{2b}$ include, but not limited to, a formyl group, an acetyl group, a trichloroacetyl group, a trifluoroacetyl group, a propionyl group, a pivaloyl group, a benzylcarbonyl group, and a phenethylcarbonyl group. A linear, branched or cyclic C1-C4 acyl group which may have a substituent is more preferred, and an acetyl group, a trichloroacetyl group, and a trifluoroacetyl group are more preferred.

The C1-C6 alkoxycarbonyl group which may have a substituent for $R_{2b}$ may be a linear, branched or cyclic C1-C6 alkoxycarbonyl group which may have a substituent. Regarding the substituent, a hydroxyl group, a halogen atom, an amino group, an alkylamino group, a dialkylamino group, an alkoxy group, an aryl group, or the like may be included. Examples of the C1-C6 alkoxycarbonyl group for $R_{2b}$ include, but not limited to, a methoxycarbonyl group, an ethoxycarbonyl group, a t-butoxycarbonyl group, a benzyloxycarbonyl group, and a 9-fluorenylmethyloxycarbonyl group.

The resorcinol derivative for the residue of the resorcinol derivative having HSP90 inhibitory activity regarding $R_{3b}$ in General Formula (5) is preferably a resorcinol derivative as a residue of a resorcinol derivative represented by General Formula (3):

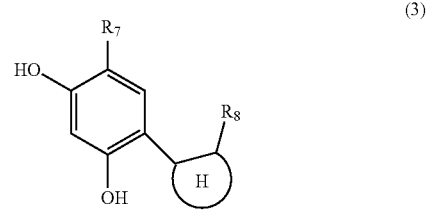

(3)

wherein $R_7$ represents one selected from the group consisting of a mercapto group, a hydroxyl group, a halogen atom, a nitro group, a cyano group, a C1-C20 alkyl group, a C2-C20 alkenyl group, a C2-C20 alkynyl group, a carbocyclic or heterocyclic aryl group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxy group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, a carboxyl group, a C1-C8 alkoxycarbonyl group, a carbamoyl group, and a C1-C8 alkylsilyl group;

$R_8$ represents one selected from the group consisting of a carbocyclic or heterocyclic aryl group which may have a substituent, a C1-C20 alkyl group, a C2-C20 alkenyl group, a C2-C20 alkynyl group, a C1-C20 alkylamino group, and a C1-C20 acylamino group; and ring H represents a heterocyclic aryl group selected from the group consisting of General Formulae (3-1), (3-2), and (3-3):

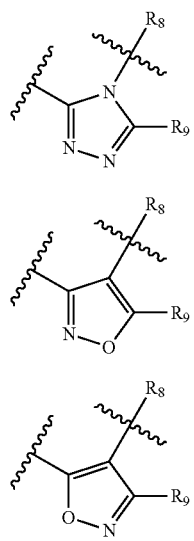

(3-1)

(3-2)

(3-3)

wherein $R_9$ represents one selected from the group consisting of a mercapto group, a hydroxyl group, a hydrogen atom, a halogen atom, a carbamoyl group, a C1-C20 alkoxycarbonyl group, a cyano group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxyl group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, and a C1-C8 alkylsilyl group.

Meanwhile, $R_5$ to $R_9$ and ring H in General Formula (3) for $R_{3b}$ have the same meanings as described above.

The bonding mode of the residue of the resorcinol derivative according to an embodiment is preferably an ester bond between a hydroxyl group of the resorcinol derivative and a side chain carboxyl group of the polyglutamic acid derivative segment. The ester bond may be formed by any one of the hydroxyl groups of the resorcinol substituents of the resorcinol derivative, or may be a mixture thereof.

The resorcinol derivative of $R_{3b}$ of General Formula (5) is preferably 4-isopropyl-6-(4-(1-methyl-1H-indol-5-yl)-5-methylene-4,5-dihydro-1H-1,2,4-triazol-3-yl)benzene-1,3-diol (general name: Ganetespib).

The resorcinol derivative of $R_{3b}$ of General Formula (5) is such that identical compounds may exist in the same molecule of the resorcinol derivative-conjugated block copolymer, or plural kinds of compounds may exist as a mixture. It is preferable that $R_{3b}$'s represent identical compounds.

In regard to General Formula (5), $x_b$ represents the total number of glutamic acid units to which the resorcinol derivative of $R_{3b}$ is linked. It is an essential configuration to have the glutamic acid unit to which the resorcinol derivative is linked, and $x_b$ is an integer of 1 or larger. Preferably, $x_b$ is an integer of 2 to 18, and more preferably an integer of 3 to 16.

The proportion of $x_b$ with respect to $(x_b+y_b)$, which is the number of polymerized units of the polyglutamic acid derivative, is 1% to 100%. The proportion of $x_b$ with respect to $(x_b+y_b)$ is preferably 10% to 90%, and more preferably 20% to 80%.

The number of bonds of the resorcinol derivative of $x_b$ may be determined by hydrolyzing the resorcinol derivative-conjugated block copolymer thus obtainable, quantitatively determining by HPLC those released resorcinol derivative molecules or fragment molecules originating therefrom, thereby calculating the content of the resorcinol derivative, and calculating the number of bonds from the value.

$R_{4b}$'s in General Formula (5) are one or more substituents selected from the group consisting of a C1-C8 alkoxy group which may have a substituent, a C1-C8 alkylamino group which may have a substituent, a di-C1-C8 alkylamino group which may have a substituent, a C1-C8 alkylaminocarbonyl-C1-C8 alkylamino group which may have a substituent, and a hydroxyl group.

This $R_{4b}$ may be optionally introduced for the purpose of controlling the physical properties of the present resorcinol derivative-conjugated block copolymer. For example, hydrophobicity of the polyglutamic acid segment of the resorcinol derivative-conjugated block copolymer may be increased by introducing a hydrophobic group into $R_{4b}$. On the other hand, when a hydrophilic substituent including an ionic functional group that is capable of forming a salt, such as an amino group, a carboxyl group, or a hydroxyl group, is introduced as $R_{4b}$, hydrophilicity of the polyglutamic acid segment of the resorcinol derivative-conjugated block copolymer may be increased. In a case in which $R_{4b}$ is a hydroxyl group, the side chain carboxyl group of the polyglutamic acid segment is a free carboxylic acid.

The substituents for $R_{4b}$ may be substituents of a single kind, or may be substituents of plural kinds.

The C1-C8 alkoxy group which may have a substituent for $R_{4b}$ may be a linear, branched or cyclic C1-C8 alkoxy group which may have a substituent. That is, this is an alkoxy group in which an ester type modifying group is linked to a side chain carboxyl group of the polyglutamic acid segment. The alkoxy group may have a hydroxyl group, a halogen atom, an amino group, an alkylamino group, a dialkylamino group, an alkoxy group, an aryl group, or the like as the substituent. Examples of the C1-C8 alkoxy group for $R_{4b}$ include, but not limited to, a methoxy group, an ethoxy group, a propoxy group, an isopropoxy group, a butoxy group, a t-butoxy group, a cyclohexyloxy group, and a benzyloxy group.

The C1-C8 alkylamino group which may have a substituent for $R_{4b}$ may be a linear, branched or cyclic C1-C8 alkylamino group which may have a substituent. That is, this is an alkylamino group in which an alkylamide type modifying group is linked to a side chain carboxyl group of the polyglutamic acid segment. The alkylamino group may include a hydroxyl group, a halogen atom, an amino group, an alkylamino group, a dialkylamino group, an alkoxy group, an aryl group, or the like as the substituent. Examples of the C1-C8 alkylamino group for $R_{4a}$ include, but not limited to, a methylamino group, an ethylamino group, a propylamino group, an isopropylamino group, a butylamino group, a t-butylamino group, a cyclohexylamino group, and a benzylamino group.

An amino acid having a protected carboxyl group is also included in the C1-C8 alkylamino group which may have a substituent. Examples of the amino acid having a protected carboxyl group that may be used include, but not limited to, glycine methyl ester, glycine benzyl ester, β-alanine methyl ester, β-alanine benzyl ester, alanine methyl ester, leucine methyl ester, and phenylalanine methyl ester.

The di-C1-C8 alkylamino group which may have a substituent for $R_{4b}$ may be a linear, branched or cyclic di-C1-C8 alkylamino group which may have a substituent. That is, this is a dialkylamino group in which a dialkylamide type modifying group is linked to a side chain carboxyl group of the polyglutamic acid segment. As the substituent, the dialkylamino group may include a hydroxyl group, a halogen atom, an amino group, an alkylamino group, a dialkylamino group, an alkoxy group, an aryl group, or the like. Examples of the di-C1-C8 alkylamino group for $R_{4b}$ include, but not limited to, a dimethylamino group, a diethylamino group, a dipropylamino group, a diisopropylamino group, a dibutylamino group, a pyrrolidino group, a piperidino group, a dibenzylamino group, and a N-benzyl-N-methylamino group.

The substituent for $R_{4b}$ may also be a C1-C8 alkylaminocarbonyl-C1-C8 alkylamino group which may have a substituent. This is a group in which a urea type modifying group is linked to a side chain carboxyl group of the polyglutamic acid segment, and which has —N($R_{4bx}$)CONH ($R_{4by}$) [wherein $R_{4bx}$ and $R_{4by}$ may be identical or different, and each represents a linear, branched or cyclic C1-C8 alkyl group which may be substituted with a tertiary amino group] as the side chain carboxyl group.

Examples of the linear, branched or cyclic C1-C8 alkyl group which may be substituted with a tertiary amino group for $R_{4bx}$ and $R_{4by}$ may include, but not limited to, a methyl group, an ethyl group, a n-propyl group, an isopropyl group, a cyclohexyl group, a 2-dimethylaminoethyl group, and a 3-dimethylaminopropyl group.

Examples of the C1-C8 alkylaminocarbonyl-C1-C8 alkylamino group which may have a substituent for $R_{4b}$ include, but not limited to, a methylaminocarbonylmethylamino group, an ethylaminocarbonylethyamino group, an isopropylaminocarbonylisopropylamino group, a cyclohexylaminocarbonylcyclohexylamino group, an ethylaminocarbonyl-(3-dimethylaminopropyl)amino group, and a (3-dimethylaminopropyl)aminocarbonylethylamino group.

$R_{4b}$ in General Formula (5) may also be a hydroxyl group. That is, the side chain carboxylic acid of glutamic acid is a free carboxylic acid. In this case, the side chain carboxylic acid may be in the form of free acid, or may be in the form of any pharmaceutically acceptable carboxylic acid salt. Examples of the carboxylic acid salt include, but not limited to, a lithium salt, a sodium salt, a potassium salt, a magnesium salt, a calcium salt, and an ammonium salt, which are included in the present invention.

$R_{4b}$ in General Formula (4) is preferably a C1-C8 alkylaminocarbonyl-C1-C8 alkylamino group and/or a hydroxyl group. That is, an embodiment in which $R_{4b}$'S include a mixture of a C1-C8 alkylaminocarbonyl-C1-C8 alkylamino group and a hydroxyl group, or an embodiment in which $R_{4b}$'s include hydroxyl groups only, is preferred.

In General Formula (4), $y_b$ represents the total number of glutamic acid units to which $R_{4b}$ is linked. The glutamic acid unit to which $R_{4b}$ is linked is an optional configuration, and $y_b$ is an integer of 0 to 19. Preferably, $y_b$ is an integer of 2 to 18, and more preferably 4 to 17.

The proportion of $y_b$ with respect to $(x_b+y_b)$, which is the number of polymerized units of the polyglutamic acid derivative, is 0% to 99%. The proportion of $y_b$ with respect to $(x_b+y_b)$ is preferably 10% to 90%, and more preferably 20% to 80%.

$y_b$, which is the number of bonds of $R_{4b}$, may be determined by measuring the resulting resorcinol derivative-conjugated block copolymer by $^1$H-NMR under alkaline conditions, and calculating $y_b$ from the signal intensity ratio.

In regard to the resorcinol derivative-conjugated block copolymer according to the present invention, the polyglutamic acid derivative segment is a polymer segment including a mixture of a glutamic acid derivative unit that includes a side chain carboxyl group and $R_{3b}$, and a glutamic acid derivative unit that includes $R_{4b}$. The glutamic acid derivative unit that includes $R_{3b}$ and the glutamic acid derivative unit that includes $R_{4b}$ may be of block polymerized type, in which the glutamic acid derivative units are arranged in a polarized manner, or may be of randomly polymerized type, in which the glutamic acid derivative units are arranged irregularly. Preferred is a randomly polymerized type polyglutamic acid derivative segment in which the glutamic acid derivative units including $R_{3b}$ and the glutamic acid derivative units including $R_{4b}$ are irregularly arranged.

The present resorcinol derivative-conjugated block copolymer has a molecular weight of from 2 kilodaltons to 15 kilodaltons. If the molecular weight is smaller than 2 kilodaltons, there is a risk that the pharmacokinetics characteristics based on macromolecularization may not be exhibited, and desired pharmacological action such as the action of enhancing an antitumor effect may not be obtained. Meanwhile, if the molecular weight is more than 15 kilodaltons, there is a risk that avoidance of adverse effects from an antitumor effect is not easily achieved, and adverse effects may be strongly presented. Particularly, resorcinol derivatives have a feature that persistence of hematotoxicity such as myelosuppression is strongly manifested. If the molecular weight is more than 15 kilodaltons, the prolonged hematotoxicity is strongly manifested. Therefore, control of the molecular weight is very important for the present resorcinol derivative-conjugated block copolymer. The molecular weight of the present resorcinol derivative-conjugated block copolymer-conjugated block copolymer is preferably from 3 kilodaltons to 12 kilodaltons, and more preferably from 3 kilodaltons to 10 kilodaltons.

Regarding the molecular weight of the resorcinol derivative-conjugated block copolymer-conjugated block copolymer according to the present invention, the calculated value obtained by summing the respective constituent molecular weight of each constituent part is employed as the "molecular weight of the resorcinol derivative-conjugated block copolymer". That is, a calculated value obtained by summing: (1) the molecular weight of the polyethylene glycol segment; (2) the molecular weight of the polyglutamic acid main chain; (3) the total molecular weight of the resorcinol derivative obtained by multiplying the molecular weight of the residue of the resorcinol derivative by the number of bonds thereof; and (4) the total molecular weight of substituents other than the resorcinol derivative obtained by multiplying the molecular weight of residues of the substituents by the number of bonds thereof, is employed as the molecular weight.

The "molecular weight of the resorcinol derivative-conjugated block copolymer" may be a molecular weight defined with an accuracy of the unit of kilodaltons. Therefore, the method for analyzing the each constituent part is not particularly limited as long as it is an analysis method with sufficient accuracy for the measurement of the molecular weight of the polyamino acid derivative to the unit of kilodaltons, and various analysis methods may be selected as appropriate. Preferable analysis method for the each constituent part will be described below.

Regarding the method for calculating the respective constituent molecular weight of the each constituent part, the constituent molecular weights may be calculated based on methods according to the description given above.

The present resorcinol derivative-conjugated block copolymer has a property of exhibiting self-associating properties in an aqueous solution. That is, the resorcinol derivative-conjugated block copolymer has a property in which when a 1 mg/mL aqueous solution of the resorcinol derivative-conjugated block copolymer is subjected to a particle size distribution analysis based on a laser light scattering method, the resorcinol derivative-conjugated block copolymer is measured as nanoparticles having a volume average particle diameter of about a few nanometers to about 20 nanometers. It is preferable that the present resorcinol derivative-conjugated block copolymer has a property in which the derivative forms nanoparticles having a volume average particle diameter of less than 20 nanometers at the maximum in a 1 mg/mL aqueous solution. In this case, a particle size distribution analysis in an aqueous solution based on pure water is employed. Preferably, the resorcinol derivative-conjugated block copolymer is characterized in that the volume average particle diameter is measured to be less than 20 nanometers by a particle size distribution analysis method based on a dynamic light scattering method using laser light, and more preferably, the block copolymer has a property in which the block copolymer is analyzed as nanoparticles having a particle size of 3 to 15 nanometers.

The volume average particle diameter according to the present invention is the particle size of the peak that exists at the largest proportion in a volume distribution that may be measured with, for example, a ZetaPotential/Particlesizer NICOMP 380 ZLS (analysis method: NICOMP method) manufactured by Particle Sizing Systems, LLC, or a particle size zeta potential analyzer, ZETASIZER NANO ZS (analysis method: NNLS method) manufactured by Malvern Instruments, Ltd.

Since the present resorcinol derivative-conjugated block copolymer is a block copolymer in which a hydrophilic polyethylene glycol segment is connected with a polyglutamic acid segment that includes a hydrophobic resorcinol derivative via an ester bond, it is considered that in an aqueous solution, the polyglutamic acid segments of a plurality of the block copolymer molecules associate with one another based on the hydrophobic interaction of the polyglutamic acid derivative segment. Consequently, it is speculated that micelle-like associated bodies having a core-shell structure are formed, in which the polyglutamic acid segment forms an inner core (core part) and the hydrophilic polyethylene glycol segment covers the periphery of the inner core and forms an outer shell layer (shell part), and these are observed as the nanoparticle described above.

The present resorcinol derivative-conjugated block copolymer needs to have a property of forming nanoparticles in an aqueous solution, for the purpose of having the antitumor effect-enhancing action and suppressing persistence of hematotoxicity.

It is effective to use the light scattering intensity obtained by using laser light, as an index for the nanoparticle-forming properties of the present resorcinol derivative-conjugated block copolymer. That is, the nanoparticle-forming properties of the resorcinol derivative-conjugated block copolymer in an aqueous solution may be checked by utilizing the laser light scattering intensity as an index. In that case, a method of checking the nanoparticle-forming properties in an aqueous solution of the camptothecin derivative-conjugated block copolymer by using toluene as a light scattering intensity standard sample, and utilizing the relative intensity with respect to toluene as an index, is effective.

The present resorcinol derivative-conjugated block copolymer is such that the laser light scattering intensity in a 1 mg/mL aqueous solution of the block copolymer is from 2 times to 50 times as a relative intensity with respect to the light scattering intensity of toluene. If the relative light scattering intensity is smaller than twice, it is implied that the resorcinol derivative-conjugated block copolymer does not have sufficient nanoparticle-forming properties, and since the drug migrating properties into a target diseased tissue such as a tumor and the properties of penetrating into the interior of tissues may not be sufficiently obtained, there is a risk that the efficacy may not be sufficiently manifested. According to the present invention, the value of the relative light scattering intensity is an index indicating that the substance has a nanoparticle-forming ability, and any value is acceptable as long as it is twice or more the light scattering intensity of toluene, without any particular limitations. That is, it is understood that even if the relative light scattering intensity is higher than 50 times, the polymer derivative has a sufficient nanoparticle-forming ability. However, in this case, the retention in vivo of the block copolymer is enhanced, and drug is delivered to tissues other than a target diseased tissue, so that there is a risk that unexpected adverse effects such as persistence of hematotoxicity may be presented. Therefore, it is necessary to control the relative light scattering intensity to be 50 times or less, and preferably 40 times or less.

Regarding the aqueous solution, the measurement of the light scattering intensity is an analyzed value obtained by using an aqueous solution prepared using pure water that does not include microparticles as an analytic sample. The aqueous solution may be optionally dissolved by means of ultrasonic irradiation during solution preparation. The aqueous solution thus prepared is preferably an aqueous solution that has been further subjected to a filtration treatment in order to remove submicron-sized microparticles.

The present resorcinol derivative-conjugated block copolymer is such that the light scattering intensity of an aqueous solution thereof is preferably 2 times to 40 times, and more preferably from 2 times to 30 times, as a relative intensity with respect to the light scattering intensity of toluene.

In regard to the method for measuring the light scattering intensity obtained by using laser light for the analysis of the nanoparticle-forming properties of the present resorcinol derivative-conjugated block copolymer, a method of using a 1 mg/mL aqueous solution of the resorcinol derivative-conjugated block copolymer as a measurement sample, and measuring the light scattering intensity with a laser light scattering photometer at a measurement temperature of 25° C., a scattering angle of 90°, and a wavelength of 632.8 nm is suitable. Examples of the measuring instrument may include, but not limited to, a dynamic light scattering photometer manufactured by Otsuka Electronics Co., Ltd., DLS-8000DL (measurement temperature: 25° C., scattering angle: 900, wavelength: 632.8 nm, ND filter: 2.5%, PH1: OPEN, PH2: SLIT).

Regarding toluene that is used as a standard substance for the measurement of light scattering intensity, any toluene may be used without particular limitations as long as the toluene has reagent-level purity. It is preferable to use toluene that has been subjected to pretreatment filtration, which is usually performed for the preparation of a sample for a light scattering analysis.

The present resorcinol derivative-conjugated block copolymer is preferably such that the mass content of the resorcinol derivative represented by General Formula (2) is from 10% by mass to 60% by mass. If the camptothecin derivative content is less than 10% by mass, since the content of the hydrophobic resorcinol derivative is small, the nanoparticle-forming properties based on hydrophobic interaction are deteriorated. On the other hand, if the content of the resorcinol derivative is larger than 60% by mass, there is a risk that the water-solubility of the resorcinol derivative-conjugated block copolymer may be markedly decreased. The mass content of the resorcinol derivative is preferably from 15% by mass to 50% by mass, and even more preferably from 15% by mass to 40% by mass.

When $R_{4b}$ in General Formula (5) is a C1-C8 alkoxy group which may have a substituent, a C1-C8 alkylamino group which may have a substituent, a di-C1-C8 alkylamino group which may have a substituent, or a C1-C8 alkylaminocarbonyl-C1-C8 alkylamino group which may have a substituent, since the linking group of $R_{4b}$ is an optional substituent, the content ratio of the substituent is 30% by mass or less. The content ratio of the substituent is preferably from 1% by mass to 20% by mass.

The mass content of the polyethylene glycol segment in the present resorcinol derivative-conjugated block copolymer is preferably from 10% by mass to 80% by mass. If the mass content of the polyethylene glycol segment is lower than 10% by mass, the resorcinol derivative-conjugated block copolymer does not have sufficient water-solubility, and therefore, there is a risk that the nanoparticle-forming properties in an aqueous solution may not be secured. On the other hand, if the mass content is larger than 80% by mass, since the mass content of the polyglutamic acid segment including the resorcinol derivative is relatively decreased, there is a risk that the nanoparticle-forming properties in an aqueous solution may not be secured. The mass content of the polyethylene glycol segment is preferably from 20% by mass to 70% by mass, and more preferably from 30% by mass to 65% by mass.

Examples of the method for producing the present resorcinol derivative-conjugated block copolymer may include, but not limited to, a method of producing the resorcinol derivative-conjugated block copolymer by a condensation reaction between a block copolymer in which a polyethylene glycol segment is connected with a polyglutamic acid segment, and a resorcinol derivative; and a method of producing the resorcinol derivative-conjugated block copolymer by linking a polymer component including a polyethylene glycol segment, to a resorcinol derivative-conjugated polyglutamic acid derivative. A method of producing in advance a block copolymer in which a polyethylene glycol segment is connected with a polyglutamic acid segment, and subjecting this block copolymer and a resorcinol derivative to a condensation reaction, is preferred.

Regarding the method of producing a block copolymer in which a polyethylene glycol segment is connected with a polyglutamic acid segment, and the method of producing the resorcinol derivative-conjugated block copolymer by subjecting the block copolymer and the resorcinol derivative to a condensation reaction, production may be carried out according to the production method for the camptothecin derivative-conjugated block copolymer described above.

The present resorcinol derivative-conjugated block copolymer may exhibit a pharmacological effect by slowly cleaving and releasing the resorcinol derivative having HSP90 inhibitory activity after being administered in vivo. Therefore, the present resorcinol derivative-conjugated block copolymer may be used as a therapeutic medicine that is used for the treatment of malignant tumor diseases or diseases attributed to abnormal proliferation of cells.

When the present resorcinol derivative-conjugated block copolymer is used as a pharmaceutical product, the dose may be definitely changed depending on the gender, age, physiological condition, disease condition, and the like of the patient. However, it is preferable to administer the resorcinol derivative-conjugated block copolymer parenterally, usually at a dose of 0.01 to 500 mg/m$^2$ (body surface area), and preferably 0.1 to 250 mg/m$^2$, in terms of the active ingredient, per day for an adult. Regarding the route of administration, it is preferable to use the resorcinol derivative-conjugated block copolymer by parenteral administration. Administration by injection is carried out by intravenous administration, intra-arterial administration, subcutaneous administration, intramuscular administration, intratumor administration, or the like.

It is preferable that the present resorcinol derivative-conjugated block copolymer is used as a pharmaceutical preparation that is conventionally used, such as an injectable preparation, a tablet, or a powder. In regard to formulation, pharmaceutically acceptable carriers that are conventionally used, for example, a binder, a lubricating agent, a disintegrant, a solvent, an excipient, a solubilizing agent, a dispersant, a stabilizer, a suspending agent, a preservative, a soothing agent, a colorant, and a fragrance may be used. In the case of an injectable liquid preparation, a solvent is usually used. Examples of the solvent include, but not limited to, water, physiological saline, a 5% glucose or mannitol solution; water-soluble organic solvents, such as glycerol, ethanol, dimethyl sulfoxide, N-methylpyrrolidone, polyethylene glycol, a chromophore; mixed liquids thereof; and mixed liquids of water and the water-soluble organic solvents. It is preferable that the resorcinol derivative-conjugated block copolymer is used after being prepared into an administrable pharmaceutical preparation using these additives for formulation.

Regarding the use of the present resorcinol derivative-conjugated block copolymer as an antitumor agent, the block copolymer is used for the treatment of malignant tumor diseases. The malignant tumor diseases that may be treated are not particularly limited, and the resorcinol derivative-conjugated block copolymer may be applied to the treatment of malignant tumor diseases such as breast cancer, non-small cell lung cancer, small cell lung cancer, colorectal cancer, non-Hodgkin's lymphoma (NHL), renal cell carcinoma, prostate cancer, hepatocarcinoma, stomach cancer, pancreatic cancer, soft tissue sarcoma, malignant skin cancer, carcinoid tumors, head and neck cancer, melanoma, ovarian cancer, cholangiocarcinoma, mesothelioma, and multiple myeloma. Particularly, the resorcinol derivative-conjugated block copolymer is adequate for the treatment of non-small cell lung cancer, cervical cancer, ovarian cancer, stomach cancer (inoperable or recurrent), colorectal cancer (inoperable or recurrent), breast cancer (inoperable or recurrent), squamous cell carcinoma, and malignant lymphoma (non-Hodgkin's lymphoma), for which resorcinol derivatives have been used for the treatment.

Another preferred embodiment of the present invention may be the block copolymer in which a taxane derivative that is used as an antitumor agent as a physiologically active substance. A taxane derivative-conjugated block copolymer that uses a taxane derivative as the physiologically active substance will be explained below.

Taxane derivatives are compounds that are bound to intracellular microtubules and thereby acquire cell proliferation inhibitory activity based on depolymerization inhibitory action, and taxane derivative are used as antitumor agents. Regarding taxane derivatives that are used as antitumor agents, paclitaxel, docetaxel, cabazitaxel, and the like are known. Since these compounds have hydroxyl groups within the taxane ring skeleton or in side chains, the compounds may be applied to the present block copolymer by using the hydroxyl groups as linking groups. That is, the block copolymer is in the form in which a hydroxyl group of a taxane derivative forms an ester bond with the side chain carboxyl group of aspartic acid and/or glutamic acid directly or via an appropriate linking group.

According to the present invention, it is preferable that a taxane derivative-conjugated block copolymer in which $R_3$ in General Formula (1) is a residue of a taxane derivative is preferred. This will be explained below.

The present taxane derivative-conjugated block copolymer is a block copolymer represented by General Formula (1), in which a polyethylene glycol segment is connected with a poly(aspartic acid and/or glutamic acid) derivative segment, and $R_3$ is a residue of a taxane derivative. That is, the present taxane derivative-conjugated block copolymer is a taxane derivative-conjugated block copolymer represented by General Formula (1):

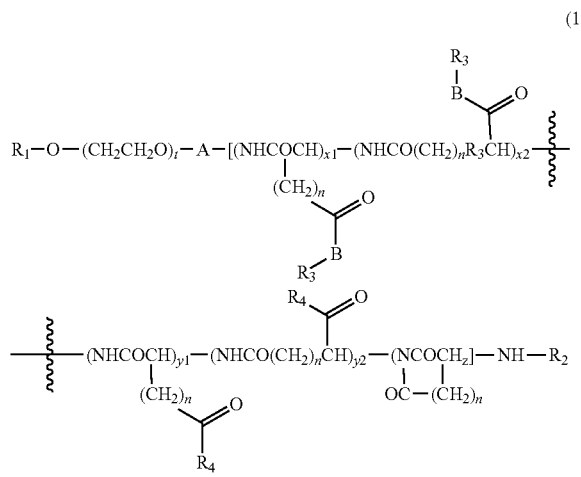

wherein $R_1$ represents a hydrogen atom or a C1-C6 alkyl group which may have a substituent; t represents an integer of 20 to 270; A represents a C1-C6 alkylene group which may have a substituent; $R_2$ represents a substituent selected from the group consisting of a hydrogen atom, a C1-C6 acyl group, and a C1-C20 alkoxycarbonyl group; $R_3$ represents a residue of a taxane derivative; $R_4$ represents one or more substituents selected from the group consisting of a linear, branched or cyclic C1-C30 alkoxy group which may have a substituent, a linear, branched or cyclic C1-C30 alkylamino group which may have a substituent, a linear, branched or cyclic C1-C30 dialkylamino group which may have a substituent, a C1-C8 alkylaminocarbonyl-C1-C8 alkylamino group which may have a substituent, a linear, branched or cyclic C1-C30 dialkylamino group which may have a substituent, a C1-C8 alkylaminocarbonyl-C1-C8 alkylamino group which may have a substituent, a residue of a hydrophobic fluorescent substance, and a hydroxyl group; B represents a linking group; n represents 1 or 2; $x_1$, $x_2$, $y_1$, $y_2$ and z each independently represent an integer of 0 to 25; ($x_1+x_2$) represents an integer of 1 to 25; ($x_1+x_2+y_1+y_2+z$) represents an integer of 3 to 25; and the each constituent unit to which $R_3$ or $R_4$ is linked, and the constituent unit in which a side chain carbonyl group is intramolecularly cyclized are each independently randomly arranged.

Here, General Formulas $R_1$, $R_2$, $R_4$, A, B, t, $x_1$, $x_2$, $y_1$, $y_2$, and z have the same meanings as described above.

When $R_3$ of General Formula (1) is a residue of a taxane derivative, known examples of the taxane derivative include paclitaxel, docetaxel, and cabazitaxel. Since these have hydroxyl groups on the taxane ring and in side chains, the derivatives may be used as the present physiologically active substance.

A preferred embodiment of the case in which the present physiologically active substance is a taxane derivative, may be a taxane derivative-conjugated block copolymer in which a polyethylene glycol segment is connected with a polyaspartic acid derivative segment, and the side chain carboxyl group of a aspartic acid unit is linked to a taxane derivative. That is, it is preferable to use a polyaspartic acid segment as the polyamino acid segment of the block copolymer. Meanwhile, the polyaspartic acid segment may be an α-form polymerized polyaspartic acid segment, a β-form polymerized polyaspartic acid segment, or an α-β mixed type polymerized polyaspartic acid segment. That is, n in General Formula (1) is preferably 1.

A more preferred embodiment of the taxane derivative-conjugated block copolymer is a taxane derivative-conjugated block copolymer represented by General Formula (6):

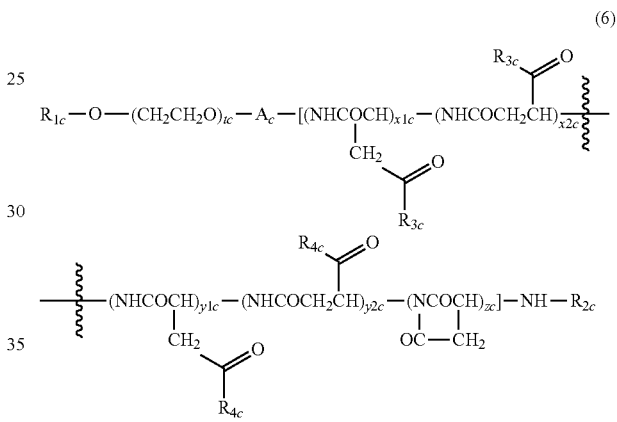

wherein $R_{1c}$ represents a hydrogen atom or a C1-C6 alkyl group which may have a substituent; $t_c$ represents an integer of 20 to 270; $A_c$ represents a C1-C6 alkylene group which may have a substituent; $x_{1c}$, $x_{2c}$, $y_{1c}$, $y_{2c}$, and $z_c$ each represent an integer; ($x_{1c}+x_{2c}+y_{1c}+y_{2c}+z_c$) represents an integer of 3 to 25; the proportion of ($x_{1c}+x_{2c}$) with respect to ($x_{1c}+x_{2c}+y_{1c}+y_{2c}+z_c$) is 1% to 100%, while the proportion of ($y_{1c}+y_{2c}+z_c$) is 0% to 99%; $R_{2c}$ represents one selected from the group consisting of a hydrogen atom, a C1-C6 acyl group which may have a substituent, and a C1-C6 alkoxycarbonyl group which may have a substituent; $R_{3c}$ represents a residue of a taxane derivative; $R_{4c}$'s may be identical or different, and represent one or more substituents selected from the group consisting of a C1-C8 alkoxy group which may have a substituent, a C1-C8 alkylamino group which may have a substituent, a di-C1-C8 alkylamino group which may have a substituent, a C1-C8 alkylaminocarbonyl-C1-C8 alkylamino group which may have a substituent, and a hydroxyl group; and the aspartic acid unit to which $R_{3c}$ is linked, and the aspartic acid unit to which $R_{4c}$ is linked are each independently polymerized in a random arrangement.

The C1-C6 alkyl group which may have a substituent for $R_{1c}$ may be a linear, branched or cyclic C1-C6 alkyl group which may have a substituent. Examples thereof include, but not limited to, a methyl group, an ethyl group, a n-propyl group, an isopropyl group, a n-butyl group, a s-butyl group, a t-butyl group, a n-pentyl group, a cyclopentyl group, a n-hexyl group, and a cyclohexyl group.

Examples of the substituent that may be carried may include, but not limited to, a halogen atom, a nitro group, a cyano group, a hydroxyl group, a mercapto group, a carbocyclic or heterocyclic aryl group, an alkylthio group, an arylthio group, an alkylsulfinyl group, an arylsulfinyl group, an alkylsulfonyl group, an arylsulfonyl group, a sulfamoyl group, an alkoxy group, an aryloxy group, an acryloxy group, an alkoxycarbonyloxy group, a carbamoyloyx group, a substituted or unsubstituted amino group, an acylamino group, an alkoxycarbonylamino group, a ureido group, a sulfonylamino group, a sulfamoylamino group, a formyl group, an acyl group, a carboxyl group, an alkoxycarbonyl group, a carbamoyl group, and a silyl group. The position of substitution on the aromatic ring may be the ortho-position, the meta-position, or the para-position.

Examples of $R_{1c}$ include, but not limited to, a methyl group, an ethyl group, a n-propyl group, an isopropyl group, a n-butyl group, a s-butyl group, a t-butyl group, a benzyl group, a 2,2-dimethoxyethyl group, a 2,2-diethoxyethyl group, and a 2-formylethyl group. A linear, branched or cyclic C1-C4 alkyl group which may have a substituent is more preferred. Particularly, a methyl group, an ethyl group, a n-propyl group, an isopropyl group, a n-butyl group, a s-butyl group, a t-butyl group, and the like are more preferred.

The C1-C6 alkylene group which may have a substituent for $A_c$ include, but not limited to, a methylene group, an ethylene group, a n-propylene group, and a n-butylene group. Regarding the substituent that may be carried, the alkylene group may include a hydroxyl group, a halogen atom, an amino group, an alkylamino group, a dialkylamino group, an alkoxy group, an aryl group, or the like. Particularly, $A_c$ is more preferably an ethylene group or a n-propylene group.

The $t_c$ represents the number of polymerized units of an ethyleneoxy group in the polyethylene glycol segment. This $t_c$ is an integer of 20 to 270. That is, the molecular weight of the polyethylene glycol segment is 0.8 kilodaltons to 12 kilodaltons. If $t_c$, which is the degree of polymerization of the polyethylene glycol segment, is smaller than 20, the taxane derivative-conjugated block copolymer thus obtainable does not have sufficient water-solubility, and there is a risk that desired biokinetics may not be presented. On the other hand, if $t_c$ is larger than 270, there is a risk that the total molecular weight of the taxane derivative-conjugated block copolymer thus obtainable becomes so large that desired biokinetics may not be presented, and thereby unexpected tissue disorders may develop. This $t_c$ is preferably an integer of 22 to 230, and more preferably an integer of 30 to 180. That is, the molecular weight of the polyethylene glycol segment is preferably 1 kilodalton to 10 kilodaltons, and more preferably 1.3 kilodaltons to 8 kilodaltons.

The block copolymer of General Formula (6) has a polyaspartic acid derivative segment, and $(x_{1c}+x_{2c}+y_{1c}+y_{2c}+z_c)$ represents the number of polymerized units of the polyglutamic acid derivative. The number of polymerized units of the polyaspartic acid derivative is 3 to 25, that is, $(x_{1c}+x_{2c}+y_{1c}+y_{2c}+z_c))$ is an integer of 3 to 25. If the value of $(x_{1c}+x_{2c}+y_{1c}+y_{2c}+z_c)$ is smaller than 3, there is a risk that in regard to the taxane derivative-conjugated block copolymer thus obtainable, the laser light scattering intensity that will be described below may not fall in an optimal range. On the other hand, if the value of $(x_{1c}+x_{2c}+y_{1c}+y_{2c}+z_c)$ is larger than 25, the total molecular weight of the taxane derivative-conjugated block copolymer thus obtainable becomes large, and also, there is a risk that the laser light scattering intensity that will be described below may not fall in an optimal range. That is, if the value of $(x_{1c}+x_{2c}+y_{1c}+y_{2c}+z_c)$ is not in the range of 3 to 25, there is a risk that the action of enhancing the antitumor effect and/or an effect of reducing adverse effects may not be obtained. It is preferable that the number of polymerized units of the polyaspartic acid derivative is appropriately set in consideration of the total molecular weight of the taxane derivative-conjugated block copolymer. This $(x_{1c}+x_{2c}+y_{1c}+y_{2c}+z_c)$ is preferably an integer of 5 to 20.

$(x_{1c}+x_{2c}+y_{1c}+y_{2c}+z_c)$, which is the number of polymerized units of the polyaspartic acid derivative, may be determined by an analysis by $^1$H-NMR, or by performing neutralization titration on the polyethylene glycol-polyaspartic acid block copolymer before $R_{3c}$ and $R_{4c}$ are linked thereto.

The C1-C6 acyl group which may have a substituent for $R_{2c}$ may be a linear, branched or cyclic C1-C6 acyl group which may have a substituent. Regarding the substituent, a hydroxyl group, a halogen atom, an amino group, an alkylamino group, a dialkylamino group, an alkoxy group, an aryl group, or the like may be included. Examples of the C1-C6 acyl group for $R_{2c}$ include, but not limited to, a formyl group, an acetyl group, a trichloroacetyl group, a trifluoroacetyl group, a propionyl group, a pivaloyl group, a benzylcarbonyl group, and a phenethylcarbonyl group. A linear, branched or cyclic C1-C4 acyl group which may have a substituent is more preferred, and an acetyl group, a trichloroacetyl group, and a trifluoroacetyl group are more preferred.

The C1-C6 alkoxycarbonyl group which may have a substituent for $R_{2c}$ may be a linear, branched or cyclic C1-C6 alkoxycarbonyl group which may have a substituent. Regarding the substituent, a hydroxyl group, a halogen atom, an amino group, an alkylamino group, a dialkylamino group, an alkoxy group, an aryl group, or the like may be included. Examples of the C1-C6 alkoxycarbonyl group for $R_{2c}$ include, but not limited to, a methoxycarbonyl group, an ethoxycarbonyl group, a t-butoxycarbonyl group, a benzyloxycarbonyl group, and a 9-fluorenylmethyloxycarbonyl group.

The taxane derivative for the residue of the taxane derivative of $R_{3c}$ is preferably one or more selected from the group consisting of paclitaxel, docetaxel, and cabazitaxel. The taxane derivatives have hydroxyl groups within the taxane ring skeleton and in side chains. The bonding mode of the taxane derivative of $R_{3c}$ is not particularly limited, and it is desirable that any one hydroxyl group of such a taxane derivative forms an ester bond with the side chain carboxyl group of polyaspartic acid.

The taxane derivative of $R_{3c}$ is such that identical compounds may exist in the same molecule of the taxane derivative-conjugated block copolymer, or plural kinds of compounds may exist as a mixture. It is preferable that $R_{3c}$'s represent identical compounds.

In regard to General Formula (6), $(x_{1c}+x_{2c})$ represents the total number of aspartic acid units to which the taxane derivative of $R_{3c}$ is linked. It is an essential configuration to have an amino acid unit to which the taxane derivative is linked, and $(x_{1c}+x_{2c})$ is an integer of 1 or larger. Preferably, $(x_{1c}+x_{2c})$ is an integer of 2 to 20, and more preferably an integer of 2 to 15.

The proportion of $(x_{1c}+x_{2c})$ with respect to $(x_{1c}+x_{2c}+y_{1c}+y_{2c}+z_c)$, which is the number of polymerized units of the polyamino acid derivative, is 1% to 100%. The proportion of $(x_{1c}+x_{2c})$ with respect to $(x_{1c}+x_{2c}+y_{1c}+y_{2c}+z_c)$ is preferably 5% to 80%, and more preferably 5% to 60%.

The number of bonds of the taxane derivative of $(x_{1c}+x_{2c})$ may be determined by hydrolyzing the taxane derivative-conjugated block copolymer thus obtainable, quantitatively determining by HPLC those released taxane derivative molecules or fragment molecules originating therefrom, thereby calculating the content of the taxane derivative, and calculating the number of bonds from the value. Furthermore, the content of the taxane derivative may be calculated from the reaction ratio of the taxane derivative when the taxane derivative-conjugated block copolymer is produced, and the number of bonds may be calculated from the value.

$R_{4c}$'s are one or more substituents selected from the group consisting of a C1-C8 alkoxy group which may have a substituent, a C1-C8 alkylamino group which may have a substituent, a di-C1-C8 alkylamino group which may have a substituent, a C1-C8 alkylaminocarbonyl-C1-C8 alkylamino group which may have a substituent, and a hydroxyl group.

This $R_{4c}$ may be optionally introduced for the purpose of controlling the physical properties of the present taxane derivative-conjugated block copolymer. For example, hydrophobicity of the polyamino acid segment of the taxane derivative-conjugated block copolymer may be increased by introducing a hydrophobic group into $R_{4c}$. On the other hand, when a hydrophilic substituent including an ionic functional group that is capable of forming a salt, such as an amino group, a carboxyl group, or a hydroxyl group, is introduced as $R_{4c}$, hydrophilicity of the polyamino acid segment of the taxane derivative-conjugated block copolymer may be increased. In a case in which $R_{4c}$ is a hydroxyl group, the side chain carboxyl group of the polyaspartic acid segment is a free carboxylic acid.

The substituents for $R_{4c}$ may be substituents of a single kind, or may be substituents of plural kinds.

The C1-C8 alkoxy group which may have a substituent for $R_{4c}$ may be a linear, branched or cyclic C1-C8 alkoxy group which may have a substituent. That is, this is an alkoxy group in which an ester type modifying group is linked to a side chain carboxyl group of the polyglutamic acid segment. The alkoxy group may have a hydroxyl group, a halogen atom, an amino group, an alkylamino group, a dialkylamino group, an alkoxy group, an aryl group, or the like as the substituent. Examples of the C1-C8 alkoxy group for $R_{4c}$ include, but not limited to, a methoxy group, an ethoxy group, a propoxy group, an isopropoxy group, a butoxy group, a t-butoxy group, a cyclohexyloxy group, and a benzyloxy group.

The C1-C8 alkylamino group which may have a substituent for $R_{4c}$ may be a linear, branched or cyclic C1-C8 alkylamino group which may have a substituent. That is, this is an alkylamino group in which an alkylamide type modifying group is linked to a side chain carboxyl group of the polyaspartic acid segment. The alkylamino group may include a hydroxyl group, a halogen atom, an amino group, an alkylamino group, a dialkylamino group, an alkoxy group, an aryl group, or the like as the substituent. Examples of the C1-C8 alkylamino group for $R_{4c}$ include, but not limited to, a methylamino group, an ethylamino group, a propylamino group, an isopropylamino group, a butylamino group, a t-butylamino group, a cyclohexylamino group, and a benzylamino group.

An amino acid having a protected carboxyl group is also included in the C1-C8 alkylamino group which may have a substituent. Examples of the amino acid having a protected carboxyl group that may be used include, but not limited to, glycine methyl ester, glycine benzyl ester, β-alanine methyl ester, β-alanine benzyl ester, alanine methyl ester, leucine methyl ester, and phenyalanine methyl ester.

The di-C1-C8 alkylamino group which may have a substituent for $R_{4c}$ may be a linear, branched or cyclic di-C1-C8 alkylamino group which may have a substituent. That is, this is a dialkylamino group in which a dialkylamide type modifying group is linked to a side chain carboxyl group of the polyaspartic acid segment. As the substituent, the dialkylamino group may include a hydroxyl group, a halogen atom, an amino group, an alkylamino group, a dialkylamino group, an alkoxy group, an aryl group, or the like. Examples of the di-C1-C8 alkylamino group for $R_{4c}$ include, but not limited to, a dimethylamino group, a diethylamino group, a dipropylamino group, a diisopropylamino group, a dibutylamino group, a pyrrolidino group, a piperidino group, a dibenzylamino group, and a N-benzyl-N-methylamino group.

The substituent for $R_{4c}$ may also be a C1-C8 alkylaminocarbonyl-C1-C8 alkylamino group which may have a substituent. This is a group in which a urea type modifying group is linked to a side chain carboxyl group of the polyaspartic acid segment, and which has —N($R_{4cx}$)CONH($R_{4cy}$) [wherein $R_{4cx}$ and $R_{4cy}$ may be identical or different, and each represents a linear, branched or cyclic C1-C8 alkyl group which may be substituted with a tertiary amino group] as the side chain carboxyl group.

Examples of the linear, branched or cyclic C1-C8 alkyl group which may be substituted with a tertiary amino group for $R_{4cx}$ and $R_{4cy}$ may include, but not limited to, a methyl group, an ethyl group, a n-propyl group, an isopropyl group, a cyclohexyl group, a 2-dimethylaminoethyl group, and a 3-dimethylaminopropyl group.

Examples of the C1-C8 alkylaminocarbonyl-C1-C8 alkylamino group which may have a substituent for $R_{4c}$ include, but not limited to, a methylaminocarbonylmethylamino group, an ethylaminocarbonylethyamino group, an isopropylaminocarbonylisopropylamino group, a cyclohexylaminocarbonylcyclohexylamino group, an ethylaminocarbonyl-(3-dimethylaminopropyl)amino group, and a (3-dimethylaminopropyl)aminocarbonylethylamino group.

$R_{4c}$ in General Formula (6) may also be a hydroxyl group. That is, the side chain carboxylic acid of the amino acid is a free carboxylic acid. In this case, the side chain carboxylic acid may be in the form of free acid, or may be in the form of any pharmaceutically acceptable carboxylic acid salt. Examples of the carboxylic acid salt include, but not limited to, a lithium salt, a sodium salt, a potassium salt, a magnesium salt, a calcium salt, and an ammonium salt, which are included in the present invention.

$R_{4c}$ in General Formula (6) is preferably a C1-C8 alkylaminocarbonyl-C1-C8 alkylamino group and/or a hydroxyl group. That is, an embodiment in which $R_{4c}$'s include a mixture of a C1-C8 alkylaminocarbonyl-C1-C8 alkylamino group and a hydroxyl group, or an embodiment in which $R_{4c}$'s include hydroxyl groups only, is preferred.

In General Formula (6), $(y_{1c}+y_{2c})$ represents the total number of aspartic acid units to which $R_{4c}$ is linked. The aspartic acid unit to which $R_{4c}$ is linked is an optional configuration, and $(y_{1c}+y_{2c})$ is an integer of 0 to 24. Preferably, $(y_{1c}+y_{2c})$ is an integer of 5 to 24, and more preferably 10 to 24.

The proportion of $(y_{1c}+y_{2c})$ with respect to $(x_{1c}+x_{2c}+y_{1c}+y_{2c}+z_c)$, which is the number of polymerized units of the polyaspartic acid derivative, is 0% to 99%. The proportion of $(y_{1c}+y_{2c})$ with respect to $(x_{1c}+x_{2c}+y_{1c}+y_{2c}+z_c)$ is preferably 10% to 95%, and more preferably 30% to 95%.

Furthermore, $z_c$ is the total number of aspartic acid constituent unit in which the side chain carbonyl group has been intramolecularly cyclized, and is an optional configuration. This z is the balance obtained by subtracting the aspartic acid constituent units to which $R_{3c}$ and $R_{4c}$ are linked, from the number of polymerized units of the polyaspartic acid derivative.

Therefore, regarding $(y_{1c}+y_{2c}+z_c)$, which is the total number of aspartic acid constituent units other than the aspartic acid units to which $R_{4c}$ including the residue of a taxane derivative is linked, the proportion with respect to the total number of polymerized units of the polyaspartic acid derivative segment is 0% to 99%, preferably 20% to 95%, and more preferably 40% to 95%.

In regard to the taxane derivative-conjugated block copolymer represented by General Formula (6), the polyaspartic acid derivative segment is a polymer segment including a mixture of an aspartic acid derivative unit that includes $R_{3c}$ as a side chain carboxyl group, an aspartic acid derivative unit that includes $R_{4c}$, and an aspartic acid unit in which the side chain carbonyl group has been intramolecularly cyclized. The aspartic acid derivative unit that includes $R_{3c}$, the aspartic acid derivative unit that includes $R_{4c}$, and the aspartic acid unit in which the side chain carbonyl group has been intramolecularly cyclized may be arranged in a polarized manner, or may be of randomly polymerized type, in which the aspartic acid derivative units are arranged irregularly. Preferred is a randomly polymerized type polyaspartic acid derivative segment in which the amino acid derivative units that include $R_{3c}$, the amino acid derivative units that include $R_{4c}$, and the aspartic acid units in which the side chain carbonyl group has been intramolecularly cyclized, are irregularly arranged.

The present taxane derivative-conjugated block copolymer has a molecular weight of from 2 kilodaltons to 15 kilodaltons. If the molecular weight is smaller than 2 kilodaltons, there is a risk that the pharmacokinetics characteristics based on macromolecularization may not be exhibited, and desired pharmacological action such as the action of enhancing an antitumor effect may not be obtained. Meanwhile, if the molecular weight is more than 15 kilodaltons, there is a risk that avoidance of adverse effects from an antitumor effect is not easily achieved, and adverse effects may be strongly presented. Particularly, taxane derivatives have a feature that prolonged hematotoxicity such as myelosuppression is strongly manifested. In a case in which the molecular weight is more than 15 kilodaltons, prolonged hematotoxicity is strongly manifested. Therefore, control of the molecular weight is very important for the present taxane derivative-conjugated block copolymer. The molecular weight of the present taxane derivative-conjugated block copolymer is preferably from 3 kilodaltons to 15 kilodaltons, and more preferably from 3 kilodaltons to 12 kilodaltons.

Regarding the molecular weight of the taxane derivative-conjugated block copolymer according to the present invention, the calculated value obtained by summing the respective constituent molecular weight of each constituent part is employed as the "molecular weight of the taxane derivative-conjugated block copolymer". That is, a calculated value obtained by summing: (1) the molecular weight of the polyethylene glycol segment; (2) the molecular weight of the polyaspartic acid main chain; (3) the total molecular weight of the taxane derivative obtained by multiplying the molecular weight of the residue of the taxane derivative by the number of bonds thereof; and (4) the total molecular weight of substituents other than the taxane derivative obtained by multiplying the molecular weight of residues of the substituents by the number of bonds thereof, is employed as the molecular weight.

The "molecular weight of the taxane derivative-conjugated block copolymer" may be a molecular weight defined with an accuracy of the unit of kilodaltons. Therefore, the method for analyzing the each constituent part is not particularly limited as long as it is an analysis method with sufficient accuracy for the measurement of the molecular weight of the polyamino acid derivative to the unit of kilodaltons, and various analysis methods may be selected as appropriate. Preferable analysis method for the each constituent part will be described below.

Regarding the method for calculating the respective constituent molecular weight of the each constituent part, the constituent molecular weights may be calculated based on methods according to the description given above.

The present taxane derivative-conjugated block copolymer has a property of exhibiting self-associating properties in an aqueous solution. That is, the taxane derivative-conjugated block copolymer has a property in which when a 1 mg/mL aqueous solution of the taxane derivative-conjugated block copolymer is subjected to a particle size distribution analysis based on a laser light scattering method, the taxane derivative-conjugated block copolymer is measured as nanoparticles having a volume average particle diameter of about a few nanometers to about 20 nanometers. It is preferable that the present taxane derivative-conjugated block copolymer has a property in which the derivative forms nanoparticles having a volume average particle diameter of less than 20 nanometers at the maximum in a 1 mg/mL aqueous solution. In this case, a particle size distribution analysis in an aqueous solution based on pure water is employed. Preferably, the taxane derivative-conjugated block copolymer is characterized in that the volume average particle diameter is measured to be less than 20 nanometers by a particle size distribution analysis method based on a dynamic light scattering method using laser light, and more preferably, the block copolymer has a property in which the block copolymer is analyzed as nanoparticles having a particle size of 3 to 15 nanometers.

The volume average particle diameter according to the present invention is the particle size of the peak that exists at the largest proportion in a volume distribution that may be measured with, for example, a ZetaPotential/Particlesizer NICOMP 380 ZLS (analysis method: NICOMP method) manufactured by Particle Sizing Systems, LLC, or a particle size zeta potential analyzer, ZETASIZER NANO ZS (analysis method: NNLS method) manufactured by Malvern Instruments, Ltd.

Since the present taxane derivative-conjugated block copolymer is a block copolymer in which a hydrophilic polyethylene glycol segment is connected with a polyaspartic acid segment that includes a hydrophobic taxane derivative via an ester bond, it is considered that in an aqueous solution, the polyaspartic acid segments of a plurality of the block copolymer molecules associate with one another based on the hydrophobic interaction of the polyaspartic acid derivative segment. Consequently, it is speculated that micelle-like associated bodies having a core-shell structure are formed, in which the polyaspartic acid segment forms an inner core (core part) and the hydrophilic polyethylene glycol segment covers the periphery of the inner core and forms an outer shell layer (shell part), and these are observed as the nanoparticle described above.

The present taxane derivative-conjugated block copolymer needs to have a property of forming nanoparticles in an aqueous solution, for the purpose of enhancing the efficacy of the taxane derivative and/or reducing adverse effects.

It is effective to use the light scattering intensity obtained by using laser light, as an index for the nanoparticle-forming properties of the present taxane derivative-conjugated block copolymer. That is, the nanoparticle-forming properties of the taxane derivative-conjugated block copolymer in an aqueous solution may be checked by utilizing the laser light scattering intensity as an index. In that case, a method of checking the nanoparticle-forming properties in an aqueous solution of the taxane derivative-conjugated block copolymer by using toluene as a light scattering intensity standard sample, and utilizing the relative intensity with respect to toluene as an index, is effective.

The present taxane derivative-conjugated block copolymer is such that the laser light scattering intensity in a 1 mg/mL aqueous solution of the block copolymer is at least 2 times or more as a relative intensity with respect to the light scattering intensity of toluene. If the relative light scattering intensity is smaller than twice, it is implied that the taxane derivative-conjugated block copolymer does not have sufficient nanoparticle-forming properties, and since the properties of penetrating into a target tissue may not be sufficiently obtained, there is a risk that adverse effects may be presented. According to the present invention, the value of the relative light scattering intensity is an index indicating that the substance has a nanoparticle-forming ability, and any value is acceptable as long as it is twice or more the light scattering intensity of toluene, without any particular limitations. That is, it is understood that even if the relative light scattering intensity is higher than 100 times, the polymer derivative has a sufficient nanoparticle-forming ability.

The present taxane compound-conjugated block copolymer is such that the light scattering intensity of an aqueous solution thereof is preferably 2 times to 70 times, and more preferably from 2 times to 50 times, as a relative intensity with respect to the light scattering intensity of toluene.

Regarding the aqueous solution, the measurement of the light scattering intensity is an analyzed value obtained by using an aqueous solution prepared using pure water that does not include microparticles as an analytic sample. The aqueous solution may be optionally dissolved by means of ultrasonic irradiation during solution preparation. The aqueous solution thus prepared is preferably an aqueous solution that has been further subjected to a filtration treatment in order to remove submicron-sized microparticles.

In regard to the method for measuring the light scattering intensity obtained by using laser light for the analysis of the nanoparticle-forming properties of the present taxane derivative-conjugated block copolymer, a method of using a 1 mg/mL aqueous solution of the taxanederivative-conjugated block copolymer as a measurement sample, and measuring the light scattering intensity with a laser light scattering photometer at a measurement temperature of 25° C., a scattering angle of 90°, and a wavelength of 632.8 nm is suitable. Examples of the measuring instrument may include, but not limited to, a dynamic light scattering photometer manufactured by Otsuka Electronics Co., Ltd., DLS-8000DL (measurement temperature: 25° C., scattering angle: 900, wavelength: 632.8 nm, ND filter: 2.5%, PH1: OPEN, PH2: SLIT).

Regarding toluene that is used as a standard substance for the measurement of light scattering intensity, any toluene may be used without particular limitations as long as the toluene has reagent-level purity. It is preferable to use toluene that has been subjected to pretreatment filtration, which is usually performed for the preparation of a sample for a light scattering analysis.

The present taxane derivative-conjugated block copolymer is preferably such that the mass content of the taxane derivative represented by $R_{3c}$ in General Formula (6) is from 10% by mass to 60% by mass. If the taxane derivative content is less than 10% by mass, since the content of the hydrophobic taxane derivative is small, the nanoparticle-forming properties based on hydrophobic interaction are deteriorated. On the other hand, if the content of the taxane derivative is larger than 60% by mass, there is a risk that the water-solubility of the taxane derivative-conjugated block copolymer may be markedly decreased. The mass content of the taxane derivative is preferably from 10% by mass to 50% by mass, and even more preferably from 10% by mass to 40% by mass.

In regard to the present taxane derivative-conjugated block copolymer, when $R_{4c}$ in General Formula (6) is a C1-C8 alkoxy group which may have a substituent, a C1-C8 alkylamino group which may have a substituent, a di-C1-C8 alkylamino group which may have a substituent, or a C1-C8 alkylaminocarbonyl-C1-C8 alkylamino group which may have a substituent, since the linking group of $R_{4c}$ is an optional substituent, the content ratio of the substituent is 30% by mass or less. The content ratio of the substituent is preferably from 1% by mass to 20% by mass.

The mass content of the polyethylene glycol segment in the present taxane derivative-conjugated block copolymer is preferably from 10% by mass to 80% by mass. If the mass content of the polyethylene glycol segment is lower than 10% by mass, the taxane derivative-conjugated block copolymer does not have sufficient water-solubility, and therefore, there is a risk that the nanoparticle-forming properties in an aqueous solution may not be secured. On the other hand, if the mass content is larger than 80% by mass, since the mass content of the polyaspartic acid segment including the taxane derivative is relatively decreased, there is a risk that the nanoparticle-forming properties in an aqueous solution may not be secured. The mass content of the polyethylene glycol segment is preferably from 20% by mass to 70% by mass, and more preferably from 30% by mass to 65% by mass.

Examples of the method for producing the present taxane derivative-conjugated block copolymer may include, but not limited to, a method of producing the taxane derivative-conjugated block copolymer by a condensation reaction between a block copolymer in which a polyethylene glycol segment is connected with a polyaspartic acid segment, and a taxane derivative; and a method of producing the taxane derivative-conjugated block copolymer by linking a polymer component including a polyethylene glycol segment, to a taxane derivative-conjugated polyaspartic acid derivative. A method of producing in advance a block copolymer in which a polyethylene glycol segment is connected with a polyaspartic acid segment, and subjecting this block copolymer and a taxane derivative to a condensation reaction, is preferred.

Regarding the method of producing a block copolymer in which a polyethylene glycol segment is connected with a polyaspartic acid segment, and the method of producing the taxane derivative-conjugated block copolymer by subjecting the block copolymer and the taxane derivative to a condensation reaction, production may be carried out according to the production method for the camptothecin derivative-conjugated block copolymer described above.

The present taxane derivative-conjugated block copolymer may exhibit a pharmacological effect by slowly cleaving and releasing the taxane derivative after being administered in vivo. Therefore, the present taxane derivative-conjugated block copolymer may be used as an antitumor agent that is used for the treatment of malignant tumor diseases.

When the present taxane derivative-conjugated block copolymer is used as an antitumor agent, the dose may be definitely changed depending on the gender, age, physiological condition, disease condition, and the like of the patient. However, it is preferable to administer the taxane derivative-conjugated block copolymer parenterally, usually at a dose of 0.01 to 500 mg/m$^2$ (body surface area), and preferably 0.1 to 250 mg/m$^2$, in terms of the active ingredient, per day for an adult. Regarding the route of administration, it is preferable to use the taxane derivative-conjugated block copolymer by parenteral administration. Administration by injection is carried out by intravenous administration, intra-arterial administration, subcutaneous administration, intramuscular administration, intratumor administration, or the like.

It is preferable that the present taxane derivative-conjugated block copolymer is used as a pharmaceutical preparation that is conventionally used, such as an injectable preparation, a tablet, or a powder. In regard to formulation, pharmaceutically acceptable carriers that are conventionally used, for example, a binder, a lubricating agent, a disintegrant, a solvent, an excipient, a solubilizing agent, a dispersant, a stabilizer, a suspending agent, a preservative, a soothing agent, a colorant, and a fragrance may be used. In the case of an injectable liquid preparation, a solvent is usually used. Examples of the solvent include, but not limited to, water, physiological saline, a 5% glucose or mannitol solution; water-soluble organic solvents, such as glycerol, ethanol, dimethyl sulfoxide, N-methylpyrrolidone, polyethylene glycol, a chromophore; mixed liquids thereof; and mixed liquids of water and the water-soluble organic solvents. It is preferable that the taxane derivative-conjugated block copolymer is used after being prepared into an administrable pharmaceutical preparation using these additives for formulation.

Regarding the use of the present taxane derivative-conjugated block copolymer as an antitumor agent, the block copolymer is used for the treatment of malignant tumor diseases. The malignant tumor diseases that may be treated are not particularly limited, and the taxane derivative-conjugated block copolymer may be applied to the treatment of malignant tumor diseases such as breast cancer, non-small cell lung cancer, small cell lung cancer, colorectal cancer, non-Hodgkin's lymphoma (NHL), renal cell carcinoma, prostate cancer, hepatocarcinoma, stomach cancer, pancreatic cancer, soft tissue sarcoma, malignant skin cancer, carcinoid tumors, head and neck cancer, melanoma, ovarian cancer, cholangiocarcinoma, mesothelioma, and multiple myeloma. Particularly, the taxane derivative-conjugated block copolymer is adequate for the treatment of non-small cell lung cancer, cervical cancer, ovarian cancer, stomach cancer (inoperable or recurrent), colorectal cancer (inoperable or recurrent), breast cancer (inoperable or recurrent), squamous cell carcinoma, and malignant lymphoma (non-Hodgkin's lymphoma), for which taxane derivatives have been used for the treatment.

EXAMPLES

Hereinafter, the present invention will be further explained by way of Examples. However, the present invention is not intended to be limited to these Examples.

Measurement of the scattering intensities of the physiologically active substance-conjugated block copolymers of Examples and Comparative Examples was carried out using a dynamic light scattering photometer manufactured by Otsuka Electronics Co., Ltd., DLS-8000DL (measurement temperature: 25° C., scattering angle: 900, wavelength: 632.8 nm, ND filter: 5%, PH1: OPEN, PH2: SLIT). Regarding the measurement sample for the scattering intensity measurement, a solution obtained by adding ultrapure water to a physiologically active substance-conjugated block copolymer to obtain a concentration of 1 mg/mL, dissolving the block copolymer by irradiating the mixture with ultrasonic waves for 10 minutes under ice cooling, and then filtering the solution through a 0.2-µm membrane filter, was used.

Toluene (manufactured by Junsei Chemical Co., Ltd., special grade) that was used for the measurement of the light scattering intensity, was used after being filtered three times through a 0.2-µm membrane filter.

Measurement of the volume average particle diameters of the physiologically active substance-conjugated block copolymers of Examples and Comparative Examples was carried out using a ZetaPotential/Particlesizer NICOMP 380 ZLS (device A; temperature: 25° C.) manufactured by Particle Sizing Systems, LLC, or a particle size zeta potential analyzer, ZETASIZER NANO ZS (device B; measurement temperature: 25° C., analysis model: General Purpose (normal resolution), material RI: 1.59) manufactured by Malvern Instruments, Ltd. Regarding the volume average particle diameter measurement sample, a solution obtained by adding ultrapure water to a physiologically active substance-conjugated block copolymer to obtain a concentration of 1 mg/mL or 5 mg/mL, dissolving the block copolymer by irradiating the mixture with ultrasonic waves for 10 minutes under ice cooling, and then filtering the solution through a 0.2-µm membrane filter, was used.

[Synthesis Example 1] Synthesis of polyethylene glycol-polyglutamic Acid Block Copolymer (polyethylene glycol Molecular Weight: 2 Kilodaltons, Number of Polymerized Units of polyglutamic Acid: 8; Copolymer 1)

A polyethylene glycol having a single terminal methoxy group and a single terminal 3-aminopropyl group (SUN-BRIGHT MEPA-20H, manufactured by NOF Corporation, average molecular weight: 2 kilodaltons, 7.00 g) was dissolved in DMSO (140 mL), and then γ-benzyl L-glutamate N-carboxylic acid anhydride (7.35 g) was added thereto. The mixture was stirred for 24 hours at 30° C. The reaction liquid was added dropwise for one hour to a mixed liquid of diisopropyl ether (2,520 mL) and ethanol (280 mL), and the resulting mixture was stirred overnight at room temperature. Subsequently, a precipitate was collected by filtration and dried under reduced pressure, and thus a polymerization product (12.77 g) was obtained.

The polymerization product thus obtained was dissolved in DMF (168 mL), and acetic anhydride (2.6 mL) was added thereto. The mixture was stirred for 21 hours at 20° C. The reaction liquid was added dropwise for one hour to a mixed liquid of diisopropyl ether (1,350 mL) and ethyl acetate (150 mL), and the resulting mixture was stirred overnight at room temperature. Subsequently, a precipitate was collected by filtration and dried under reduced pressure, and thereby an acetylated polymer (11.66 g) was obtained.

The acetylated polymer thus obtained was dissolved in DMF (291 mL), and 5% palladium-carbon (1.17 g) was added thereto. Subsequently, the reaction atmosphere was purged with hydrogen, and hydrogenolysis was performed for 24 hours at room temperature and 1 atm. The 5% palladium-carbon catalyst was separated by filtration, and then the filtrate was added dropwise for one hour to a mixed liquid of heptane (1,654 mL) and ethyl acetate (827 mL). The resulting mixture was stirred overnight at room temperature. Subsequently, a precipitate was collected by filtration and was dried under reduced pressure. This precipitate was redissolved in water, and the solution was freeze-dried. Thus, a polyethylene glycol-polyglutamic acid block copolymer (Copolymer 1: 9.66 g) was obtained.

Regarding Copolymer 1, the number of polymerized units of glutamic acid was calculated to be 7.59 by a titration method using 0.1 N potassium hydroxide.

[Synthesis Example 2] Synthesis of polyethylene glycol-polyglutamic Acid Block Copolymer (polyethylene glycol Molecular Weight: 2 Kilodaltons, Number of Polymerized Units of polyglutamic Acid: 10; Copolymer 2)

A polyethylene glycol having a single terminal methoxy group and a single terminal 3-aminopropyl group (SUNBRIGHT MEPA-20H, manufactured by NOF Corporation, average molecular weight: 2 kilodaltons, 5.00 g) was dissolved in DMSO (100 mL), and then γ-benzyl L-glutamate N-carboxylic acid anhydride (7.50 g) was added thereto. The mixture was stirred for 17 hours at 30° C. The reaction liquid was added dropwise for one hour to a mixed liquid of diisopropyl ether (1,800 mL) and ethanol (200 mL), and the resulting mixture was stirred overnight at room temperature. Subsequently, a precipitate was collected by filtration and dried under reduced pressure, and thus a polymerization product (10.64 g) was obtained.

The polymerization product thus obtained was dissolved in DMF (176 mL), and acetic anhydride (2.1 mL) was added thereto. The mixture was stirred for 23 hours at 20° C. The reaction liquid was added dropwise for one hour to a mixed liquid of diisopropyl ether (1,584 mL) and ethyl acetate (176 mL), and the resulting mixture was stirred overnight at room temperature. Subsequently, a precipitate was collected by filtration and dried under reduced pressure, and thereby an acetylated polymer (9.91 g) was obtained.

The acetylated polymer thus obtained was dissolved in DMF (198 mL), and 5% palladium-carbon (0.99 g) was added thereto. Subsequently, the reaction atmosphere was purged with hydrogen, and hydrogenolysis was performed for 85 hours at room temperature and 1 atm. The 5% palladium-carbon catalyst was separated by filtration, and then the filtrate was added dropwise for one hour to a mixed liquid of heptane (1,125 mL) and ethyl acetate (563 mL). The resulting mixture was stirred overnight at room temperature. Subsequently, a precipitate was collected by filtration and was dried under reduced pressure. This precipitate was dissolved in 5% saline (570 mL), and the pH of the solution was adjusted to about 10 using a 2 N aqueous solution of sodium hydroxide. Subsequently, the mixture was purified using partition adsorption resin column chromatography followed by ion exchange resin column chromatography. The solution that had been eluted was concentrated under reduced pressure and then was freeze-dried. Thus, a polyethylene glycol-polyglutamic acid block copolymer (Copolymer 2: 5.66 g) was obtained.

Regarding Copolymer 2, the number of polymerized units of glutamic acid based on the titration value obtained using 0.1 N potassium hydroxide was 10.01.

[Synthesis Example 3] Synthesis of polyethylene glycol-polyglutamic Acid Block Copolymer (polyethylene glycol Molecular Weight: 5 Kilodaltons, Number of Polymerized Units of polyglutamic Acid: 10; Copolymer 3)

The title polyethylene glycol-polyglutamic acid block copolymer (Copolymer 3) was obtained according to the method described in Synthesis Example 2, using a polyethylene glycol having a single terminal methoxy group and a single terminal 3-aminopropyl group (SUNBRIGHT MEPA-50H, manufactured by NOF Corporation, average molecular weight: 5 kilodaltons, 10.00 g) and γ-benzyl L-glutamate N-carboxylic acid anhydride (6.02 g).

Regarding Copolymer 3, the number of polymerized units of glutamic acid based on the titration value obtained using 0.1 N potassium hydroxide was 10.02.

[Synthesis Example 4] Synthesis of polyethylene glycol-polyglutamic Acid Block Copolymer (polyethylene glycol Molecular Weight: 12 Kilodaltons, Number of Polymerized Units of polyglutamic Acid: 25; Copolymer 4)

The title polyethylene glycol-polyglutamic acid block copolymer (Copolymer 4) was obtained according to the method described in Reference Example 1 of Patent Literature 1 (WO 2004/039869 A).

Regarding Copolymer 4, the number of polymerized units of glutamic acid based on the titration value obtained using 0.1 N potassium hydroxide was 24.54.

[Synthesis Example 5] Synthesis of polyethylene glycol-polyglutamic Acid Block Copolymer (polyethylene glycol Molecular Weight: 3 Kilodaltons, Number of Polymerized Units of polyglutamic Acid: 7; Copolymer 5)

The title polyethylene glycol-polyglutamic acid block copolymer (Copolymer 5) was obtained according to the method described in Synthesis Example 1, using a polyethylene glycol having a single terminal 2-(tert-butoxycarbonylamino)ethyl group and a single terminal 2-aminoethyl group (H$_2$N-PEG-NH-Boc, manufactured by Rapp Polymere GmbH, average molecular weight: 3 kilodaltons, 5.00 g) and γ-benzyl L-glutamate N-carboxylic acid anhydride (6.02 g).

Regarding Copolymer 5, the number of polymerized units of glutamic acid based on the titration value obtained using 0.1 N potassium hydroxide was 6.55.

[Synthesis Example 6] Synthesis of polyethylene glycol-polyglutamic Acid Block Copolymer (polyethylene glycol Molecular Weight: 12 Kilodaltons, Number of Polymerized Units of polyglutamic Acid: 7; Copolymer 6)

The title polyethylene glycol-polyglutamic acid block copolymer (Copolymer 6) was obtained according to the method described in Reference Example 2 of Patent Literature 1 (WO 2004/039869 A).

Regarding Copolymer 6, the number of polymerized units of glutamic acid based on the titration value obtained using 0.1 N potassium hydroxide was 7.50.

[Example A-1] Synthesis of 7-ethyl-10-hydroxycamptothecin (EHC) Conjugate of polyethylene glycol (2 Kilodaltons)-polyglutamic Acid (7.6 Polymer) Block Copolymer Copolymer 1 (221 mg) obtained in Synthesis Example 1 and 7-ethyl-10-hydroxycamptothecin (EHC, manufactured by ScinoPharm Taiwan, Ltd., 120 mg) were dissolved in DMF (17 mL), and dimethylaminopyridine (DMAP 10 mg) and diisopropylcarbodiimide (DIPCI 174 µL) were added thereto. The mixture was stirred for 24 hours at 25° C. Subsequently, DIPCI (174 µL) was further added thereto, and the mixture was stirred for another 3 hours. The reaction liquid was added dropwise for one hour to a mixed liquid of diisopropyl ether (230 mL) and ethyl acetate (26 mL), and the resulting mixture was stirred overnight at room temperature. Subsequently, a precipitate was collected by filtration and dried under reduced pressure, and thereby a product (250 mg) was obtained. The product thus obtained was dissolved in acetonitrile/water (98/2 (v/v), 7 mL), and then an ion exchange resin was added thereto. The mixture was stirred for 7 hours at 5° C. The ion exchange resin was separated by filtration, and then acetonitrile was distilled off under reduced pressure. The residue was freeze-dried, and thereby the title camptothecin derivative-conjugated block copolymer (Example A-1) was obtained.

Example A-1 was subjected to a hydrolysis treatment using a 1 N-aqueous solution of sodium hydroxide, and EHC thus released was quantitatively determined by high performance liquid chromatography (HPLC) to thereby determine the EHC content. As a result, the EHC content in Example A-1 was 29.0% (w/w).

Example A-1 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the H-NMR spectrum, the ratio between the isopropylaminocarbonylisopropylamino group and the residue of EHC was 0.46.

From these values, the total molecular weight of Example A-1 was calculated to be 4,519.

From this, the mass content of the polyethylene glycol segment was 44.3%.

The light scattering intensity of a 1 mg/mL aqueous solution of Example A-1 was 17,070 cps, and the light scattering intensity of a standard toluene solution under the same conditions was 5,535 cps. Therefore, the relative ratio between the light scattering intensity of Example A-1 and the light scattering intensity of toluene was 3.1 times. The volume average particle diameter was 6 nm (device A, 1 mg/mL).

[Example A-2] Synthesis of 7-ethyl-10-hydroxycamptothecin (EHC) Conjugate of polyethylene glycol (2 Kilodaltons)-polyglutamic Acid (10.0 Polymer) Block Copolymer The title camptothecin derivative-conjugated block copolymer (Example A-2) was obtained according to the method described in Example A-1, using Copolymer 2 (324 mg) obtained in Synthesis Example 2 and 7-ethyl-10-hydroxycamptothecin (EHC, manufactured by ScinoPharm Taiwan, Ltd., 210 mg).

Example A-2 was subjected to a hydrolysis treatment using a 1 N-aqueous solution of sodium hydroxide, and EHC thus released was quantitatively determined by high performance liquid chromatography (HPLC) to thereby determine the EHC content. As a result, the EHC content in Example A-2 was 33.1% (w/w).

Example A-2 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of EHC was 0.47.

From these values, the total molecular weight of Example A-2 was calculated to be 5,255.

From this, the mass content of the polyethylene glycol segment was 38.1%.

The light scattering intensity of a 1 mg/mL aqueous solution of Example A-2 was 27,149 cps, and the light scattering intensity of a standard toluene solution under the same conditions was 5,535 cps. Therefore, the relative ratio between the light scattering intensity of Example A-2 and the light scattering intensity of toluene was 4.9 times. The volume average particle diameter was 10 nm (device A, 1 mg/mL).

[Example A-3] Synthesis of 7-ethyl-10-Hydroxycamptothecin (EHC) Conjugate of polyethylene glycol (5 Kilodaltons)-polyglutamic Acid (10.0 Polymer) Block Copolymer The title camptothecin derivative-conjugated block copolymer (Example A-3) was obtained according to the method described in Example A-1, using Copolymer 3 (3.00 g) obtained in Synthesis Example 3 and 7-ethyl-10-hydroxycamptothecin (EHC, manufactured by ScinoPharm Taiwan, Ltd., 1.02 g).

Example A-3 was subjected to a hydrolysis treatment using a 1 N-aqueous solution of sodium hydroxide, and EHC thus released was quantitatively determined by high performance liquid chromatography (HPLC) to thereby determine the EHC content. As a result, the EHC content in Example A-3 was 21.0% (w/w).

Example A-3 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of EHC was 0.44.

From these values, the total molecular weight of Example A-3 was calculated to be 8,225.

From this, the mass content of the polyethylene glycol segment was 60.8%.

The light scattering intensity of a 1 mg/mL aqueous solution of Example A-3 was 16,750 cps, and the light scattering intensity of a standard toluene solution under the same conditions was 5,535 cps. Therefore, the relative ratio between the light scattering intensity of Example A-3 and the light scattering intensity of toluene was 3.0 times. The volume average particle diameter was 8 nm (device A, 1 mg/mL).

[Example A-4] Synthesis of 7-ethyl-10-hydroxycamptothecin (EHC) and 2-(2-aminoethoxy)-9-(diethylamino)-5H-benzo[a]phenoxazin-5-one Conjugate of polyethylene glycol (2 Kilodaltons)-polyglutamic Acid (7.6 Polymer) Block Copolymer Copolymer 1 (981 mg) obtained in Synthesis Example 1 and 2-(2-aminoethoxy)-9-(diethylamino)-5H-benzo[a]phenoxazin-5-one (manufactured by Fuji Molecular Planning Co., Ltd., 42.2 mg) were dissolved in DMF (50 mL), and dimethylaminopyridine (DMAP 45 mg) and diisopropylcarbodiimide (DIPCI 35 µL) were added thereto. The mixture was stirred for 3 hours at 25° C. Subsequently, DIPCI (35 µL) was further added thereto, and the resulting mixture was stirred for another 1 hour. Subsequently, 7-ethyl-10-hydroxycamptothecin (EHC, manufactured by ScinoPharm Taiwan, Ltd., 532 mg) and DIPCI (771 µL) were added thereto, and the mixture was stirred for 24 hours. DIPCI (771 µL) was added thereto, and the resulting mixture was stirred for another 4 hours. Subsequently, the reaction liquid was added dropwise for one hour to a mixed liquid of diisopropyl ether (675 mL) and ethyl acetate (75 mL), and the mixture was stirred overnight at room temperature. Subsequently, a precipitate was collected by filtration and dried under reduced pressure, and thus a product was obtained. The product thus obtained was dissolved in acetonitrile/water (98/2 (v/v), 30 mL), and then an ion exchange resin was added thereto. The mixture was stirred for 7 hours at 5° C. The ion exchange resin was separated by filtration, and then acetonitrile was distilled off under reduced pressure and freeze-dried. Thereby, the title camptothecin derivative-conjugated block copolymer (Example A-4) was obtained.

Example A-4 was subjected to a hydrolysis treatment using a 1 N-aqueous solution of sodium hydroxide, and EHC thus released was quantitatively determined by high performance liquid chromatography (HPLC) to thereby determine the EHC content. As a result, the EHC content in Example A-4 was 24.2% (w/w).

The 2-(2-aminoethoxy)-9-(diethylamino)-5H-benzo[a]phenoxazin-5-one conjugation amount of Example A-4 was one molecule, as calculated from the consumption ratio of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one of Example A-4 was calculated to be 377.

From these values, the total molecular weight of Example A-4 was calculated to be 4,617.

From this, the content of 2-(2-aminoethoxy)-9-(diethylamino)-5H-benzo[a]phenoxazin-5-one in Example A-4 was 8.2% by mass, and the content of the polyethylene glycol segment was 43.3% by mass.

Example A-4 was used in the distribution test that will be described below, as a fluorescent labeled body of Example A-1.

[Comparative Example A-1] Synthesis of 7-ethyl-10-hydroxycamptothecin (EHC) Conjugate of polyethylene glycol (12 Kilodaltons)-polyglutamic Acid (25 Polymer) Block Copolymer The title camptothecin derivative-conjugated block copolymer (Comparative Example A-1) was obtained according to the method described in Example 1 of Patent Literature 1 (WO 2004/039869 A), using Copolymer 4 obtained in Synthesis Example 4.

Comparative Example A-1 was subjected to a hydrolysis treatment using a 1 N-aqueous solution of sodium hydroxide, and EHC thus released was quantitatively determined by high performance liquid chromatography (HPLC) to thereby determine the EHC content. As a result, the EHC content in Comparative Example A-1 was 22.5% (w/w).

Comparative Example A-1 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of EHC was 0.26.

From these values, the total molecular weight of Comparative Example A-1 was calculated to be 19,245.

From this, the mass content of the polyethylene glycol segment was 62.4%.

The light scattering intensity of a 1 mg/mL aqueous solution of Comparative Example A-1 was 41,321 cps, and the light scattering intensity of a standard toluene solution under the same conditions was 5,535 cps. Therefore, the relative ratio between the light scattering intensity of Comparative Example A-1 and the light scattering intensity of toluene was 7.5 times. The volume average particle diameter was 20 nm (device A, 1 mg/mL).

[Comparative Example A-2] Synthesis of 7-ethyl-10-hydroxycamptothecin (EHC) Conjugate of polyethylene glycol (3 Kilodaltons)-polyglutamic Acid (6.6 Polymer) Block Copolymer The title camptothecin derivative-conjugated block copolymer (Comparative Example A-2) was obtained according to the method described in Example A-1, using Copolymer 5 obtained in Synthesis Example 5 and 7-ethyl-10-hydroxycamptothecin (EHC, manufactured by ScinoPharm Taiwan, Ltd., 91 mg).

Comparative Example A-2 was subjected to a hydrolysis treatment using a 1 N-aqueous solution of sodium hydroxide, and EHC thus released was quantitatively determined by high performance liquid chromatography (HPLC) to thereby determine the EHC content. As a result, the EHC content in Comparative Example 2 was 20.1% (w/w).

Comparative Example A-2 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of EHC was 0.37.

From these values, the total molecular weight of Comparative Example A-2 was calculated to be 5,031.

From this, the mass content of the polyethylene glycol segment was 59.6%.

The light scattering intensity of a 1 mg/mL aqueous solution of Comparative Example A-2 was 9,964 cps, and the light scattering intensity of a standard toluene solution under the same conditions was 5,535 cps. Therefore, the relative ratio between the light scattering intensity of Comparative Example A-2 and the light scattering intensity of toluene was 1.80 times. The camptothecin derivative-conjugated block copolymer of Comparative Example A-2 was non-associating.

[Comparative Example A-3] Synthesis of 7-ethyl-10-hydroxycamptothecin (EHC) Conjugate of polyethylene glycol (12 Kilodaltons)-polyglutamic Acid (7.5 Polymer) Block Copolymer The title camptothecin derivative-conjugated block copolymer (Comparative Example A-3) was obtained according to the method described in Patent Literature 1, using Copolymer 6 obtained in Synthesis Example 6.

Comparative Example A-3 was subjected to a hydrolysis treatment using a 1 N-aqueous solution of sodium hydroxide, and EHC thus released was quantitatively determined by high performance liquid chromatography (HPLC) to thereby determine the EHC content. As a result, the EHC content in Comparative Example A-3 was 7.8% (w/w).

Comparative Example A-3 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of EHC was 0.28.

From these values, the total molecular weight of Comparative Example A-3 was calculated to be 14,094.

From this, the mass content of the polyethylene glycol segment was 85.1%.

The light scattering intensity of a 1 mg/mL aqueous solution of Comparative Example A-3 was 5,625 cps, and the light scattering intensity of a standard toluene solution under the same conditions was 5,535 cps. Therefore, the relative ratio between the light scattering intensity of Comparative Example A-3 and the light scattering intensity of toluene was 1.0 time. The camptothecin derivative-conjugated block copolymer of Comparative Example A-3 was non-associating.

[Comparative Example A-4] Synthesis of 7-ethyl-10-hydroxycamptothecin (EHC) and 2-(2-aminoethoxy)-9-(diethylamino)-5H-benzo[a]phenoxazin-5-one Conjugate of polyethylene glycol (12 Kilodaltons)-polyglutamic Acid (25 Polymer) Block Copolymer Copolymer 4 (6 g) obtained in Synthesis Example 4 and 2-(2-aminoethoxy)-9-(diethylamino)-5H-benzo[a]phenoxazin-5-one (manufactured by Fuji Molecular Planning Co., Ltd., 162.3 mg) were dissolved in DMF (160 mL), and 4-(4,6-dimethoxy-1,3,5-triazin-2-yl)-4-methylmorpholium chloride n-hydrate (DMT-MM, 145 mg) was added thereto. The mixture was stirred for 29 hours at 25° C., and the reaction liquid was added dropwise for 20 minutes to a mixed liquid of diisopropyl ether (1460 mL) and ethanol (360 mL). The resulting mixture was stirred for 40 minutes at room temperature, and then a precipitate was collected by filtration and dried under reduced pressure. Thus, a product was obtained. The product thus obtained and 7-ethyl-10-hydroxycamptothecin (EHC, manufactured by ScinoPharm Taiwan, Ltd., 1778 mg) were dissolved in DMF (250 mL), and dimethylaminopyridine (DMAP 151 mg) and diisopropylcarbodiimide (DIPCI 2583 µL) were added thereto. The mixture was stirred for 22 hours at 25° C. Subsequently, DIPCI (646 µL) was further added thereto, and the resulting mixture was stirred for 2 hours. The reaction liquid was added dropwise for 30 minutes to a mixed liquid of diisopropyl ether (3,000 mL) and ethanol (1,000 mL), and the mixture was stirred for one hour at room temperature. A precipitate was collected by filtration and dried under reduced pressure, and thus a product (7.3 g) was obtained. The product thus obtained was dissolved in acetonitrile/water (98/2 (v/v), 7 mL), and then an ion exchange resin was added thereto. The mixture was stirred for 3 hours at 5° C. The ion exchange resin was separated by filtration, and then acetonitrile was distilled off under reduced pressure. The residue was freeze-dried, and thus, the title camptothecin derivative-conjugated block copolymer (Comparative Example A-4) was obtained.

Comparative Example A-4 was subjected to a hydrolysis treatment using a 1 N-aqueous solution of sodium hydroxide, and EHC thus released was quantitatively determined by high performance liquid chromatography (HPLC) to thereby determine the EHC content. As a result, the EHC content in Comparative Example A-4 was 19.1% (w/w).

The 2-(2-aminoethoxy)-9-(diethylamino)-5H-benzo[a]phenoxazin-5-one conjugation amount of Comparative Example A-4 was one molecule, as calculated from the consumption ratio of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Comparative Example A-4 was calculated to be 377.

From these values, the total molecular weight of Comparative Example A-4 was calculated to be 19,007.

From this, the content of 2-(2-aminoethoxy)-9-(diethylamino)-5H-benzo[a]phenoxazin-5-one in Comparative Example A-4 was 1.9% by mass, and the content of the polyethylene glycol segment was 63.1% by mass.

Comparative Example A-4 was used in the distribution test that will be described below, as a fluorescent labeled body of Comparative Example A-1.

[Test Example A-1] Intratumor Distribution Test

A tumor mass of human pancreatic cancer BxPC3 that had been subcultured by subcutaneous transplantation in a BALB/c nude mouse was cut into a block having a size of about 3 mm on each side, and this block was subcutaneously transplanted on the dorsal side of a nude mouse using a trocar. Example A-4 and Comparative Example A-4 were respectively dissolved in a 5% glucose injection solution, and the solutions were respectively intravenously administered once at a dose of 50 mg/kg as converted to 7-ethyl-10-hydroxycamptothecin. Thirty minutes after the administration, blood was removed from the mouse under isoflurane anesthesia, frozen embedded slices of the removed tumor were produced, and fluorescence was observed. The results are presented in Table 1.

As a result of Test Example A-1, fluorescent signals were observed in a wide area of the tumor slices in Example A-4. From this, it was found that the block copolymer of Example A-4 could penetrate into deep parts of a tumor tissue. In contrast, it was found in the case of Comparative Example A-4 that the tendency was maldistributed only at the fringe area of the tumor, and the block copolymer did not penetrate into deep parts of the tumor tissue. Therefore, it was suggested that Example A-4 is capable of penetrating into the whole area of a tumor tissue and causing the camptothecin derivative, which is the conjugated drug, to act on the entire tumor tissue.

[Test Example A-2] Intrarenal Distribution Test

Example A-4 and Comparative Example A-4 were respectively dissolved in a 5% glucose injection solution, and the solutions were respectively intravenously administered once to a C.B-17SCID mouse at a dose of 50 mg/kg as converted to 7-ethyl-10-hydroxycamptothecin. Thirty minutes after the administration, blood was removed from the mouse under isoflurane anesthesia, frozen embedded slices of the removed tumor were produced, and fluorescence was observed. The results are presented in FIG. 2.

As a result of Test Example A-2, fluorescent signals were observed in the blood vessels and the renal tubules of the kidneys in Example A-4. Therefore, it was found that the block copolymer of Example A-4 has a property of being excretable through the kidneys while being a macromolecule. On the other hand, it was found in the case of Comparative Example A-4 that fluorescence was not recognized in areas other than the blood vessels of the kidneys, and Comparative Example A-4 was not excretable through the kidneys.

[Test Example A-3] Hepatotoxicity Test in Non-Tumor Bearing Mouse

[Drug Administration]

Example A-1, Example A-2, Comparative Example A-2, and Comparative Example A-3 were respectively dissolved in a 5% glucose injection solution, and the solutions were respectively intravenously administered once to 6-week old male Crl:CD1(ICR)(ICR(IGS)) mice through the caudal vein at a dose of 50 mg/kg or 100 mg/kg as converted to 7-ethyl-10-hydroxycamptothecin, which were the maximum tolerated doses for the various compounds, based on the body weight measured on the day of administration. As a control group, a 5% glucose injection solution was intravenously administered once through the caudal vein.

[Blood Chemical Examination]

Three days after the administration of the various compounds, blood was collected through the abdominal aorta under isoflurane anesthesia using a 1-mL disposable syringe with a 27 G needle. About 10 μL of a heparin sodium solution had been added to the syringe in advance, and this solution was sufficiently mixed with the blood thus collected. The blood plasma obtained by centrifuging the blood thus collected (4° C., 1600×g, 10 minutes) was used as a measurement sample, and a blood chemical examination of the measurement sample was performed using an automatic biochemical analysis apparatus Model 7180 (Hitachi High Technologies Corp.). The results of measuring the ALT (alanine aminotransferase) in the blood plasma are presented in Table 1.

In the blood chemical examination, a noticeable increase in the ALT was recognized in Comparative Example A-2, and occurrence of hepatotoxicity was acknowledged. In Comparative Example A-3, despite the low dose, the ALT increased, and hepatotoxicity was clearly manifested. In contrast, a significant increase in the ALT was not recognized with the compounds of Examples A-1 and A-2, and it was found that hepatotoxicity was negligible.

The compounds of Comparative Example A-2 and Comparative Example A-3 are both non-associating compounds, whose light scattering intensities in an aqueous solution are twice or less the light scattering intensity of toluene. From the above results, it was found with regard to camptothecin derivative-conjugated block copolymers that the analysis values represented by the light scattering intensity in an aqueous solution correlate with the expression of hepatotoxicity. Thus, a camptothecin derivative-conjugated block copolymer having low expression of hepatotoxicity may be produced by using toluene as a standard substance for the measurement of laser light scattering intensity, and measuring the light scattering intensity of the aqueous solution as a relative intensity with respect to toluene.

[Test Example A-4] Hematotoxicity Test in Non-Tumor Bearing Rat

[Drug Administration]

The compounds of Example A-1, Example A-3, Comparative Example A-1, and Comparative Example A-2 were respectively dissolved in a 5% glucose injection solution, and the solutions were respectively intravenously administered once to 7-week old male Sprague-Dawley rats (Crl: CD; IGS, Charles River Laboratories Japan, Inc.) through the caudal vein at a dose of 40 mg/kg as converted to 7-ethyl-10-hydroxycamptothecin based on the body weight measured on the day of administration. As a control group, a 5' glucose injection solution was intravenously administered once through the caudal vein.

[Hematological Examination]

After 3, 5, 7, 11, and 14 days from the day of administration of the various compounds, blood was collected through the subclavian vein without anesthesia using a 1-mL disposable syringe with a 26 G needle. About 3 μL of an EDTA-2K solution had been added in advance to the syringe, and this solution was sufficiently mixed with the blood thus collected. The resultant solutions were used as analysis samples. The blood samples were subjected to a blood cell analysis using a blood cell analysis apparatus XT-2000iV (Sysmex Corp.). The numbers of blood reticulocytes obtained 7 days after the administration are presented in Table 2.

TABLE 1

Results of blood chemical examination (ALT)

| Drug | Dose | ALT |
|---|---|---|
| 5% glucose injection solution | — | 24 ± 5(22 ± 6) |
| Example A-1 | 100 | 64 ± 25 |
| Example A-2 | 100 | 55 ± 54 |
| Comparative Example A-2 | 100 | 528 ± 681 |
| Comparative Example A-3 | 50 | 114 ± 68 |

TABLE 2

Results of hematological examination (blood reticulocytes)

| Drug | Number of blood reticulocytes* |
|---|---|
| 5% glucose injection solution | 50.04 ± 7.09 |
| Example A-1 | 64.18 ± 4.43 |
| Example A-3 | 54.29 ± 8.49 |

TABLE 2-continued

Results of hematological examination (blood reticulocytes)

| Drug | Number of blood reticulocytes* |
|---|---|
| Comparative Example A-1 | 20.26 ± 11.50 |
| Comparative Example A-2 | 66.17 ± 7.74 |

**Number of blood reticulocytes ($\times 10^4/\mu L$) in various treated groups on the $7^{th}$ day after administration As a result of the hematological examination, Comparative Example A-1 caused a decrease in the number of blood reticulocytes after 7 days from the day of administration, and prolonged hematotoxicity was recognized. In contrast, the compounds of present Examples A-1 and A-3 did not cause a decrease in the number of blood reticulocytes at the time point of 7 days after the administration, and prolonged hematotoxicity was not recognized. Therefore, it is speculated that the compounds of Examples A-1 and A-3 did not protract hematotoxicity.

Comparative Example A-1 is a compound having a molecular weight of 19 kilodaltons. On the other hand, Examples A-1 and A-3 and Comparative Example A-2 have small molecular weights. From the above results, it is considered that persistence hematotoxicity of a camptothecin derivative-conjugated block copolymer correlates with the molecular weight. Therefore, by employing a camptothecin derivative-conjugated block copolymer having a molecular weight of 15 kilodaltons or less, an antitumor agent that avoids persistence of hematotoxicity may be produced.

[Test Example A-5] Test on Antitumor Effect in Human Stomach Cancer-Transplanted Nude Mouse A tumor mass of human stomach cancer SC-4-JCK that had been subcutaneously subcultured in a nude mouse was cut into a block having a size of about 3 mm on each side, and this block was subcutaneously transplanted on the dorsal side of a nude mouse using a trocar. At the time point when the average tumor volume reached about 150 mm³ or more after the tumor transplantation, Example A-1, Example A-2, Example A-3, Comparative Example A-1, and Comparative Example A-2 were respectively dissolved in a 5% glucose injection solution, and the solutions were respectively intravenously administered once at a dose of 12 mg/kg as converted to 7-ethyl-10-hydroxycamptothecin.

A relative tumor volume was determined from the tumor volumes obtained on the day of administration and on the $14^{th}$ day after the administration, and this was employed as an index for the antitumor effect. The tumor volume was determined by measuring the major axis (L: mm) and the minor axis (W: mm) of the tumor, and calculating the volume by the calculation formula: $(L \times W^2)/2$. The results are presented in Table 3.

TABLE 3

Results of antitumor effect test

| Drug | Relative tumor volume* |
|---|---|
| Not administered | 3.260 ± 0.620 |
| Example A-1 | 2.466 ± 0.398 |
| Example A-2 | 2.593 ± 0.482 |
| Example A-3 | 1.574 ± 0.388 |
| Comparative Example A-1 | 2.232 ± 0.534 |
| Comparative Example A-2 | 2.426 ± 1.122 |

*Relative tumor volume (average ± SD) in various treated groups on the $14^{th}$ day after administration in a case in which the tumor volume on the day of drug administration is designated as 1.0

Examples A-1 to A-3 and Comparative Examples A-1 and A-2 resulted in small tumor volumes compared to the non-drug administered group, and exhibited tumor proliferation suppressing action. Among them, Example A-3 exhibited a stronger antitumor effect compared to the Comparative Examples.

It is known that camptothecin derivative-conjugated block copolymers are capable of enhancing an antitumor effect by means of unique pharmacokinetics attributed to the polymer carrier and controlled release of the camptothecin derivative. However, since the camptothecin derivative-conjugated block copolymers cause occurrence of the pharmacological action of the camptothecin derivative not only in tumor tissues but also in normal tissues, manifestation of adverse effects has been unavoidable.

However, from the results of Test Examples A-1 to A-4, it is obvious that the present camptothecin derivative-conjugated block copolymers exhibit an antitumor effect that is equivalent or superior to that of conventional camptothecin derivative-conjugated block copolymers, and also suppress the manifestation of hepatotoxicity, without protracting hematotoxicity. Therefore, it became clear that when a camptothecin derivative-conjugated block copolymer having a controlled molecular weight and a controlled light scattering intensity in an aqueous solution is employed, an antitumor agent that is capable of avoiding the normal tissue injuring action from the tumor proliferation suppressing action, and of achieving efficacy enhancement and reduction of adverse effects, may be provided.

[Synthesis Example 7] Synthesis of polyethylene glycol-polyglutamic Acid Block Copolymer (polyethylene glycol Molecular Weight: 2 Kilodaltons, Number of Polymerized Units of polyglutamic Acid: 8; Copolymer 7)

The title polyethylene glycol-polyglutamic acid block copolymer (Copolymer 7) was obtained according to the method described in Synthesis Example 2, using a polyethylene glycol having a single terminal methoxy group and a single terminal 3-aminopropyl group (SUNBRIGHT MEPA-50H, manufactured by NOF Corp., average molecular weight: 5 kilodaltons, 14.00 g) and γ-benzyl L-glutamate N-carboxylic acid anhydride (16.80 g).

Regarding Copolymer 7, the number of polymerized units of glutamic acid based on the titration value obtained using 0.1 N potassium hydroxide was 7.90.

[Synthesis Example 8] Synthesis of polyethylene glycol-polyglutamic Acid Block Copolymer (polyethylene glycol Molecular Weight: 2 Kilodaltons, Number of Polymerized Units of polyglutamic Acid: 6; Copolymer 8)

The title polyethylene glycol-polyglutamic acid block copolymer (Copolymer 8) was obtained according to the method described in Synthesis Example 2, using a polyethylene glycol having a single terminal methoxy group and a single terminal 3-aminopropyl group (SUNBRIGHT MEPA-50H, manufactured by NOF Corp., average molecular weight: 5 kilodaltons, 14.00 g) and γ-benzyl L-glutamate N-carboxylic acid anhydride (12.60 g).

Regarding Copolymer 8, the number of polymerized units of glutamic acid based on the titration value obtained using 0.1 N potassium hydroxide was 6.46.

[Synthesis Example 9] Synthesis of polyethylene glycol-polyglutamic Acid Block Copolymer (polyethylene glycol Molecular Weight: 2 Kilodaltons, Number of Polymerized Units of polyglutamic Acid: 14; Copolymer 9)

The title polyethylene glycol-polyglutamic acid block copolymer (Copolymer 9) was obtained according to the method described in Synthesis Example 2, using a polyethylene glycol having a single terminal methoxy group and a single terminal 3-aminopropyl group (SUNBRIGHT MEPA-50H, manufactured by NOF Corp., average molecular weight: 2 kilodaltons, 10.15 g) and γ-benzyl L-glutamate N-carboxylic acid anhydride (18.28 g).

Regarding Copolymer 9, the number of polymerized units of glutamic acid based on the titration value obtained using 0.1 N potassium hydroxide was 13.69.

[Example B-1] Synthesis of 4-isopropyl-6-(4-(1-methyl-1H-indol-5-yl)-5-methylene-4,5-dihydro-1H-1,2,4-triazol-3-yl)benzene-1,3-diol Conjugate of polyethylene glycol (2 Kilodaltons)-polyglutamic Acid (7.9 Polymer) Block Copolymer Copolymer 7 (1,300 mg) obtained in Synthesis Example 7 and 4-isopropyl-6-(4-(1-methyl-1H-indol-5-yl)-5-methylene-4,5-dihydro-1H-1,2,4-triazol-3-yl)benzene-1,3-diol (manufactured by Shanghai Haoyuan Chemexpress Co., Ltd., 550 mg) were dissolved in DMF (46 mL), and dimethylaminopyridine (DMAP 64 mg) and diisopropylcarbodiimide (DIPCI 1050 μL) were added thereto. The mixture was stirred for 24 hours at 25° C. Subsequently, DIPCI (525 μL) was further added thereto, and the resulting mixture was stirred for another 2 hours. The reaction liquid was added dropwise for 15 minutes to a mixed liquid of diisopropyl ether (250 mL) and ethyl acetate (500 mL), and the mixture was stirred for 45 minutes at room temperature. A precipitate was collected by filtration and dried under reduced pressure, and thus a product (1,558 mg) was obtained. The product thus obtained was dissolved in acetonitrile/water (1/1 (v/v), 100 mL), and then an ion exchange resin was added thereto. The mixture was stirred for 3 hours at 5° C. The ion exchange resin was separated by filtration, and then acetonitrile was distilled off under reduced pressure. The residue was freeze-dried, and thus, the title 4-isopropyl-6-(4-(1-methyl-1H-indol-5-yl)-5-methylene-4,5-dihydro-1H-1,2,4-triazol-3-yl)benzene-1,3-diol-conjugated block copolymer (Example B-1) was obtained.

Example B-1 was subjected to a hydrolysis treatment using a 1 N-aqueous solution of sodium hydroxide, and 4-isopropyl-6-(4-(1-methyl-1H-indol-5-yl)-5-methylene-4,5-dihydro-1H-1,2,4-triazol-3-yl)benzene-1,3-diol thus released was quantitatively determined by high performance liquid chromatography (HPLC) to thereby determine the content thereof. As a result, the content of 4-isopropyl-6-(4-(1-methyl-1H-indol-5-yl)-5-methylene-4,5-dihydro-1H-1,2,4-triazol-3-yl)benzene-1,3-diol in Example B-1 was 21.8% (w/w).

Example B-1 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the 1H-NMR spectrum, the ratio between the isopropylaminocarbonylisopropylamino group and the residue of 4-isopropyl-6-(4-(1-methyl-1H-indol-5-yl)-5-methylene-4,5-dihydro-1H-1,2,4-triazol-3-yl)benzene-1,3-diol was 0.27.

From these values, the total molecular weight of Example B-1 was calculated to be 3,963.

From this, the mass content of the polyethylene glycol segment was 50.5.

The light scattering intensity of a 1 mg/mL aqueous solution of Example B-1 was 83,228 cps, and the light scattering intensity of a standard toluene solution under the same conditions was 7,195 cps. Therefore, the relative ratio between the light scattering intensity of Example B-1 and the light scattering intensity of toluene was 11.6 times. The volume average particle diameter was 11 nm (device A, 5 mg/mL).

[Example B-2] Synthesis of 4-isopropyl-6-(4-(1-methyl-1H-indol-5-yl)-5-methylene-4,5-dihydro-1H-1,2,4-triazol-3-yl)benzene-1,3-diol and BODIPY-FL Conjugate of polyethylene glycol (2 Kilodaltons)-polyglutamic Acid (7.9 Polymer) Block Copolymer Copolymer 7 (40 mg) obtained in Synthesis Example 7, 4-isopropyl-6-(4-(1-methyl-1H-indol-5-yl)-5-methylene-4,5-dihydro-1H-1,2,4-triazol-3-yl)benzene-1,3-diol (manufactured by Shanghai Haoyuan Chemexpress Co., Ltd., 17 mg), BODIPY-FL EDA.HCl (manufactured by Life Technologies Corp., 5 mg), and diisopropylethylamine (4 μL) were dissolved in DMF (1 mL), and dimethylaminopyridine (DMAP 2 mg) and diisopropylcarbodiimide (DIPCI 33 μL) were added thereto. The mixture was stirred for 24 hours at 25° C. Subsequently, DIPCI (16 μL) was further added thereto, and the resulting mixture was stirred for another 3 hours. The reaction liquid was added dropwise for 20 minutes to a mixed liquid of diisopropyl ether (7 mL) and ethyl acetate (14 mL), and the mixture was stirred for 20 minutes at room temperature. Subsequently, a precipitate was collected by filtration and was dried under reduced pressure. Thus, a product was obtained. The product thus obtained was dissolved in acetonitrile/water (1/1 (v/v), 10 mL), and then an ion exchange resin was added thereto. The mixture was stirred for 45 minutes at 5° C. The ion exchange resin was separated by filtration, and then acetonitrile was distilled off under reduced pressure. The residue was freeze-dried, and thus, the title 4-isopropyl-6-(4-(1-methyl-1H-indol-5-yl)-5-methylene-4,5-dihydro-1H-1,2,4-triazol-3-yl)benzene-1,3-diol-conjugated block copolymer (Example B-2) was obtained.

Example B-2 was subjected to a hydrolysis treatment using a 1 N-aqueous solution of sodium hydroxide, and the content of 4-isopropyl-6-(4-(1-methyl-1H-indol-5-yl)-5-methylene-4,5-dihydro-1H-1,2,4-triazol-3-yl)benzene-1,3-diol thus released was determined. As a result, the content of 4-isopropyl-6-(4-(1-methyl-1H-indol-5-yl)-5-methylene-4,5-dihydro-1H-1,2,4-triazol-3-yl)benzene-1,3-diol in Example B-2 was quantitatively determined by high performance liquid chromatography (HPLC), and the content thereof was 23.1% (w/w).

Example B-2 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the 1H-NMR spectrum, the ratio between the isopropylaminocarbonylisopropylamino group and the residue of 4-isopropyl-6-(4-(1-methyl-1H-indol-5-yl)-5-methylene-4,5-dihydro-1H-1,2,4-triazol-3-yl)benzene-1,3-diol was 0.27.

The BODIPY-FL conjugation amount of Example B-2 was 1.0 molecule, as calculated from the consumption ratio of BODIPY-FL in the reaction solution measured by high performance liquid chromatography (HPLC). Therefore, the total molecular weight of BODIPY-FL in Example B-2 was calculated to be 334.

From these values, the total molecular weight of Example B-2 was calculated to be 4,451.

From this, the content of BODIPY-FL in Example-2 was 7.5% by mass, and the content of the polyethylene glycol segment was 44.9% by mass.

Example B-2 was used in the distribution test that will be described below, as a fluorescent labeled body of Example B-1.

[Example B-3] Synthesis of 4-isopropyl-6-(4-(1-methyl-1H-indol-5-yl)-5-methylene-4,5-dihydro-1H-1,2,4-triazol-3-yl)benzene-1,3-diol Conjugate of polyethylene glycol (2 Kilodaltons)-polyglutamic Acid (6 Polymer) Block Copolymer The title resorcinol compound-conjugated block copolymer (Example B-3) was obtained according to the method described in Example B-1, using Copolymer 8 (1,100 mg) obtained in Synthesis Example 8 and 4-isopropyl-6-(4-(1-methyl-1H-indol-5-yl)-5-methylene-4,5-dihydro-1H-1,2,4-triazol-3-yl)benzene-1,3-diol (manufactured by Shanghai Haoyuan Chemexpress Co., Ltd., 450 mg).

Example B-3 was subjected to a hydrolysis treatment using a 1 N-aqueous solution of sodium hydroxide, and 4-isopropyl-6-(4-(1-methyl-1H-indol-5-yl)-5-methylene-4,5-dihydro-1H-1,2,4-triazol-3-yl)benzene-1,3-diol thus released was quantitatively determined by high performance liquid chromatography (HPLC) to thereby determine the content thereof. As a result, the content of 4-isopropyl-6-(4-(1-methyl-1H-indol-5-yl)-5-methylene-4,5-dihydro-1H-1,2,4-triazol-3-yl)benzene-1,3-diol in Example B-3 was 18.8% (w/w).

Example B-3 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of 4-isopropyl-6-(4-(1-methyl-1H-indol-5-yl)-5-methylene-4,5-dihydro-1H-1,2,4-triazol-3-yl)benzene-1,3-diol was 0.11.

From these values, the total molecular weight of Example B-3 was calculated to be 3,539.

From this, the mass content of the polyethylene glycol segment was 56.5'.

The light scattering intensity of a 1 mg/mL aqueous solution of Example B-3 was 37,270 cps, and the light scattering intensity of a standard toluene solution under the same conditions was 7,195 cps. Therefore, the relative ratio between the light scattering intensity of Example B-3 and the light scattering intensity of toluene was 5.0 times. The volume average particle diameter was 8 nm (device A, 5 mg/mL).

[Example B-4] Synthesis of 4-isopropyl-6-(4-(1-methyl-1H-indol-5-yl)-5-methylene-4,5-dihydro-1H-1,2,4-triazol-3-yl)benzene-1,3-diol Conjugate of polyethylene glycol (2 Kilodaltons)-polyglutamic Acid (10 Polymer) Block Copolymer The title resorcinol compound-conjugated block copolymer (Example B-4) was obtained according to the method described in Example B-1, using Copolymer 2 (966 mg) obtained in Synthesis Example 2 and 4-isopropyl-6-(4-(1-methyl-1H-indol-5-yl)-5-methylene-4,5-dihydro-1H-1,2,4-triazol-3-yl)benzene-1,3-diol (manufactured by Shanghai Haoyuan Chemexpress Co., Ltd., 317 mg).

Example B-4 was subjected to a hydrolysis treatment using a 1 N-aqueous solution of sodium hydroxide, and 4-isopropyl-6-(4-(1-methyl-1H-indol-5-yl)-5-methylene-4,5-dihydro-1H-1,2,4-triazol-3-yl)benzene-1,3-diol thus released was quantitatively determined by high performance liquid chromatography (HPLC) to thereby determine the content thereof. As a result, the content of 4-isopropyl-6-(4-(1-methyl-1H-indol-5-yl)-5-methylene-4,5-dihydro-1H-1,2,4-triazol-3-yl)benzene-1,3-diol in Example B-4 was 17.0% (w/w).

Example B-4 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of 4-isopropyl-6-(4-(1-methyl-1H-indol-5-yl)-5-methylene-4,5-dihydro-1H-1,2,4-triazol-3-yl)benzene-1,3-diol was 0.09.

From these values, the total molecular weight of Example B-3 was calculated to be 4,001.

From this, the mass content of the polyethylene glycol segment was 50.0%.

The light scattering intensity of a 1 mg/mL aqueous solution of Example B-3 was 125,125 cps, and the light scattering intensity of a standard toluene solution under the same conditions was 7,195 cps. Therefore, the relative ratio between the light scattering intensity of Example B-3 and the light scattering intensity of toluene was 16.9 times. The volume average particle diameter was 11 nm (device A, 5 mg/mL).

[Example B-5] Synthesis of 4-isopropyl-6-(4-(1-methyl-1H-indol-5-yl)-5-methylene-4,5-dihydro-1H-1,2,4-triazol-3-yl)benzene-1,3-diol Conjugate of polyethylene glycol (2 Kilodaltons)-polyglutamic Acid (12 Polymer) Block Copolymer The title resorcinol compound-conjugated block copolymer (Example B-5) was obtained according to the method described in Example B-1, using Copolymer 9 (1,500 mg) obtained in Synthesis Example 9 and 4-isopropyl-6-(4-(1-methyl-1H-indol-5-yl)-5-methylene-4,5-dihydro-1H-1,2,4-triazol-3-yl)benzene-1,3-diol (manufactured by Shanghai Haoyuan Chemexpress Co., Ltd., 393 mg).

Example B-5 was subjected to a hydrolysis treatment using a 1 N-aqueous solution of sodium hydroxide, and 4-isopropyl-6-(4-(1-methyl-1H-indol-5-yl)-5-methylene-4,5-dihydro-1H-1,2,4-triazol-3-yl)benzene-1,3-diol thus released was quantitatively determined by high performance liquid chromatography (HPLC) to thereby determine the content thereof. As a result, the content of 4-isopropyl-6-(4-(1-methyl-1H-indol-5-yl)-5-methylene-4,5-dihydro-1H-1,2,4-triazol-3-yl)benzene-1,3-diol in Example B-5 was 12.7% (w/w).

Example B-5 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of 4-isopropyl-6-(4-(1-methyl-1H-indol-5-yl)-5-methylene-4,5-dihydro-1H-1,2,4-triazol-3-yl)benzene-1,3-diol was 0.34.

From these values, the total molecular weight of Example B-5 was calculated to be 4,409.

From this, the mass content of the polyethylene glycol segment was 45.4%.

The light scattering intensity of a 1 mg/mL aqueous solution of Example B-5 was 50,425 cps, and the light scattering intensity of a standard toluene solution under the same conditions was 7,195 cps. Therefore, the relative ratio between the light scattering intensity of Example B-5 and the light scattering intensity of toluene was 6.8 times. The volume average particle diameter was 14 nm (device B, 5 mg/mL).

[Example B-6] Synthesis of 4-isopropyl-6-(4-(1-methyl-1H-indol-5-yl)-5-methylene-4,5-dihydro-1H-1,2,4-triazol-3-yl)benzene-1,3-diol Conjugate of polyethylene glycol (5 Kilodaltons)-polyglutamic Acid (10 Polymer) Block Copolymer The title resorcinol compound-conjugated block copolymer (Example B-6) was obtained according to the method described in Example B-1, using Copolymer 3 (953 mg) obtained in Synthesis Example 3 and 4-isopropyl-6-(4-(1-methyl-1H-indol-5-yl)-5-methylene-4,5-dihydro-1H-1,2,4-triazol-3-yl)benzene-1,3-diol (manufactured by Shanghai Haoyuan Chemexpress Co., Ltd., 250 mg).

Example B-6 was subjected to a hydrolysis treatment using a 1 N-aqueous solution of sodium hydroxide, and 4-isopropyl-6-(4-(1-methyl-1H-indol-5-yl)-5-methylene-4,5-dihydro-1H-1,2,4-triazol-3-yl)benzene-1,3-diol thus released was quantitatively determined by high performance liquid chromatography (HPLC) to thereby determine the content thereof. As a result, the content of 4-isopropyl-6-(4-(1-methyl-1H-indol-5-yl)-5-methylene-4,5-dihydro-1H-1,2,4-triazol-3-yl)benzene-1,3-diol in Example B-6 was 17.3% (w/w).

Example B-6 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of 4-isopropyl-6-(4-(1-methyl-1H-indol-5-yl)-5-methylene-4,5-dihydro-1H-1,2,4-triazol-3-yl)benzene-1,3-diol was 0.23.

From these values, the total molecular weight of Example B-6 was calculated to be 7,724.

From this, the mass content of the polyethylene glycol segment was 64.7%.

The light scattering intensity of a 1 mg/mL aqueous solution of Example B-6 was 88,115 cps, and the light scattering intensity of a standard toluene solution under the same conditions was 7,195 cps. Therefore, the relative ratio between the light scattering intensity of Example B-5 and the light scattering intensity of toluene was 11.9 times. The volume average particle diameter was 12 nm (device A, 5 mg/mL).

[Comparative Example B-1] Synthesis of 4-isopropyl-6-(4-(1-methyl-1H-indol-5-yl)-5-methylene-4,5-dihydro-1H-1,2,4-triazol-3-yl)benzene-1,3-diol Conjugate of polyethylene glycol (12 Kilodaltons)-polyglutamic Acid (25 Polymer) Block Copolymer The title Ganetespib-conjugated block copolymer (Comparative Example B-1) was obtained according to the method described in Example B-1, using Copolymer 4 (2,300 mg) obtained in Synthesis Example 4 and 4-isopropyl-6-(4-(1-methyl-1H-indol-5-yl)-5-methylene-4,5-dihydro-1H-1,2,4-triazol-3-yl)benzene-1,3-diol (manufactured by Shanghai Haoyuan Chemexpress Co., Ltd., 557 mg).

Comparative Example B-1 was subjected to a hydrolysis treatment using a 1 N-aqueous solution of sodium hydroxide, and 4-isopropyl-6-(4-(1-methyl-1H-indol-5-yl)-5-methylene-4,5-dihydro-1H-1,2,4-triazol-3-yl)benzene-1,3-diol thus released was quantitatively determined by high performance liquid chromatography (HPLC) to thereby determine the content thereof. As a result, the content of 4-isopropyl-6-(4-(1-methyl-1H-indol-5-yl)-5-methylene-4,5-dihydro-1H-1,2,4-triazol-3-yl)benzene-1,3-diol in Example B-1 was 14.1% (w/w).

Comparative Example B-1 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the $^1$H-NMR spectrum, the ratio between the isopropylaminocarbonylisopropylamino group and the residue of 4-isopropyl-6-(4-(1-methyl-1H-indol-5-yl)-5-methylene-4,5-dihydro-1H-1,2,4-triazol-3-yl)benzene-1,3-diol was 0.13.

From these values, the total molecular weight of Comparative Example B-1 was calculated to be 17,311.

From this, the mass content of the polyethylene glycol segment was 69.3.

The light scattering intensity of a 1 mg/mL aqueous solution of Comparative Example B-1 was 294,722 cps, and the light scattering intensity of a standard toluene solution under the same conditions was 7,195 cps. Therefore, the relative ratio between the light scattering intensity of Example B-1 and the light scattering intensity of toluene was 41.0 times. The volume average particle diameter was 25 nm (device A, 1 mg/mL).

[Comparative Example B-2] Synthesis of 4-isopropyl-6-(4-(1-methyl-1H-indol-5-yl)-5-methylene-4,5-dihydro-1H-1,2,4-triazol-3-yl)benzene-1,3-diol and BODIPY-TR Conjugate of polyethylene glycol (12 Kilodaltons)-polyglutamic Acid (25 Polymer) Block Copolymer The title 4-isopropyl-6-(4-(1-methyl-1H-indol-5-yl)-5-methylene-4,5-dihydro-1H-1,2,4-triazol-3-yl)benzene-1,3-diol-conjugated block copolymer (Comparative Example B-2) was obtained according to the method described in Example B-2, using Copolymer 4 (170 mg) obtained in Synthesis Example 4 and 4-isopropyl-6-(4-(1-methyl-1H-indol-5-yl)-5-methylene-4,5-dihydro-1H-1,2,4-triazol-3-yl)benzene-1,3-diol (manufactured by Shanghai Haoyuan Chemexpress Co., Ltd., 41 mg) and BODIPY-TR Cadaverine.HCl (manufactured by Life Technologies Corp., 6 mg).

Comparative Example B-2 was subjected to a hydrolysis treatment using a 1 N-aqueous solution of sodium hydroxide, and 4-isopropyl-6-(4-(1-methyl-1H-indol-5-yl)-5-methylene-4,5-dihydro-1H-1,2,4-triazol-3-yl)benzene-1,3-diol thus released was quantitatively determined by high performance liquid chromatography (HPLC) to thereby determine the content thereof. As a result, the content of 4-isopropyl-6-(4-(1-methyl-1H-indol-5-yl)-5-methylene-4,5-dihydro-1H-1,2,4-triazol-3-yl)benzene-1,3-diol in Example 1 was 14.2% (w/w).

Comparative Example B-2 was hydrolyzed in a deuterated water-deuterated acetonitrile solution including deuterated sodium hydroxide, and a $^1$H-NMR spectrum of the solution thus obtained was analyzed. Thereby, it was confirmed that an isopropylaminocarbonylisopropylamino group was linked to a side chain carboxyl group of the polyglutamic acid segment. From the integral ratio of the H-NMR spectrum, the ratio between the isopropylaminocarbonylisopropylamino group and the residue of 4-isopropyl-6-(4-(1-methyl-1H-indol-5-yl)-5-methylene-4,5-dihydro-1H-1,2,4-triazol-3-yl)benzene-1,3-diol was 0.39.

The BODIPY-TR conjugation amount of Comparative Example B-2 was 1.0 molecule, as calculated from the consumption ratio of BODIPY-TR in the reaction solution measured by high performance liquid chromatography (HPLC). Therefore, the total molecular weight of BODIPY-TR in Comparative Example B-2 was calculated to be 334.

From these values, the total molecular weight of Comparative Example B-2 was calculated to be 18,171.

From this, the content of BODIPY-FL in Comparative Example-2 was 2.8% by mass, and the content of the polyethylene glycol segment was 66.0% by mass.

Comparative Example B-2 was used in the distribution test that will be described below, as a fluorescent labeled body of Comparative Example B-1.

[Test Example B-1] Intratumor and Intrarenal Distribution Test

A tumor mass of human pancreatic cancer BxPC3 that had been subcultured by subcutaneous transplantation in a BALB/c nude mouse was cut into a block having a size of about 3 mm on each side, and this block was subcutaneously transplanted on the dorsal side of a nude mouse using a trocar. Example B-2 and Comparative Example B-2 were respectively dissolved in a 5% glucose injection solution at a concentration of 5 mg/kg as converted to BODIPY, and equal amounts of the solutions were mixed. This mixture was intravenously administered once. One hour after the administration, blood was removed from the nude mouse under isoflurane anesthesia, frozen embedded slices of the tumor tissue and the kidney thus removed were produced, and fluorescence was observed. The results are presented in Table 3.

As a result of Test Example B-1, fluorescent signals were observed in a wide area of the tumor slices in the observation of the tumor slices in the administration example of Example B-2. From this, it was confirmed that the block copolymer of Example B-2 accumulated in the tumor tissue and penetrated into deep parts of the tumor tissue. In contrast, it was found in the case of Comparative Example B-2 that fluorescence was observed in the tumor shell region; however, fluorescent signals were not recognized at the central area of the tissue, and the block copolymer did not deliver the drug to the whole area of the tumor tissue.

In the kidneys, fluorescence was observed in the blood vessels and in the renal tubules in the case of Example B-2. On the other hand, fluorescence was not recognized in areas other than in the blood vessels in Comparative Example B-2.

From the above results, it was found that the block copolymer of Example B-2 exhibits accumulation in a tumor tissue including deep parts of the tumor tissue, also has a property of being excretable through the kidneys, and has controlled retention in vivo over a long time period.

[Test Example B-2] Hematotoxicity Test in Non-Tumor Bearing Mouse

[Drug Administration]

Example B-1 and Comparative Example B-1 were respectively dissolved in a 5' glucose injection solution, and the solutions were respectively intravenously administered once to 5-week old male ICR mice (Crl:CD1(ICR), Charles River Laboratories Japan, Inc.) through the caudal vein at a dose of 75 mg/kg as converted to 4-isopropyl-6-(4-(1-methyl-1H-indol-5-yl)-5-methylene-4,5-dihydro-1H-1,2,4-triazol-3-yl)benzene-1,3-diol, based on the body weight measured on the day of administration. As a control group, a 5% glucose injection solution was intravenously administered once through the caudal vein.

[Hematological Examination]

After 3 and 14 days from the day of administration of the various compounds, blood was collected through the subclavian vein without anesthesia using a 1-mL disposable syringe with a 26 G needle. About 3 µL of an EDTA-2K solution had been added in advance to the syringe, and this solution was sufficiently mixed with the blood thus collected. The resultant solutions were used as analysis samples. The blood samples were subjected to a blood cell analysis using a blood cell analysis apparatus XT-2000iV (Sysmex Corp.). The numbers of blood platelets obtained 3 days after the administration are presented in Table 4.

TABLE 4

Results of hematological examination (blood platelets)

| Drug | Number of platelets* |
| --- | --- |
| 5% glucose injection solution | 128.9 ± 13.7 |
| Example B-1 | 54.6 ± 6.6 |
| Comparative Example B-1 | 9.8 ± 3.5 |

*Number of blood platelets (×10$^4$/µL) in the 75 mg/kg-treated group on the 3$^{rd}$ day after administration As a result of the hematological examination, Comparative Example B-1 caused a decrease in the number of blood platelets after 3 days from the day of administration, and prolonged hematotoxicity was recognized. In contrast, in the case of the compound of present Examples B-2, the phenomenon concerning the number of platelets at the time point of 3 days after the administration was further suppressed as compared to Comparative Example B-1, and prolonged hematotoxicity occurred to a low extent.

Comparative Example B-1 is a compound having a molecular weight of 18 kilodaltons. Meanwhile, Example B-1 has a molecular weight of 4 kilodaltons, which is smaller. From the above results, it is considered that persistence of hematotoxicity of the resorcinol derivative-conjugated polymer derivative correlates with the molecular weight. Therefore, it was found that by employing a resorcinol compound-conjugated polymer derivative having a molecular weight of 15 kilodaltons or less, an antitumor agent that avoids persistence of hematotoxicity may be produced.

[Test Example B-3] Antitumor Effect in Human Colorectal Cancer and Human Breast Cancer-Transplanted Mouse A tumor mass of human colorectal cancer Col-5-JCK and Co-3-KIST that had been subcutaneously subcultured in a BALB/c nude mouse and a tumor mass of human breast cancer MC-19-JCK that had been subcutaneously subcultured in a SCID mouse were respectively cut into a block having a size of about 3 mm on each side, and these blocks were respectively subcutaneously transplanted on the dorsal side of a nude mouse or a SCID mouse using a trocar. At the time point when the average tumor volume reached about 150 mm$^3$ or more after the tumor transplantation, grouping was performed.

Example B-1 and Comparative Example B-1 were respectively dissolved in a 5% glucose injection solution, and the solutions were respectively intravenously administered once at a dose of 75 or 50 mg/kg as converted to 4-isopropyl-6-(4-(1-methyl-1H-indol-5-yl)-5-methylene-4,5-dihydro-1H-1,2,4-triazol-3-yl)benzene-1,3-diol.

As a control agent, 4-isopropyl-6-(4-(1-methyl-1H-indol-5-yl)-5-methylene-4,5-dihydro-1H-1,2,4-triazol-3-yl)benzene-1,3-diol (Ganetespib) was dissolved in DMSO, and then the solution was diluted 10 times with a mixed liquid of CREMOPHORE RH40:5% glucose solution (1:4). The dilution was intravenously administered once through the caudal vein at a dose of 150 mg/kg.

Relative tumor volumes were determined from the tumor volumes obtained on the day of initiation of administration, and these were employed as indices for the antitumor effect. The tumor volume was determined by measuring the major axis (L: mm) and the minor axis (W: mm) of the tumor, and calculating the volume by the calculation formula: $(L \times W^2)/2$. The results are presented in FIG. 4, FIG. 5, and FIG. 6.

Compared to Comparative Example B-1, Example B-1 exhibited a superior effect in both subcutaneous tumor models at the same dose. It is understood from the results of Test Example B-1 that Example B-1 has a property of migrating into a tumor tissue and a property of penetrating into deep parts of a tumor. Therefore, it is considered that the differences in pharmacokinetics in these tumor tissues are attributed to the antitumor effect-enhancing action.

[Synthesis Example 10] Synthesis of polyethylene glycol-α,β-polyaspartic Acid Block Copolymer (polyethylene glycol Molecular Weight: 2 Kilodaltons, Number of Polymerized Units of polyaspartic Acid: 12.5; Copolymer 10)

A polyethylene glycol having a single terminal methoxy group and a single terminal 3-aminopropyl group (SUNBRIGHT MEPA-20H, manufactured by NOF Corporation, average molecular weight: 2 kilodaltons, 20.0 g) was dissolved in DMSO (400 mL), and then γ-benzyl L-aspartate N-carboxylic acid anhydride (29.8 g, 12 equivalents) was added thereto. The mixture was stirred for 20 hours at 32.5° C. The reaction liquid was added dropwise for one hour to a mixed liquid of diisopropyl ether (3,200 mL) and ethanol (800 mL), and the resulting mixture was stirred for 3 hours at room temperature. Subsequently, a precipitate was collected by filtration and dried under reduced pressure, and thus a polymerization product (31.2 g) was obtained.

The polymerization product (30.0 g) thus obtained was dissolved in DMF (300 mL), acetic anhydride (7.3 mL) was added thereto, and the mixture was stirred for 3 hours at 35° C. The reaction liquid was added dropwise for one hour to a mixed liquid of diisopropyl ether (2,700 mL) and ethanol (300 mL), and the mixture was stirred for one hour at room temperature. Subsequently, a precipitate was collected by filtration and dried under reduced pressure, and thereby an acetylated polymer (26.6 g) was obtained.

The acetylated polymer (25.0 g) thus obtained was dissolved in MeCN (500 mL), and then 0.2 Normal sodium hydroxide (500 mL) was added thereto. The mixture was hydrolyzed for 3 hours at 23° C. The reaction liquid was neutralized by adding 2 Normal hydrochloric acid thereto, and then aceronitrile was removed by concentration under reduced pressure. Subsequently, the concentrate was washed three times using ethyl acetate (500 mL). An aqueous layer was concentrated under reduced pressure, and then the pH of the solution was adjusted to 11.0 with a 1 Normal aqueous solution of sodium hydroxide. Sodium chloride (50 g) was added thereto, and then the solution was purified using partition adsorption resin column chromatography followed by ion exchange resin column chromatography. The solution that had been eluted was concentrated under reduced pressure and then was freeze-dried. Thus, a polyethylene glycol-polyaspartic acid block copolymer (Copolymer 10: 13.0 g) was obtained.

Regarding Copolymer 10, the number of polymerized units of aspartic acid was calculated to be 12.5, based on the titration value obtained using 0.1 N potassium hydroxide.

The light scattering intensity of a 1 mg/mL aqueous solution of Synthesis Example 10 was 2,179 cps, and the light scattering intensity of a standard toluene solution under the same conditions was 7,305 cps. Therefore, the relative ratio between the light scattering intensity of Synthesis Example 10 and the light scattering intensity of toluene was 0.3 times.

[Synthesis Example 11] Synthesis of polyethylene glycol-α-polyaspartic Acid Block Copolymer (polyethylene glycol Molecular Weight: 5 Kilodaltons, Number of Polymerized Units of polyaspartic Acid: 20.0; Copolymer 11)

The title polyethylene glycol-α-polyaspartic acid block copolymer (Copolymer 11) was obtained according to the method described in Synthesis Example 2, using a polyethylene glycol having a single terminal methoxy group and a single terminal 3-aminopropyl group (SUNBRIGHT MEPA-50H, manufactured by NOF Corporation, average molecular weight: 5 kilodaltons) and γ-benzyl L-aspartate N-carboxylic acid anhydride.

Regarding Copolymer 11, the number of polymerized units of aspartic acid was calculated to be 20.0, based on the titration value obtained using 0.1 N potassium hydroxide.

[Synthesis Example 12] Synthesis of polyethylene glycol-α,β-polyaspartic Acid Block Copolymer (polyethylene glycol Molecular Weight: 12 Kilodaltons, Number of Polymerized Units of polyaspartic Acid: 23.8; Copolymer 12)

A polyethylene glycol having a single terminal methoxy group and a single terminal 3-aminopropyl group (SUNBRIGHT MEPA-12K, manufactured by NOF Corporation, average molecular weight: 12 kilodaltons, 75.0 g) was dissolved in DMSO (1,430 mL), and then γ-benzyl L-aspartate N-carboxylic acid anhydride (45.0 g, 29 equivalents) was added thereto. The mixture was stirred overnight at 32.0° C. The reaction liquid was added dropwise for one hour to a mixed liquid of diisopropyl ether (12 L) and ethanol (3 L), and the resulting mixture was stirred for one hour at room temperature. Subsequently, a precipitate was collected by filtration and dried under reduced pressure, and thus a polymerization product (106.0 g) was obtained.

The polymerization product (105.0 g) thus obtained was dissolved in DMF (1,050 mL), acetic anhydride (3.3 mL) was added thereto, and the mixture was stirred for 3 hours at 35° C. The reaction liquid was added dropwise for one hour to a mixed liquid of diisopropyl ether (2,9450 mL) and ethanol (1,050 mL), and the mixture was stirred for one hour at room temperature. Subsequently, a precipitate was collected by filtration and dried under reduced pressure, and thereby an acetylated polymer (103.0 g) was obtained.

The acetylated polymer (100.0 g) thus obtained was dissolved in acetonitrile (2 L), and then 0.2 Normal sodium hydroxide (2 L) was added thereto. The mixture was hydrolyzed for 3 hours at 23° C. The reaction liquid was neutralized by adding 2 Normal hydrochloric acid thereto, and then acetonitrile was removed by concentration under reduced pressure. Subsequently, the concentrate was washed three times using ethyl acetate (2 L). An aqueous layer was concentrated under reduced pressure, and then the pH of the solution was adjusted to 11.0 with a 1 Normal aqueous solution of sodium hydroxide. Sodium chloride (100 g) was added thereto, and then the solution was purified using partition adsorption resin column chromatography followed by ion exchange resin column chromatography. The solution that had been eluted was concentrated under reduced pressure and then was freeze-dried. Thus, a polyethylene glycol-polyaspartic acid block copolymer (Copolymer 12: 75.4 g) was obtained.

Regarding Copolymer 12, the number of polymerized units of aspartic acid was calculated to be 23.8, based on the titration value obtained using 0.1 N potassium hydroxide.

[Example C-1] Synthesis of Cabazitaxel (CBZ) and n-butylamine Conjugate of polyethylene glycol (2 Kilodaltons)-α,β-polyaspartic Acid (12.5 Polymer) Block Copolymer Copolymer 10 (707.6 mg) obtained in Synthesis Example 10 and cabazitaxel (CBZ 572.2 mg) were dissolved in N-methylpyrrolidone (NMP 19.5 mL), and n-butylamine (125 µL), dimethylaminopyridine (DMAP 154.9 mg), and diisopropylcarbodiimide (DIPCI 911 µL) were added thereto. The mixture was stirred for 19 hours at 25° C. Subsequently, DIPCI (228 µL) was further added thereto, and the resulting mixture was stirred for 6 hours. Ethyl acetate (20 mL) was added to the reaction liquid, and then the reaction liquid was added dropwise for one hour to diisopropyl ether (1,560 mL). The mixture was stirred for one hour at room temperature, and then a precipitate was collected by filtration and dried under reduced pressure. Thus, a product (950 mg) was obtained. The product thus obtained was dissolved in acetonitrile/water (50/50 (v/v), 140 mL), and then an ion exchange resin was added thereto. The mixture was stirred for 30 minutes at 5° C. The ion exchange resin was separated by filtration, subsequently acetonitrile was distilled off under reduced pressure, and the residue was freeze-dried. Thus, the title taxane compound-conjugated polymer derivative (Example C-1, 930 mg) was obtained.

The CBZ conjugation amount of Example C-1 was 1.3 molecules, as calculated from the consumption ratio of CBZ in the reaction solution measured by high performance liquid chromatography (HPLC). Therefore, the total molecular weight of CBZ in Example C-1 was calculated to be 1,087.

The n-butylamine conjugation amount of Example C-1 was 6.2 molecules, when it was assumed that the entire amount of n-butylamine introduced was used for the reaction. Therefore, the total molecular weight of n-butylamine in Example C-1 was calculated to be 453.

From these values, the total molecular weight of Example C-1 was calculated to be 5,516.

From this, the content of CBZ in Example C-1 was 19.7% by mass, the content of n-butylamine was 8.2% by mass, and the content of the polyethylene glycol segment was 36.3% by mass.

The light scattering intensity of a 1 mg/mL aqueous solution of Example C-1 was 13,018 cps, and the light scattering intensity of a standard toluene solution under the same conditions was 4,368 cps. Therefore, the relative ratio between the light scattering intensity of Example C-1 and the light scattering intensity of toluene was 3.0 times. The volume average particle diameter was 6.3 nm (device A, 1 mg/mL).

[Example C-2] Synthesis of Cabazitaxel (CBZ) Conjugate of polyethylene glycol (5 Kilodaltons)-α-polyaspartic Acid (20.0 Polymer) Block Copolymer Copolymer 11 (1.50 g) obtained in Synthesis Example 11 and cabazitaxel (CBZ 342 mg) were dissolved in NMP (31 mL), and dimethylaminopyridine (DMAP 250 mg) and diisopropylcarbodiimide (DIPCI 1468 µL) were added thereto. The mixture was stirred for 21 hours at 20° C. Subsequently, DIPCI (367 µL) was further added thereto, and the resulting mixture was stirred for 5 hours. Ethyl acetate (31 mL) was added to the reaction liquid, and then the reaction liquid was added dropwise for one hour to diisopropyl ether (1,260 mL). The mixture was stirred for one hour at room temperature, and then a precipitate was collected by filtration and dried under reduced pressure. Thus, a product (1.71 g) was obtained. The product thus obtained was dissolved in acetonitrile/water (50/50 (v/v), 80 mL), and then an ion exchange resin was added thereto. The mixture was stirred for 30 minutes at 5° C. The ion exchange resin was separated by filtration, subsequently acetonitrile was distilled off under reduced pressure, and the residue was freeze-dried. Thus, the title taxane compound-conjugated polymer derivative (Example C-2, 1.58 g) was obtained.

The CBZ conjugation amount of Example C-2 was 1.6 molecules, as calculated from the consumption ratio of CBZ in the reaction solution measured by high performance liquid chromatography (HPLC). Therefore, the total molecular weight of CBZ in Example C-2 was calculated to be 1,337.

From these values, the total molecular weight of Example C-2 was calculated to be 10,970.

From this, the content of CBZ in Example C-2 was 12.2% by mass, and the content of the polyethylene glycol segment was 45.6% by mass.

The light scattering intensity of a 1 mg/mL aqueous solution of Example C-2 was 10,382 cps, and the light scattering intensity of a standard toluene solution under the same conditions was 4,187 cps. Therefore, the relative ratio between the light scattering intensity of Example C-2 and the light scattering intensity of toluene was 2.5 times. The volume average particle diameter was 10 nm (device B, 1 mg/mL).

[Example C-3] Synthesis of Cabazitaxel (CBZ)/n-butylamine/2-(2-aminoethoxy)-9-(diethylamino)-5H-benzo[a]phenoxazin-5-one Conjugate of polyethylene glycol (2 Kilodaltons)-α,β-polyaspartic Acid (12.5 Polymer) Block Copolymer Copolymer 10 (205.6 mg) obtained in Synthesis Example 10, cabazitaxel (CBZ 166.3 mg), and 2-(2-aminoethoxy)-9-(diethylamino)-5H-benzo[a]phenoxazin-5-one (5.1 mg) were dissolved in NMP (5.7 mL), and n-butylamine (36 µL), dimethylaminopyridine (DMAP 45.0 mg), and diisopropylcarbodiimide (DIPCI 265 µL) were added thereto. The mixture was stirred for 17.5 hours at 20° C. Subsequently, DIPCI (66 µL) was further added thereto, and the resulting mixture was stirred for 4.5 hours. Ethyl acetate (5.5 mL) was added to the reaction liquid, and then the reaction liquid was added dropwise for 10 minutes to diisopropyl ether (440 mL). The mixture was stirred for one hour at room temperature, and then a precipitate was collected by filtration and dried under reduced pressure. Thus, a product (300 mg) was obtained. The product thus obtained was dissolved in acetonitrile/water (50/50 (v/v), 20 mL), and then an ion exchange resin was added thereto. The mixture was stirred for 30 minutes at 5° C. The ion exchange resin was separated by filtration, subsequently acetonitrile was distilled off under reduced pressure, and the residue was freeze-dried. Thus, the title taxane compound-conjugated polymer derivative (Example C-3, 270.9 mg) was obtained.

The CBZ conjugation amount of Example C-3 was 1.7 molecules, as calculated from the consumption ratio of CBZ in the reaction solution measured by high performance liquid chromatography (HPLC). Therefore, the total molecular weight of CBZ in Example C-3 was calculated to be 1,421.

The n-butylamine conjugation amount of Example C-3 was 6.2 molecules, when it was assumed that the entire amount of n-butylamine introduced was used for the reaction. Therefore, the total molecular weight of n-butylamine in Example C-3 was calculated to be 453.

The 2-(2-aminoethoxy)-9-(diethylamino)-5H-benzo[a]phenoxazin-5-one conjugation amount of Example C-3 was 0.23 molecules, as calculated from the consumption ratio of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Example C-3 was calculated to be 87.

From these values, the total molecular weight of Example C-3 was calculated to be 5,846.

From this, the content of CBZ in Example C-3 was 24.3% by mass, the content of n-butylamine was 7.8% by mass, the content of 2-(2-aminoethoxy)-9-(diethylamino)-5H-benzo[a]phenoxazin-5-one was 1.5% by mass, and the content of the polyethylene glycol segment was 34.2% by mass.

Example C-3 was used in the distribution test that will be described below, as a fluorescent labeled body of Example C-1.

[Example C-4] Synthesis of Cabazitaxel (CBZ) Conjugate of polyethylene glycol (2 Kilodaltons)-α,β-polyaspartic Acid (12.5 Polymer) Block Copolymer Copolymer 10 (51.5 mg) obtained in Synthesis Example 10 and cabazitaxel (CBZ 30.9 mg) were dissolved in N-methylpyrrolidone (NMP 1.42 mL), and dimethylaminopyridine (DMAP 11.3 mg) and diisopropylcarbodiimide (DIPCI 66 µL) were added thereto. The mixture was stirred for 13 hours at 25° C. Subsequently, DIPCI (17 µL) was further added thereto, and the resulting mixture was stirred for 5 hours. Ethyl acetate (1.42 mL) was added to the reaction liquid, and then the reaction liquid was added dropwise for one hour to diisopropyl ether (114 mL). The mixture was stirred for one hour at room temperature, and then a precipitate was collected by filtration and dried under reduced pressure. Thus, the title taxane compound-conjugated polymer derivative (Example C-4) was obtained.

The CBZ conjugation amount of Example C-4 was 1.8 molecules, as calculated from the consumption ratio of CBZ in the reaction solution measured by high performance liquid chromatography (HPLC). Therefore, the total molecular weight of CBZ in Example C-4 was calculated to be 1,505.

From these values, the total molecular weight of Example C-4 was calculated to be 6,301.

From this, the content of CBZ in Example C-4 was 23.9% by mass, and the content of the polyethylene glycol segment was 31.7% by mass.

The light scattering intensity of a 1 mg/mL aqueous solution of Example C-4 was 176,886 cps, and the light scattering intensity of a standard toluene solution under the same conditions was 7,156 cps. Therefore, the relative ratio between the light scattering intensity of Example C-4 and the light scattering intensity of toluene was 24.7 times. The volume average particle diameter was 12 nm (device A, 1 mg/mL).

[Example C-5] Synthesis of docetaxel (DTX) and 4-phenylbutylamine Conjugate of polyethylene glycol (2 kilodaltons)-α,β-polyaspartic Acid (12.5 Polymer) Block Copolymer Copolymer 10 (33.4 mg) obtained in Synthesis Example 10 and docetaxel (DTX 26.1 mg) were dissolved in N-methylpyrrolidone (NMP 0.92 mL), and 4-phenylbutylamine (6 µL), dimethylaminopyridine (DMAP 7.3 mg), and diisopropylcarbodiimide (DIPCI 43 µL) were added thereto. The mixture was stirred for 22 hours at 25° C. Subsequently, DIPCI (11 µL) was further added thereto, and the resulting mixture was stirred for another 6 hours. The reaction liquid was transferred into a dialysis membrane with MWCO 2,000 and was dialyzed in water, and the resultant was freeze-dried. Thus, the title taxane compound-conjugated polymer derivative (Example C-5, 59.6 mg) was obtained.

The DTX conjugation amount of Example C-5 was 1.2 molecules, as calculated from the consumption ratio of DTX in the reaction solution measured by high performance liquid chromatography (HPLC). Therefore, the total molecular weight of DTX in Example C-5 was calculated to be 969.

The 4-phenylbutylamine conjugation amount of Example C-5 was 3.7 molecules, when it was assumed that the entire amount of 4-phenylbutylamine introduced was used for the reaction. Therefore, the total molecular weight of 4-phenylbutylamine in Example C-5 was calculated to be 552.

From these values, the total molecular weight of Example C-5 was calculated to be 5,872.

From this, the content of DTX in Example C-5 was 16.5% by mass, the content of 4-phenylbutylamine was 9.4% by mass, and the content of the polyethylene glycol segment was 34.1% by mass.

The light scattering intensity of a 1 mg/mL aqueous solution of Example C-5 was 162,126 cps, and the light scattering intensity of a standard toluene solution under the same conditions was 7,152 cps. Therefore, the relative ratio between the light scattering intensity of Example C-5 and the light scattering intensity of toluene was 22.7 times.

[Comparative Example C-1] Synthesis of Cabazitaxel (CBZ) Conjugate of polyethylene glycol (12 Kilodaltons)-α,β-polyaspartic Acid (23.8 Polymer) Block Copolymer Copolymer 12 (1.60 g) obtained in Synthesis Example 12 and cabazitaxel (CBZ 797.9 mg) were dissolved in N-methylpyrrolidone (NMP 20.2 mL), and dimethylaminopyridine (DMAP 35.2 mg) and diisopropylcarbodiimide (DIPCI 942 µL) were added thereto. The mixture was stirred for 21 hours at 15° C. Subsequently, DIPCI (236 µL) was further added thereto, and the resulting mixture was stirred for another 7 hours. The reaction liquid was added dropwise for 1 hour to a mixed liquid of diisopropyl ether (360 mL) and ethanol (90 mL). The mixture was stirred for one hour at room temperature, and then a precipitate was collected by filtration and dried under reduced pressure. Thus, a product (1.98 g) was obtained. The product thus obtained was dissolved in acetonitrile/water (50/50 (v/v), 80 mL), and then an ion exchange resin was added thereto. The mixture was stirred for 30 minutes at 5° C. The ion exchange resin was separated by filtration, subsequently acetonitrile was distilled off under reduced pressure, and the residue was freeze-dried. Thus, the title taxane compound-conjugated polymer derivative (Comparative Example C-1, 1.93 g) was obtained.

The CBZ conjugation amount of Comparative Example C-1 was 5.2 molecules, as calculated from the consumption ratio of CBZ in the reaction solution measured by high performance liquid chromatography (HPLC). Therefore, the total molecular weight of CBZ in Comparative Example C-1 was calculated to be 4,347.

From these values, the total molecular weight of Comparative Example C-1 was calculated to be 21,377.

From this, the content of CBZ in Comparative Example C-1 was 20.3% by mass, and the content of the polyethylene glycol segment was 56.1% by mass.

The light scattering intensity of a 1 mg/mL aqueous solution of Comparative Example C-1 was 24,804 cps, and the light scattering intensity of a standard toluene solution under the same conditions was 4,368 cps. Therefore, the relative ratio between the light scattering intensity of Comparative Example C-1 and the light scattering intensity of toluene was 5.7 times. The volume average particle diameter was 22 nm (device A, 1 mg/mL).

[Comparative Example C-2] Synthesis of Cabazitaxel (CBZ) and 2-(2-aminoethoxy)-9-(diethylamino)-5H-benzo[a]phenoxazin-5-one Conjugate of polyethylene glycol (12 Kilodaltons)-α,β-polyaspartic Acid (23.8 Polymer) Block Copolymer Copolymer 12 (200 mg) obtained in Synthesis Example 12, cabazitaxel (CBZ 99.7 mg), and 2-(2-aminoethoxy)-9-(diethylamino)-5H-benzo[a]phenoxazin-5-one (5.2 mg) were dissolved in N-methylpyrrolidone (NMP 2.5 mL), and dimethylaminopyridine (DMAP 4.4 mg) and diisopropylcarbodiimide (DIPCI 118 µL) were added thereto. The mixture was stirred for 21 hours at 20° C. Subsequently, DIPCI (29 µL) was further added thereto, and the resulting mixture was stirred for another 5 hours. The reaction liquid was added dropwise for 10 minutes to a mixed liquid of diisopropyl ether (18 mL) and ethanol (4.5 mL), and the mixture was stirred for one hour at room temperature. Subsequently, a precipitate was collected by filtration and was dried under reduced pressure. Thus, a product (235.0 mg) was obtained. The product thus obtained was dissolved in acetonitrile/water (50/50 (v/v), 10 mL), and then an ion exchange resin was added thereto. The mixture was stirred for 30 minutes at 5° C. The ion exchange resin was separated by filtration, subsequently acetonitrile was distilled off under reduced pressure, and the residue was freeze-dried. Thus, the title taxane compound-conjugated polymer derivative (Comparative Example C-2, 205.6 mg) was obtained.

The CBZ conjugation amount of Comparative Example C-2 was 4.3 molecules, as calculated from the consumption ratio of CBZ in the reaction solution measured by high performance liquid chromatography (HPLC). Therefore, the total molecular weight of CBZ in Comparative Example C-2 was calculated to be 3,594.

The 2-(2-aminoethoxy)-9-(diethylamino)-5H-benzo[a]phenoxazin-5-one conjugation amount of Comparative Example C-2 was 1.0 molecule, as calculated from the consumption ratio of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Comparative Example C-2 was calculated to be 377.

From these values, the total molecular weight of Comparative Example C-2 was calculated to be 20,988.

From this, the content of CBZ in Comparative Example C-2 was 17.1% by mass, the content of 2-(2-aminoethoxy)-9-(diethylamino)-5H-benzo[a]phenoxazin-5-one was 1.8% by mass, and the content of the polyethylene glycol segment was 57.2% by mass.

Comparative Example C-2 was used in the distribution test that will be described below, as a fluorescent labeled body of Comparative Example C-1.

[Comparative Example C-3] Synthesis of 2-(2-aminoethoxy)-9-(diethylamino)-5H-benzo[a]phenoxazin-5-one Conjugate of polyethylene glycol (2 Kilodaltons)-α,β-polyaspartic Acid (12.5 Polymer) Block Copolymer Copolymer 10 (205.7 mg) obtained in Synthesis Example 10 and 2-(2-aminoethoxy)-9-(diethylamino)-5H-benzo[a]phenoxazin-5-one (5.1 mg) were dissolved in N-methylpyrrolidone (NMP 5.7 mL), and dimethylaminopyridine (DMAP 45.0 mg) and diisopropylcarbodiimide (DIPCI 265 µL) were added thereto. The mixture was stirred for 18.5 hours at 20° C. Subsequently, DIPCI (66 µL) was further added thereto, and the resulting mixture was stirred for another 2.5 hours. The reaction liquid was transferred into a dialysis membrane with MWCO 10,000 and was dialyzed in water, and the resultant was freeze-dried. Thus, the title taxane compound-conjugated polymer derivative (Comparative Example C-3, 247.7 mg) was obtained.

The 2-(2-aminoethoxy)-9-(diethylamino)-5H-benzo[a]phenoxazin-5-one conjugation amount of Comparative Example C-3 was 0.3 molecules, as calculated from the consumption ratio of 2-(2-aminoethoxy)-9-(diethylamino)-5H-benzo[a]phenoxazin-5-one in the reaction solution measured by high performance liquid chromatography (HPLC). Therefore, the total molecular weight of 2-(2-aminoethoxy)-9-(diethylamino)-5H-benzo[a]phenoxazin-5-one in Comparative Example C-3 was calculated to be 113.

From these values, the total molecular weight of Comparative Example C-3 was calculated to be 5,126.

From this, the content of 2-(2-aminoethoxy)-9-(diethylamino)-5H-benzo[a]phenoxazin-5-one in Comparative Example C-3 was 2.2% by mass, and the content of the polyethylene glycol segment was 39.0% by mass.

Comparative Example C-3 was non-associating, and was used in the distribution test that will be described below, as a fluorescent labeled body of Copolymer 12.

[Test Example C-1] Intratumor and Intrarenal Distribution Test

A tumor mass of human pancreatic cancer BxPC3 that had been subcultured by subcutaneous transplantation in a BALB/c nude mouse was cut into a block having a size of about 3 mm on each side, and this block was subcutaneously transplanted on the dorsal side of a nude mouse using a trocar. Example C-3, Comparative Example C-2, and Comparative Example C-3 were respectively dissolved in a 5% glucose injection solution, and the solutions were respectively intravenously administered once at a dose of 5 mg/kg as converted to 2-(2-aminoethoxy)-9-(diethylamino)-5H-benzo[a]phenoxazin-5-one. One hour after the administration, blood was removed from the mouse under isoflurane anesthesia, frozen embedded slices of the removed tumor and the kidneys were produced, and fluorescence was observed. The results are presented in FIG. 7.

As a result of Test Example C-1, fluorescent signals were observed in a wide area of the tumor slices in the case of Example C-3. From this, it was shown that the block copolymer of Example C-3 is capable of migrating to and accumulating in the tumor tissue, and is also capable of penetrating into deep parts of the tumor tissue. In contrast, it was found in the cases of Comparative Example C-2 and Comparative Example C-3 that fluorescent signals were observed in the fringe area of the tumor; however, properties of penetrating into the tumor tissue were not confirmed, and migration and accumulation in the tumor tissue was low.

In the kidneys, fluorescence was observed in the renal tubules in the cases of Example C-3 and Comparative Example C-3. Meanwhile, in the case of Comparative Example C-2, fluorescence was not recognized in areas other than the blood vessels. From this, it was found that Example C-3 has a property of being rapidly excretable through the kidneys, compared to Comparative Example C-2.

The non-associating block copolymer of Comparative Example C-3, which had a molecular weight of less than 15 kilodaltons, and in which the analysis value represented by the light scattering intensity in an aqueous solution was less than twice, was rapidly excretable through the kidneys; however, the block copolymer showed low accumulation in the tumor. The taxane compound-conjugated block copolymer of Comparative Example C-2, which had a molecular weight of more than 15 kilodaltons, and in which the analysis value represented by the light scattering intensity in an aqueous solution was twice or more, was not excretable through the kidneys; however, accumulation in the tumor was lower compared to Example C-3. It became clear that a taxane compound-conjugated block copolymer that is rapidly excretable through the kidneys and exhibits accumulation in the tumor may be produced by adjusting the analysis value represented by the light scattering intensity in an aqueous solution to be twice or more, and adjusting the molecular weight to 15 kilodaltons or less.

[Test Example C-2] Hematotoxicity Test in Non-Tumor Bearing Mouse

[Drug Administration]

Example C-1 and Comparative Example C-1 were respectively dissolved in a 5% glucose injection solution, and the solutions were respectively intravenously administered once to 5-week old male ICR mice (Crl:CD1 (ICR), Charles River Laboratories Japan, Inc.) through the caudal vein at a dose of 60 mg/kg as converted to cabazitaxel, which were the maximum tolerated doses for the various compounds, based on the body weight measured on the day of administration. As a control group, a 5% glucose injection solution was intravenously administered once through the caudal vein.

For the compounds of Example C-1 and Comparative Example C-1, a necessary amount of each compound that had been calculated as converted to the cabazitaxel content was weighed in a polypropylene centrifuge tube, a 5% glucose injection solution was added thereto, and the compound was dissolved therein by irradiating the solution with ultrasonic waves in ice-cold water.

For cabazitaxel as an object drug, a necessary amount calculated to give a concentration of 20 times a predetermined concentration was weighed in a polypropylene centrifuge tube, and anhydrous ethanol was added thereto to dissolve the compound. Polysorbate 80 was added thereto in an amount equal to the amount of anhydrous ethanol, and the mixture was sufficiently mixed. This was used as a preparation stock solution. The preparation stock solution was diluted 10 times with a 5% glucose injection liquid immediately before administration, and the dilution was intravenously administered once through the caudal vein at a dose of 30 mg/kg, which is the maximum non-lethal dose.

[Hematological Examination]

After 3, 5, 7, 11, and 14 days from the day of administration of the various compounds, blood was collected through the subclavian vein without anesthesia using a 1-mL disposable syringe with a 26 G needle. About 3 μL of an EDTA-2K solution had been added in advance to the syringe, and this solution was sufficiently mixed with the blood thus collected. The resultant solutions were used as analysis samples. The blood samples were subjected to a blood cell analysis using a blood cell analysis apparatus XT-2000iV (Sysmex Corp.). The numbers of blood reticulocytes obtained 5 days after the administration are presented in Table 5.

TABLE 5

Results of hematological examination (blood reticulocytes)

| Drug | Number of blood reticulocytes* |
|---|---|
| 5% glucose injection solution | 36.09 ± 5.34 |
| Example C-1 | 52.69 ± 13.95 |

TABLE 5-continued

Results of hematological examination (blood reticulocytes)

| Drug | Number of blood reticulocytes* |
|---|---|
| Comparative Example C-1 | 18.49 ± 13.10 |
| Cabazitaxel | 93.07 ± 19.21 |

*Number of blood reticulocytes (×10$^4$/μL) in various treated groups on the 5$^{th}$ day after administration As a result of the hematological examination, Comparative Example C-1 caused a decrease in the number of blood reticulocytes after 5 days from the day of administration, and prolonged hematotoxicity was recognized. In contrast, the compound of Examples C-1 and cabazitaxel did not cause a decrease in the number of blood reticulocytes at the time point of 5 days after the administration, and prolonged hematotoxicity was not recognized. Therefore, it is speculated that the compounds of Example C-1 and cabazitaxel did not protract hematotoxicity.

Comparative Example C-1 is a compound having a molecular weight of 21 kilodaltons. On the other hand, Examples C-1 has a small molecular weight, which is 5.5 kilodaltons. From the above results, it is considered that persistence of hematotoxicity of a taxane derivative-conjugated block copolymer correlates with the molecular weight. Therefore, by employing a taxane derivative-conjugated block copolymer having a molecular weight of 15 kilodaltons or less, an antitumor agent that avoids persistence of hematotoxicity may be produced.

[Test Example C-3] Antitumor Effect Test in Human Pancreatic Cancer-Transplanted Nude Mouse A tumor mass of human pancreatic cancer BxPC3 that had been subcutaneously subcultured in a nude mouse was cut into a block having a size of about 3 mm on each side, and this block was subcutaneously transplanted on the dorsal side of a nude mouse using a trocar. At the time point when the average tumor volume reached about 200 mm$^3$ or more after the tumor transplantation, Example C-1, Example C-2, and Comparative Example C-1 were respectively dissolved in a 5% glucose injection solution, and the solutions were respectively intravenously administered once through the caudal vein at a dose of 60 mg/kg as converted to cabazitaxel, which were the maximum tolerated doses for the various compounds, based on the body weight measured on the day of administration.

Regarding cabazitaxel, a solution obtained by dissolving cabazetaxel in Polysorbate 80 and then diluting the solution in an equal amount of anhydrous ethanol, was used as a preparation stock solution. The preparation stock solution was diluted 10 times with a 5% glucose injection solution immediately before administration, and the dilution was intravenously administered once through the caudal vein at a dose of 30 mg/kg, which is the maximum non-lethal dose.

A relative tumor volume was determined from the tumor volumes obtained on the day of administration and on the 8$^{th}$ day after the administration, and this was employed as an index for the antitumor effect. The tumor volume was determined by measuring the major axis (L: mm) and the minor axis (W: mm) of the tumor, and calculating the volume by the calculation formula: (L×W$^2$)/2. The results are presented in Table 6.

TABLE 6

Results of antitumor effect test against human pancreatic cancer BxPC3-transplanted nude mouse

| Drug | Relative tumor volume* |
|---|---|
| Not administered | 2.78 ± 1.05 |
| Example C-1 | 0.83 ± 0.10 |
| Example C-2 | 0.81 ± 0.17 |
| Comparative Example C-1 | 0.78 ± 0.09 |
| Cabazitaxel | 1.19 ± 0.21 |

*Relative tumor volume (average ± SD) in various treated groups on the 8$^{th}$ day after administration in a case in which the tumor volume on the day of drug administration is designated as 1.0

As a result of Test Example C-3, Example C-1, Example C-2, and Comparative Example C-1 resulted in small tumor volumes compared to cabazitaxel, and exhibited stronger tumor proliferation suppressing action.

[Test Example C-4] Antitumor Effect Test in Human Lung Cancer-Transplanted Nude Mouse A tumor mass of human lung cancer H460 that had been subcutaneously subcultured in a nude mouse was cut into a block having a size of about 3 mm on each side, and this block was subcutaneously transplanted on the dorsal side of a nude mouse using a trocar. At the time point when the average tumor volume reached about 200 mm$^3$ or more after the tumor transplantation, Example C-1, Example C-2, and Comparative Example C-1 were respectively dissolved in a 5% glucose injection solution, and the solutions were respectively intravenously administered once through the caudal vein at a dose of 60 mg/kg as converted to cabazitaxel, which were the maximum tolerated doses for the various compounds, based on the body weight measured on the day of administration.

Regarding cabazitaxel, a solution obtained by dissolving cabazetaxel in Polysorbate 80 and then diluting the solution in an equal amount of anhydrous ethanol, was used as a preparation stock solution. The preparation stock solution was diluted 10 times with a 5% glucose injection solution immediately before administration, and the dilution was intravenously administered once through the caudal vein at a dose of 30 mg/kg, which is the maximum non-lethal dose.

A relative tumor volume was determined from the tumor volumes obtained on the day of administration and on the 15$^{th}$ day after the administration, and this was employed as an index for the antitumor effect. The tumor volume was determined by measuring the major axis (L: mm) and the minor axis (W: mm) of the tumor, and calculating the volume by the calculation formula: (L×W$^2$)/2. The results are presented in Table 7.

TABLE 7

Results of antitumor effect test against human lung cancer H460-transplanted nude mouse

| Drug | Relative tumor volume* |
|---|---|
| Not administered | 2.940 ± 0.704 |
| Example C-1 | 0.560 ± 0.201 |
| Example C-2 | 0.800 ± 0.371 |
| Comparative Example C-1 | 0.484 ± 0.083 |
| Cabazitaxel | 1.476 ± 0.509 |

*Relative tumor volume (average ± SD) in various treated groups on the 15$^{th}$ day after administration in a case in which the tumor volume on the day of drug administration is designated as 1.0

As a result of Test Example C-4, Example C-1, Example C-2, and Comparative Example C-1 resulted in small tumor volumes compared to cabazitaxel, and exhibited stronger tumor proliferation suppressing action.

From the results of Test Examples C-1 to C-4, it is clearly shown that the present taxane derivative-conjugated block copolymers suppress persistence of hematotoxicity while manifesting an antitumor effect that is equivalent or superior to that of control drugs. Therefore, it has become clear that when a taxane derivative-conjugated block copolymer having a controlled molecular weight and a controlled light scattering intensity in an aqueous solution is used, an antitumor agent that is capable of avoiding the normal tissue injuring action from the tumor proliferation suppressing action, and of achieving efficacy enhancement and reduction of adverse effects, may be provided.

From the results described above, it has become clear that, in regard to a DDS preparation that uses a block copolymer in which a polyethylene glycol segment is connected with a polyamino acid segment, as a drug delivery carrier, when the molecular weight of the block copolymer is controlled to be 2 kilodaltons or more and 15 kilodaltons or less, and when a property of forming self-associating particles in an aqueous solution is imparted to the block copolymer in connection with the analysis of properties in an aqueous solution according to a laser light scattering photometry method, a nanoparticle DDS preparation having a volume average particle diameter that is smaller than conventional DDS preparations may be produced, and thereby, the DDS preparation exhibits pharmacokinetics characteristics that are not observed in conventional block copolymers.

That is, it is obvious that the block copolymer according to the present invention has not only tissue-migration properties of migrating to a target diseased tissue such as a tumor, but also superior properties of penetrating into the interior of a tissue. Thus, the block copolymer manifests a superior property of migrating to a target tissue and superior accumulation. Furthermore, it has been known that DDS preparations that use polymer carriers have suppressed excretability through the kidneys; however, it is clearly shown that the block copolymer according to the present invention is excretable through the kidneys. Such unique pharmacokinetics characteristics are properties attributed to the molecular weight of the block copolymer and self-associating properties, and it was found that these pharmacokinetics characteristics provide a technology for formulating a generally usable DDS preparation, irrespective of the type or chemical structure of the physiologically active substance to be conjugated. Since such pharmacokinetics characteristics enable delivery of a physiologically active substance to deep parts of a target diseased tissue and sensitization to the target diseased tissue, the pharmacological activity effect may be efficiently manifested. Furthermore, since the block copolymer is excretable through the kidneys, the block copolymer molecules that are not distributed and accumulated in the target diseased tissue are rapidly excreted. Therefore, unnecessary retention in vivo is suppressed, and manifestation of adverse effects may be reduced by avoiding distribution and accumulation in tissues other than a target diseased tissue.

Thus, the block copolymer according to the present invention is a technology that enables introduction of a new concept for macromolecularized DDS preparations, and thus useful pharmaceutical products may be provided by applying the block copolymer to medicines that are provided for the treatment of various diseases. Particularly, it is preferable to use the block copolymer for the treatment of local tissue diseases, and pharmaceutical products for treating malignant tumor disease, inflammatory diseases, and infectious diseases may be applied to the block copolymer.

The invention claimed is:

1. A block copolymer comprising a polyethylene glycol segment connected with a polyamino acid derivative segment including an aspartic acid derivative and/or a glutamic acid derivative, and the polyamino acid derivative segment having a physiologically active substance with a hydroxyl group linked through a bond or a linking group having a carboxyl group to a side chain carboxyl group of the derivative, wherein the hydroxyl group of the physiologically active substance forms an ester bond with the side chain carboxyl group of the derivative or the carboxyl group included in the linking group, wherein the molecular weight of the block copolymer is from 2 kilodaltons to 15 kilodaltons, and the light scattering intensity of a 1 mg/mL aqueous solution of the block copolymer as measured with a laser light scattering photometer under the measurement conditions of a measurement temperature of 25° C., a scattering angle of 90°, and a wavelength of 632.8 nm, is at least twice or more the light scattering intensity of toluene measured under the same measurement conditions.

2. A block copolymer comprising a polyethylene glycol segment connected with a polyamino acid derivative segment including an aspartic acid derivative and/or a glutamic acid derivative, and the polyamino acid derivative segment having a physiologically active substance with a hydroxyl group linked through a bond or a linking group having a carboxyl group to a side chain carboxyl group of the derivative, wherein the hydroxyl group of the physiologically active substance forms an ester bond with the side chain carboxyl group of the derivative or the carboxyl group included in the linking group, wherein the block copolymer has a nanoparticle-forming ability, and the molecular weight of the block copolymer is from 2 kilodaltons to 15 kilodaltons.

3. The block copolymer according to claim 1 or 2, wherein the mass content of the polyethylene glycol segment in the block copolymer is from 10% by mass to 80% by mass.

4. The block copolymer according to claim 3, wherein the mass content of the polyethylene glycol segment in the block copolymer is from 30% by mass to 65% by mass.

5. The block copolymer according to claim 1 or 2, wherein the molecular weight of the polyethylene glycol segment is 1 kilodalton to 10 kilodaltons.

6. The block copolymer according to claim 1 or 2, wherein the mass content of the physiologically active substance having the hydroxyl group in the block copolymer is from 10% by mass to 60% by mass.

7. The block copolymer according to claim 1 or 2, wherein the block copolymer is represented by General Formula (1):

(1)

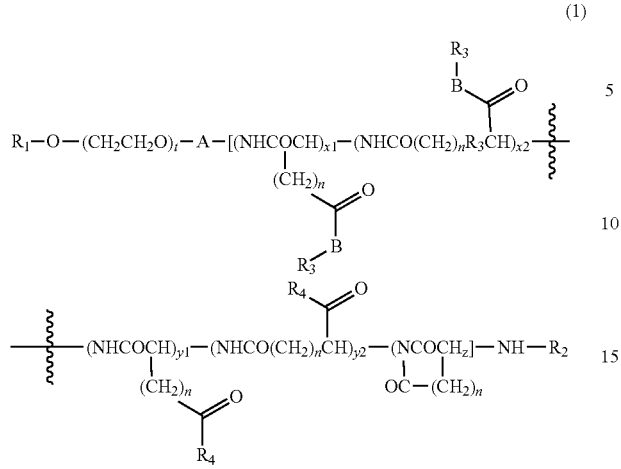

wherein $R_1$ represents a hydrogen atom or a C1-C6 alkyl group which may have a substituent;

t represents an integer of 20 to 270; A represents a C1-C6 alkylene group which may have a substituent; $R_2$ represents a substituent selected from the group consisting of a hydrogen atom, a C1-C6 acyl group, and a C1-C6 alkoxycarbonyl group; B represents a bond or a linking group having a carboxyl group; $R_3$ represents a residue of a physiologically active substance with a hydroxyl group, where the hydroxyl group is linked to B; $R_4$ represents one or more substituents selected from the group consisting of a linear, branched or cyclic C1-C30 alkoxy group which may have a substituent, a linear, branched or cyclic C1-C30 alkylamino group which may have a substituent, a linear, branched or cyclic C1-C30 dialkylamino group which may have a substituent, a C1-C8 alkylaminocarbonyl-C1-C8 alkylamino group which may have a substituent, a residue of a fluorescent substance, and a hydroxyl group; n represents 1 or 2; $x_1$, $x_2$, $y_1$, $y_2$, and z each independently represent an integer of 0 to 25; $(x_1+x_2)$ represents an integer of 1 to 25; $(x_1+x_2+y_1+y_2+z)$ represents an integer of 3 to 25; and the each constituent unit to which $R_3$ or $R_4$ is linked, and the constituent unit in which a side chain carbonyl group is intramolecularly cyclized are each independently randomly arranged.

8. The block copolymer according to claim 7, wherein $R_3$ represents a residue of a camptothecin derivative represented by General Formula (2):

(2)

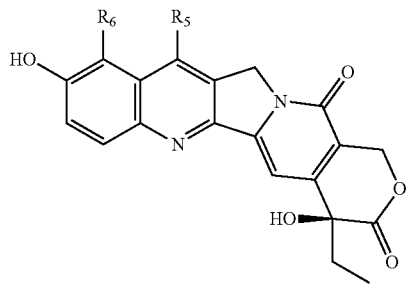

wherein $R_5$ represents one selected from the group consisting of a hydrogen atom, a C1-C6 alkyl group which may have a substituent, and a silyl group which may have a substituent; and $R_6$ represents a hydrogen atom or a C1-C6 alkyl group which may have a substituent; and wherein any one of the hydroxyl groups of the camptothecin derivative is linked to B of General Formula (1) as defined in claim 7.

9. The block copolymer according to claim 7, wherein $R_3$ represents a residue of a resorcinol derivative represented by General Formula (3):

(3)

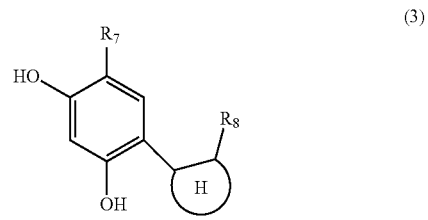

wherein $R_7$ represents one selected from the group consisting of a mercapto group, a hydroxyl group, a halogen atom, a nitro group, a cyano group, a C1-C20 alkyl group, a C2-C20 alkenyl group, a C2-C20 alkynyl group, a carbocyclic or heterocyclic aryl group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxy group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, a carboxyl group, a C1-C8 alkoxycarbonyl group, a carbamoyl group, and a C1-C8 alkylsilyl group;

$R_8$ represents one selected from the group consisting of a carbocyclic or heterocyclic aryl group which may have a substituent, a C1-C20 alkyl group, a C2-C20 alkenyl group, a C2-C20 alkynyl group, a C1-C20 alkylamino group, and a C1-C20 acylamino group; and ring H represents a heterocyclic aryl group selected from the group consisting of General Formulae (3-1), (3-2), and (3-3):

(3-1)

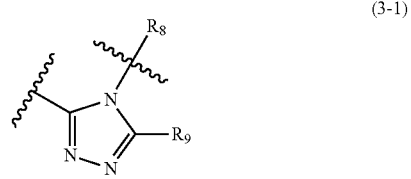

(3-2)

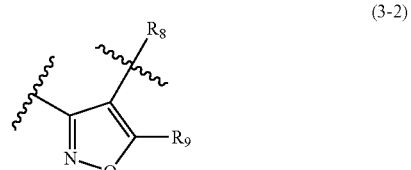

(3-3)

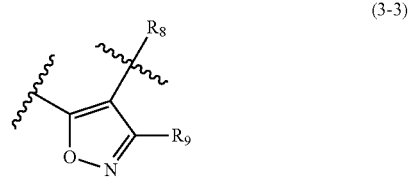

wherein R₉ represents one selected from the group consisting of a mercapto group, a hydroxyl group, a hydrogen atom, a halogen atom, a carbamoyl group, a C1-C20 alkoxycarbonyl group, a cyano group, a C1-C8 alkylthio group, an arylthio group, a C1-C8 alkylsulfinyl group, an arylsulfinyl group, a C1-C8 alkylsulfonyl group, an arylsulfonyl group, a sulfamoyl group, a C1-C8 alkoxyl group, an aryloxy group, a C1-C8 acyloxy group, a C1-C8 alkoxycarbonyloxy group, a carbamoyloxy group, an amino group, a C1-C8 acylamino group, a C1-C8 alkoxycarbonylamino group, a ureido group, a sulfonylamino group, a sulfamoylamino group, a formyl group, a C1-C8 acyl group, and a C1-C8 alkylsilyl group; and wherein any one of the hydroxyl groups of the resorcinol derivative is linked to B of General Formula (1) as defined in claim 7.

10. The block copolymer according to claim 7, wherein R₃ represents a residue of paclitaxel, docetaxel, or cabazitaxel, and wherein any one of the hydroxyl groups in paclitaxel, docetaxel, or cabazitaxel is linked to B of General Formula (1) as defined in claim 7.

11. The block copolymer according to claim 1 or 2, wherein the physiologically active substance with a hydroxyl group is one or more physiologically active substances selected from the group consisting of a camptothecin derivative, a taxane derivative, a resorcinol derivative, an anthracycline derivative, a rapamycin derivative, a cytidine-based antimetabolite, a folic acid antimetabolite, a purine-based antimetabolite, a fluorinated pyrimidine-based antimetabolite, a platinum derivative, a mitomycin derivative, a bleomycin derivative, a vinca alkaloid derivative, a podophyllotoxin derivative, a halichondrin derivative, a staurosporine derivative, a thalidomide derivative, a vitamin A derivative, a combretastatin derivative, an antiandrogen agent, an antiestrogen agent, a hormone agent, a tacrolimus derivative, a steroid derivative, a polyene-based antibiotic substance, an azole-based derivative, a candin-based derivative, and a pyrimidine derivative.

12. The block copolymer according to claim 11, wherein the physiologically active substance with a hydroxyl group is one or more antitumor agents selected from the group consisting of a camptothecin derivative, a taxane derivative, a resorcinol derivative, an anthracycline derivative, a rapamycin derivative, a cytidine-based antimetabolite, a folic acid antimetabolite, a purine-based antimetabolite, a fluorinated pyrimidine-based antimetabolite, a platinum derivative, a mitomycin derivative, a bleomycin derivative, a vinca alkaloid derivative, a podophyllotoxin derivative, a halichondrin derivative, a staurosporine derivative, a thalidomide derivative, a vitamin A derivative, a combretastatin derivative, an antiandrogen agent, an antiestrogen agent, and a hormone agent.

13. Nanoparticles formed from the block copolymer according to claim 1 or 2.

14. A pharmaceutical product comprising the block copolymer according to claim 1 or 2, as an active ingredient.

15. An antitumor agent comprising the block copolymer according to claim 1 or 2, as an active ingredient.

16. A block copolymer obtained by reacting a block copolymer in which a polyethylene glycol segment is connected with a polyamino acid segment including aspartic acid and/or glutamic acid, with a physiologically active substance having a hydroxyl group, and optionally with hydrophobic substituent having a hydroxyl group and/or an amino group, by using a condensing agent, wherein the molecular weight of the block copolymer is from 2 kilodaltons to 15 kilodaltons, and the light scattering intensity of a 1 mg/mL aqueous solution of the block copolymer as measured with a laser light scattering photometer under the measurement conditions of a measurement temperature of 25° C., a scattering angle of 90°, and a wavelength of 632.8 nm, is at least twice or more the light scattering intensity of toluene measured under the same measurement conditions.

17. The nanoparticles according to claim 13, wherein a volume average particle diameter of the nanoparticles is less than 20 nanometers.

18. Nanoparticles formed from the block copolymer according to claim 16.

19. The nanoparticles according to claim 18, wherein a volume average particle diameter of the nanoparticles is less than 20 nanometers.

20. A pharmaceutical product comprising the block copolymer according to claim 16, as an active ingredient.

21. An antitumor agent comprising the block copolymer according to claim 16, as an active ingredient.

* * * * *